US012678792B2

(12) United States Patent
Glezer et al.

(10) Patent No.: US 12,678,792 B2
(45) Date of Patent: *Jul. 14, 2026

(54) METHODS FOR CONDUCTING MULTIPLEXED ASSAYS

(71) Applicant: Meso Scale Technologies, LLC., Rockville, MD (US)

(72) Inventors: Eli N. Glezer, Del Mar, CA (US); Sudeep Kumar, Gaithersburg, MD (US); Pankaj Oberoi, Rockville, MD (US); George Sigal, Rockville, MD (US); Michael Tsionsky, Derwood, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/476,880

(22) Filed: Sep. 16, 2021

(65) Prior Publication Data

US 2021/0402390 A1     Dec. 30, 2021

Related U.S. Application Data

(60) Continuation of application No. 16/210,165, filed on Dec. 5, 2018, now Pat. No. 11,148,145, which is a division of application No. 14/203,638, filed on Mar. 11, 2014, now Pat. No. 10,189,023.

(60) Provisional application No. 61/778,727, filed on Mar. 13, 2013, provisional application No. 61/775,860, filed on Mar. 11, 2013.

(51) Int. Cl.
| | |
|---|---|
| *C12Q 1/68* | (2018.01) |
| *B01L 3/00* | (2006.01) |
| *C12Q 1/6804* | (2018.01) |
| *C12Q 1/6816* | (2018.01) |
| *C12Q 1/6876* | (2018.01) |
| *G01N 33/543* | (2006.01) |
| *G01N 33/68* | (2006.01) |

(52) U.S. Cl.
CPC ........ *B01L 3/50853* (2013.01); *C12Q 1/6804* (2013.01); *C12Q 1/6816* (2013.01); *C12Q 1/6876* (2013.01); *G01N 33/54306* (2013.01); *G01N 33/54353* (2013.01); *G01N 33/6845* (2013.01); *B01L 2300/021* (2013.01); *B01L 2300/043* (2013.01); *B01L 2300/0609* (2013.01); *B01L 2300/0829* (2013.01); *G01N 2458/10* (2013.01)

(58) Field of Classification Search
USPC .......... 435/6.1, 6.11, 7.1, 91.1, 283.1, 287.1, 435/287.2; 436/94, 501; 536/23.1, 24.3, 536/24.33
See application file for complete search history.

(56) References Cited

U.S. PATENT DOCUMENTS

| | | |
|---|---|---|
| 4,139,346 A | 2/1979 | Rabbani |
| 4,161,515 A | 7/1979 | Ullman |
| 4,272,478 A | 6/1981 | Vihko |
| 4,315,907 A | 2/1982 | Ames-Yissum |
| 4,378,344 A | 3/1983 | Zahradnik et al. |
| 4,514,508 A | 4/1985 | Hirschfeld |
| 4,587,044 A | 5/1986 | Miller et al. |
| 4,748,111 A | 5/1988 | Dattagupta et al. |
| 4,870,003 A | 9/1989 | Kortright et al. |
| 4,889,798 A | 12/1989 | Rabbani |
| 4,894,325 A | 1/1990 | Englehardt et al. |
| 4,939,098 A | 7/1990 | Suzuki et al. |
| 5,093,268 A | 3/1992 | Leventis et al. |
| 5,124,246 A | 6/1992 | Urdea et al. |
| 5,126,278 A | 6/1992 | Fish et al. |
| 5,143,852 A | 9/1992 | Valkirs et al. |
| 5,147,806 A | 9/1992 | Kamin et al. |
| 5,238,808 A | 8/1993 | Bard et al. |
| 5,240,863 A | 8/1993 | Shibue et al. |
| 5,242,804 A | 9/1993 | Bahar et al. |
| 5,288,609 A | 2/1994 | Engelhardt et al. |
| 5,308,754 A | 5/1994 | Kankare et al. |
| 5,324,457 A | 6/1994 | Zhang et al. |
| 5,354,655 A | 10/1994 | Ward, Jr. et al. |
| 5,391,723 A | 2/1995 | Priest |
| 5,415,839 A | 5/1995 | Zaun et al. |
| 5,422,283 A | 6/1995 | Ismail |
| 5,437,983 A | 8/1995 | Watts et al. |
| 5,464,746 A | 11/1995 | Fino |
| 5,516,635 A | 5/1996 | Ekins et al. |

(Continued)

FOREIGN PATENT DOCUMENTS

| | | |
|---|---|---|
| CN | 1186513 A | 7/1998 |
| CN | 101208437 A | 6/2008 |

(Continued)

OTHER PUBLICATIONS

Boozer C. et al., "DNA-Directed Protein Immobilization for Simultaneous Detection of Multiple Analytes by Surface Plasmon Resonance Biosensor", Analytical Chemistry 78(5):1515-1519 (Mar. 1, 2006).

(Continued)

*Primary Examiner* — Frank W Lu

(74) *Attorney, Agent, or Firm* — MEDLER FERRO WOODHOUSE & MILLS PLLC

(57) ABSTRACT

The invention relates to methods for conducting solid-phase binding assays. One example is an assay method having improved analyte specificity where specificity is limited by the presence of non-specific binding interactions.

26 Claims, 19 Drawing Sheets

Specification includes a Sequence Listing.

(56)                    References Cited

U.S. PATENT DOCUMENTS

| | | | |
|---|---|---|---|
| 5,518,887 | A | 5/1996 | Parsons et al. |
| 5,525,465 | A | 6/1996 | Haralambidis et al. |
| 5,527,681 | A | 6/1996 | Holmes |
| 5,561,043 | A | 10/1996 | Cantor et al. |
| 5,567,627 | A | 10/1996 | Lehnen |
| 5,573,905 | A | 11/1996 | Lerner et al. |
| 5,589,136 | A | 12/1996 | Northrup et al. |
| 5,591,581 | A | 1/1997 | Massey et al. |
| 5,597,910 | A | 1/1997 | Gudibande et al. |
| 5,620,850 | A | 4/1997 | Bamdad et al. |
| 5,629,153 | A | 5/1997 | Urdea |
| 5,635,602 | A | 6/1997 | Cantor et al. |
| 5,641,623 | A | 6/1997 | Martin |
| 5,643,713 | A | 7/1997 | Liang et al. |
| 5,648,213 | A | 7/1997 | Reddy et al. |
| 5,665,539 | A | 9/1997 | Sano et al. |
| 5,679,519 | A | 10/1997 | Oprandy |
| 5,705,402 | A | 1/1998 | Leland et al. |
| 5,719,063 | A | 2/1998 | Block |
| 5,723,320 | A | 3/1998 | Dehlinger |
| 5,726,064 | A | 3/1998 | Robinson et al. |
| 5,731,147 | A | 3/1998 | Bard et al. |
| 5,731,162 | A | 3/1998 | Gatti et al. |
| 5,750,338 | A | 5/1998 | Collins et al. |
| 5,770,358 | A | 6/1998 | Dower et al. |
| 5,776,672 | A | 7/1998 | Hashimoto et al. |
| 5,786,141 | A | 7/1998 | Bard et al. |
| 5,795,714 | A | 8/1998 | Cantor et al. |
| 5,846,485 | A | 12/1998 | Leland et al. |
| 5,849,478 | A | 12/1998 | Cashman |
| 5,849,878 | A | 12/1998 | Cantor et al. |
| 5,866,434 | A | 2/1999 | Massey et al. |
| 5,877,028 | A | 3/1999 | Chandler et al. |
| 6,066,448 | A | 5/2000 | Wohlstadter et al. |
| 6,087,491 | A | 7/2000 | Tang et al. |
| 6,136,268 | A | 10/2000 | Ala-Kleme et al. |
| 6,207,369 | B1 | 3/2001 | Wohlstadter et al. |
| 6,214,552 | B1 | 4/2001 | Heroux et al. |
| 6,261,776 | B1 | 7/2001 | Pirrung et al. |
| 6,325,973 | B1 | 12/2001 | Leland et al. |
| 6,406,844 | B1 | 6/2002 | Pirrung et al. |
| 6,448,091 | B1 | 9/2002 | Massey et al. |
| 6,939,720 | B2 | 9/2005 | Chandler et al. |
| 6,942,972 | B2 | 9/2005 | Farooqui et al. |
| 6,977,722 | B2 | 12/2005 | Wohlstadter et al. |
| 7,070,740 | B1 | 7/2006 | Matson et al. |
| 7,195,875 | B2 | 3/2007 | Keys et al. |
| 7,229,763 | B2 | 6/2007 | Reddy et al. |
| 7,422,855 | B2 | 9/2008 | Dicesare |
| 7,494,776 | B2 | 2/2009 | Wallace et al. |
| 7,569,341 | B2 | 8/2009 | Niemeyer et al. |
| 7,771,935 | B2 | 8/2010 | Liu et al. |
| 7,842,246 | B2 | 11/2010 | Wohlstadter et al. |
| 7,939,313 | B2 | 5/2011 | Heyduk et al. |
| 10,201,812 | B2 * | 2/2019 | Glezer ............. G01N 33/54306 |
| 11,148,145 | B2 * | 10/2021 | Glezer ................ B01L 3/50853 |
| 11,951,483 | B2 * | 4/2024 | Glezer ................ B01L 3/50853 |
| 2002/0006614 | A1 | 1/2002 | Mitchison |
| 2004/0049351 | A1 | 3/2004 | Matson et al. |
| 2006/0134712 | A1 | 6/2006 | Stromgren et al. |
| 2010/0028954 | A1 | 2/2010 | Kless |
| 2010/0159446 | A1 | 6/2010 | Haff et al. |
| 2010/0261292 | A1 | 10/2010 | Glezer et al. |
| 2011/0306511 | A1 | 12/2011 | Lea |
| 2012/0258870 | A1 * | 10/2012 | Schwartz ............. C12Q 1/6804 506/4 |
| 2014/0256588 | A1 | 9/2014 | Glezer et al. |

FOREIGN PATENT DOCUMENTS

| | | |
|---|---|---|
| CN | 101952719 A | 1/2011 |
| CN | 102099462 A | 6/2011 |
| JP | 2008-546407 A | 12/2008 |
| WO | 97/36931 A1 | 10/1997 |
| WO | 98/12539 A1 | 3/1998 |
| WO | 98/24928 A2 | 6/1998 |
| WO | 98/57154 A1 | 12/1998 |
| WO | 99/14599 A1 | 3/1999 |
| WO | 99/32662 A1 | 7/1999 |
| WO | 99/58962 A1 | 11/1999 |
| WO | 99/63347 A1 | 12/1999 |
| WO | 00/03233 A1 | 1/2000 |
| WO | 2007/001817 A1 | 1/2007 |
| WO | 2008/156249 A1 | 12/2008 |
| WO | 2009/012340 A2 | 1/2009 |
| WO | 2009/098045 A1 | 8/2009 |

OTHER PUBLICATIONS

Brenner S. et al., "Encoded Combinatorial Chemistry", Proc. Natl. Acad, Sci. USA 89:5381-5383 (Jun. 1992).

Broude N.E. et al., "Enhanced DNA Sequencing by Hybridization", Proc. Natl. Acad. Sci. USA 91:3072-3076 (Apr. 1994).

Brown C.R. et al., "Simultaneous Determination of Total IgE and Allergen-Specific IgE in Serum by the MAST Chemiluminescent Assay System", Clinical Chemistry 31(9):1500-1505 (1985).

Buechler K.F. et al., "Simultaneous Detection of Seven Drugs of Abuse by the Triage™ Panel for Drugs of Abuse", Clinical Chemistry 38(9):1678-1684 (1992).

Carpenter W.R. et al., "A Transcriptionally Amplified DNA Probe Assay with Ligatable Probes and Immunochemical Detection", Clinical Chemistry 39(9):1934-1938 (1993).

Donohue J. et al., "Enzyme Immunoassay System for Panel Testing", Clinical Chemistry 35(9):1874-1877 (1989).

Guglielmo-Viret V. et al., "Comparison of an Electrochemiluminescence Assay in Plate Format Over a Colorimetric ELISA, for the Detection of Ricin B Chain (RCA-B)", Journal of Immunological Methods 328:70-78 (2007).

Hochman J. et al., "An Active Antibody Fragment (Fv) Composed of the Variable Portions of Heavy and Light Chains", Biochemistry 12(6):1130-1135 (1973).

Hu W-P et al., "Optiminization of DNA-Directed Immobilization on Mixed Oligo(Ethylene Glycol) Monolayers for Immunodetection", Analytical Biochemistry 423(1):26-35 (Dec. 2012).

Ito T. et al., "Sequence-Specific DNA Purification by Triplex Affinity Capture", Pro. Natl. Acad. Sci. USA 89:495-498 (Jan. 1992).

Jung Y. et al., "Self-Directed and Self-Oriented Immobilization of Antibody by Protein G-DNA Conjugate", Anal. Chem. 79(17):6534-6541 (Sep. 1, 2007).

Kakabakos S.E. et al., "Multianalyte Immunoassay Based on Spatially Distinct Fluorescent Areas Quantified by Laser-Excited Solid-Phase Time-Resolved Fluorometry", Clinical Chemistry 38(3):338-342 (1992).

Kim D.C. et al., "Molecular Recognition and Specific Interactions for Biosensing Applications", Sensors 8(10):6605-6641 (Oct. 2008).

Kuijpers WH et al., "Specific Recognition of Antibody-Oligonucleotide Conjugates by Radiolabeled Antisense Nucleotides: A Novel for Two-Step Radioimmunotherapy of Cancer", Bioconjug Chem. 4(1):94-102 (Jan.-Feb. 1993). abstract only.

Ladd J. et al., "DNA-Directed Protein Immobilization on Mixed Self-Assembled Monolayers Via a Streptavidin Bridge", Langmuir 20(19):8090-8095 (2004).

Mantero G. et al., "DNA Enzyme Immunoassay: General Method for Detecting Products of Polymerase Chain Reaction", Clinical Chemistry 37(3):422-429 (1991).

Matson R.S. et al., "The A2 MicroArray System: An Option Platform for Multiplex Immunoassay Development", Retrieved from the Internet: URL:www.quantiscientifics.com/uploads/A2_MicroArray_System-SelectScience.pdf (8 pages) (Dec. 2010).

Niemeyer C.M. et al., "Oligonucleotide-Directed Self-Assembly of Proteins: Semisynthetic DNA-Streptavidin Hybrid Molecules as Connectors for the Generation of Macroscopic Arrays and the Construction of Supramolecular Bioconjugates", Nucleic Acids Research 22(25):5530-5539 (1994).

(56) References Cited

OTHER PUBLICATIONS

Porter R.R. et al., "Subunits of Immunoglobulins and Their Relationship to Antibody Specificity", J. Cell Physiol 67, Sup. 1:51-64 (1966).

Roy, Jr., PH.D. S.H.C., "Characterization of a Multi-Receptor Complex on the T Cell Surface: Association of CD4 With the T Cell Antigen Receptor", Dissertation Abstracts International 54(2):5938 (Aug. 1993), abstract only.

Saiyudthong S. et al., "Comparison Between ECL and ELISA for the Detection of Salivary Cortisol and Determination of the Relationship Between Cortisol in Saliva and Serum Measured by ECL", ScienceAsia 36:169-171 (2010).

Sano T. et al., "Immuno-PCR: Very Sensitive Antigen Detection by Means of Specific Antibody-DNA Conjugates", Science 258:120-122 (Oct. 2, 1992).

Sano T. et al., "Expression of Active Streptavidin in E. Coli and its Application to New Detection Systems With Streptavidin-Containing Fusion Proteins", Biochemistry and Molecular Biology of Biosensors and Bioprobes CG302, p. 368, abstract only (1990).

Song K-S et al., "9G DNAChip: A Platform for the Efficient Detection of Proteins", Chemical Communications 47(27):7716-7718 (Jan. 2011).

Stratagene Catalog, Published by Stratgene, 11011 North Torrey Pines Road, La Jolla, CA 92037, USA, p. 39 (1988).

Wang C-H K. et al., "Substrate-Mediated Nucleic Acid Delivery from Self-Assembled Monolayers", Trends in Biotechnology 29(3):119-126 (Mar. 2011).

Xiao-Yan C. et al., "A Highly Sensitive Electrochemiluminescence Immunoassay for Detecting Human Embryonic Human Chorionic Gonadotropin in Spent Embryo Culture Media During IVF-ET Cycle", J Assit Reprod Genet 30:377-382 (2013).

Quantiscientifics: "Optimization of Oligo-Antibody Conjugate Loading for Use in the A2® Mutiplex ELISA", Retrieved from the Internet: URL:http://quantiscientifics. com/uploads/Application_Note_2_Optimizing_Conjugate_Loading.pdf (4 pages) (Sep. 18, 2012).

Quantiscientifics: "The A2® Multiplex ELISA Human Cytokine Panel", Retrieved from the Internet: URL:http://quantiscientifics. com/uploads/Application_Note_1_Cytokines.pdf (2 pages) (Jul. 13, 2012).

Quantiscientifics: "The A2 MicroArray System-An Open Platform for Multiplexed Assay Development", Retrieved from the Internet: URL:http://quantiscientifics.com/uploads/Application_Note_1_ Cytokines.pdf (1 page) (Nov. 3, 2012).

Quantiscientifics: "Application Notes", Retrieved from the Internet: URL:wayback.archive.org/web/20121103021146/http://quantiscientifics. com/A2_Applications.html (1 page) (Nov. 3, 2012).

NCBI, Reference Sequence No. XM_002283694.2 (2 pages) (Dec. 7, 2011).

NCBI, GenBank Accession No. BP608643.1 (1 page) (Feb. 9, 2011).

NCBI, GenBank Accession No. DN155865.1 (1 page) (Dec. 30, 2010).

NCBI, GenBank Accession No. CP000925.1 (526 pages) (Mar. 10, 2008).

International Search Report and Written Opinion dated Aug. 11, 2014 received from the International Searching Authority from related Application No. PCT/US2014/022948.

Japanese Notice of Reasons for Rejection dated Oct. 23, 2018 received in Japanese Patent Application No. 2016-501106, together with an English-language translation.

Japanese Notice of Reasons for Rejection dated Nov. 28, 2017 received in Japanese Patent Application No. 2016-501106, together with an English-language translation.

Chinese Office Action dated Aug. 10, 2018 received in Chinese Patent Application No. 201480026770.1, together with an English-language translation.

Chinese Office Action dated Mar. 27, 2017 received in Chinese Patent Application No. 201480026770.1, together with an English-language translation.

European Communication dated Aug. 6, 2018 received in European Patent Application No. 14 778 374.0.

European Examination Report dated Nov. 6, 2017 received in European Patent Application No. 14 778 374.0.

Extended Supplementary European Search Report dated Dec. 5, 2016 received in European Patent Application No. 14 77 8374.

European Partial Supplementary Search Report dated Aug. 19, 2016 received in European Patent Application No. 14 77 8374.

European Communication dated Jul. 19, 2019 received in European Patent Application No. 14 778 374.0.

Japanese Notice of Reasons for Rejection dated Sep. 10, 2019 received in Japanese Patent Application No. 2016-501106, together with an English-language translation.

* cited by examiner

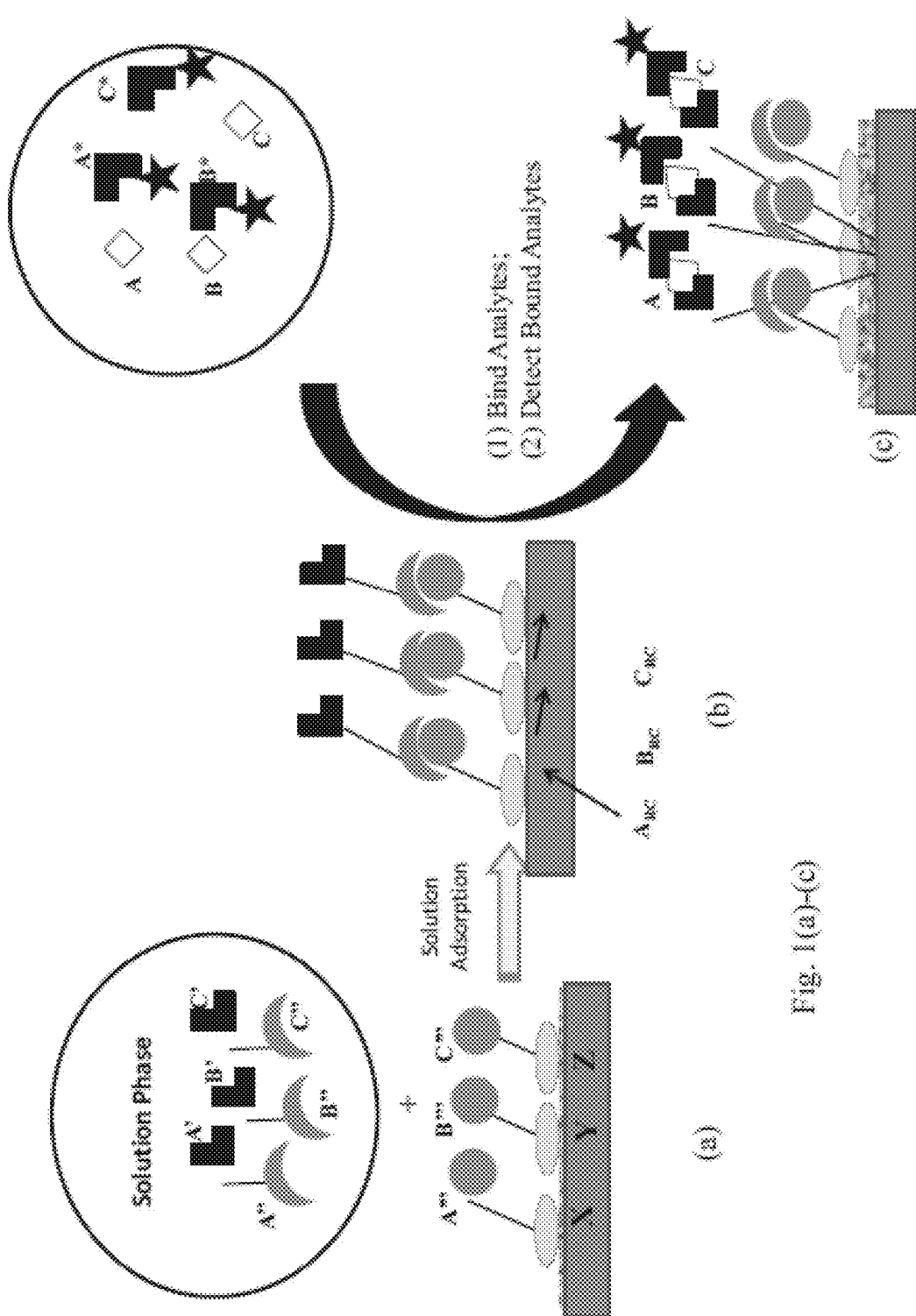
Fig. 1(a)–(c)

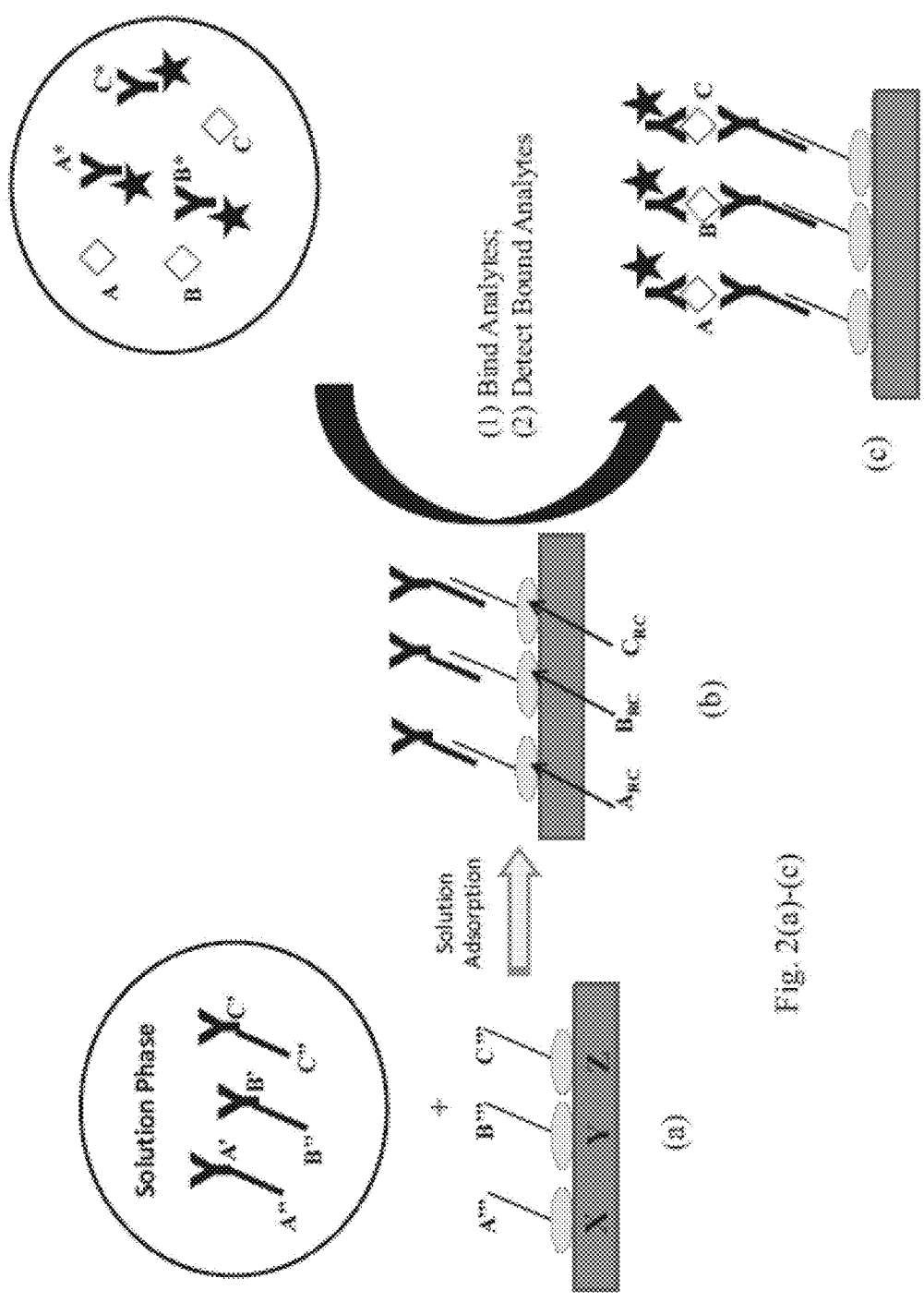
Fig. 2(a)-(c)

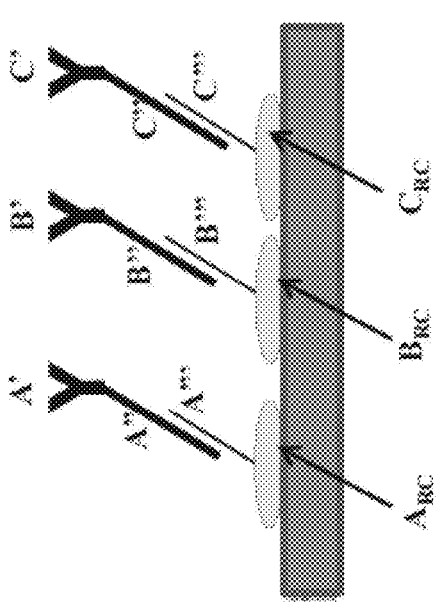
Fig. 2(d)

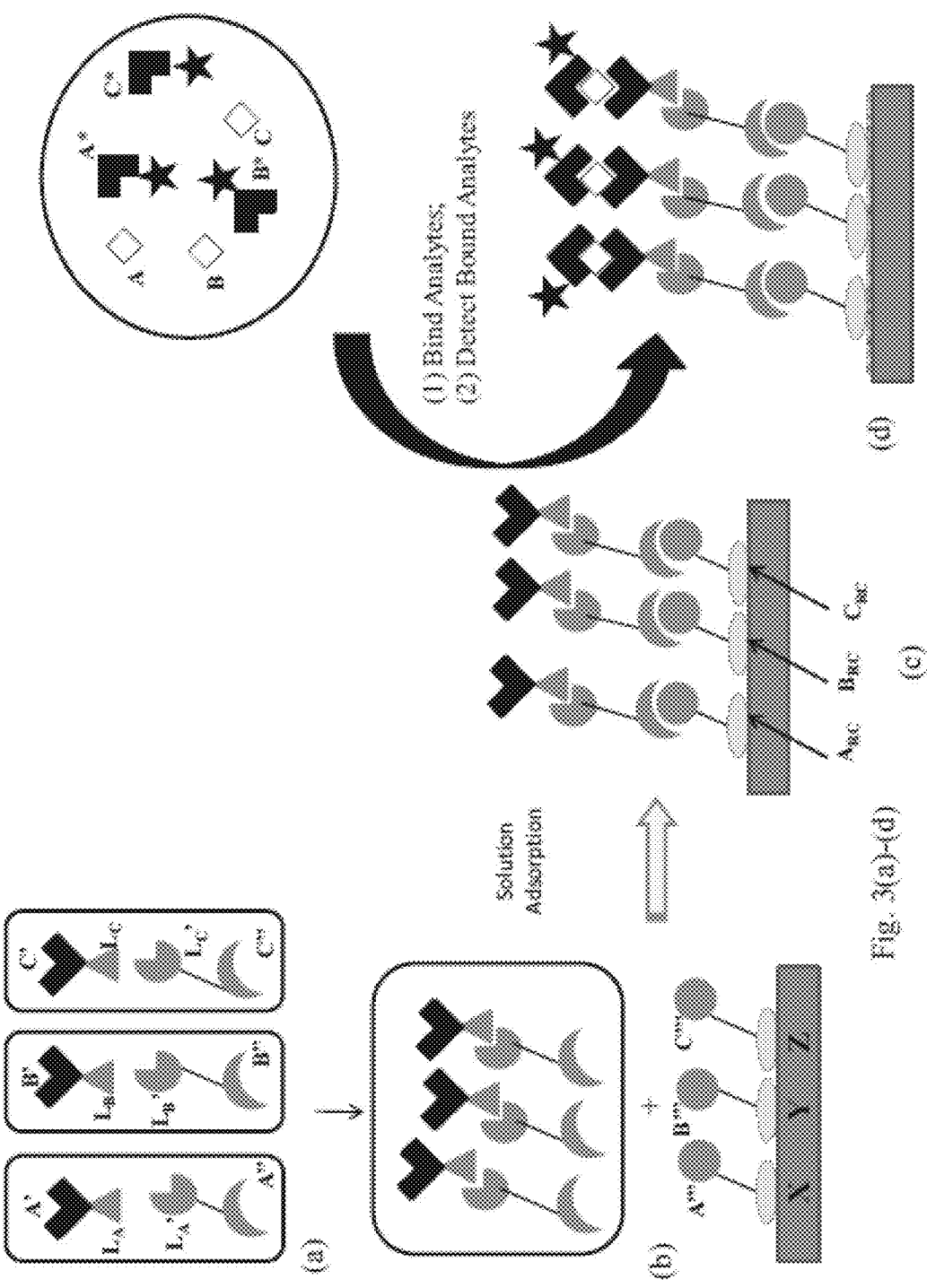
Fig. 3(a)-(d)

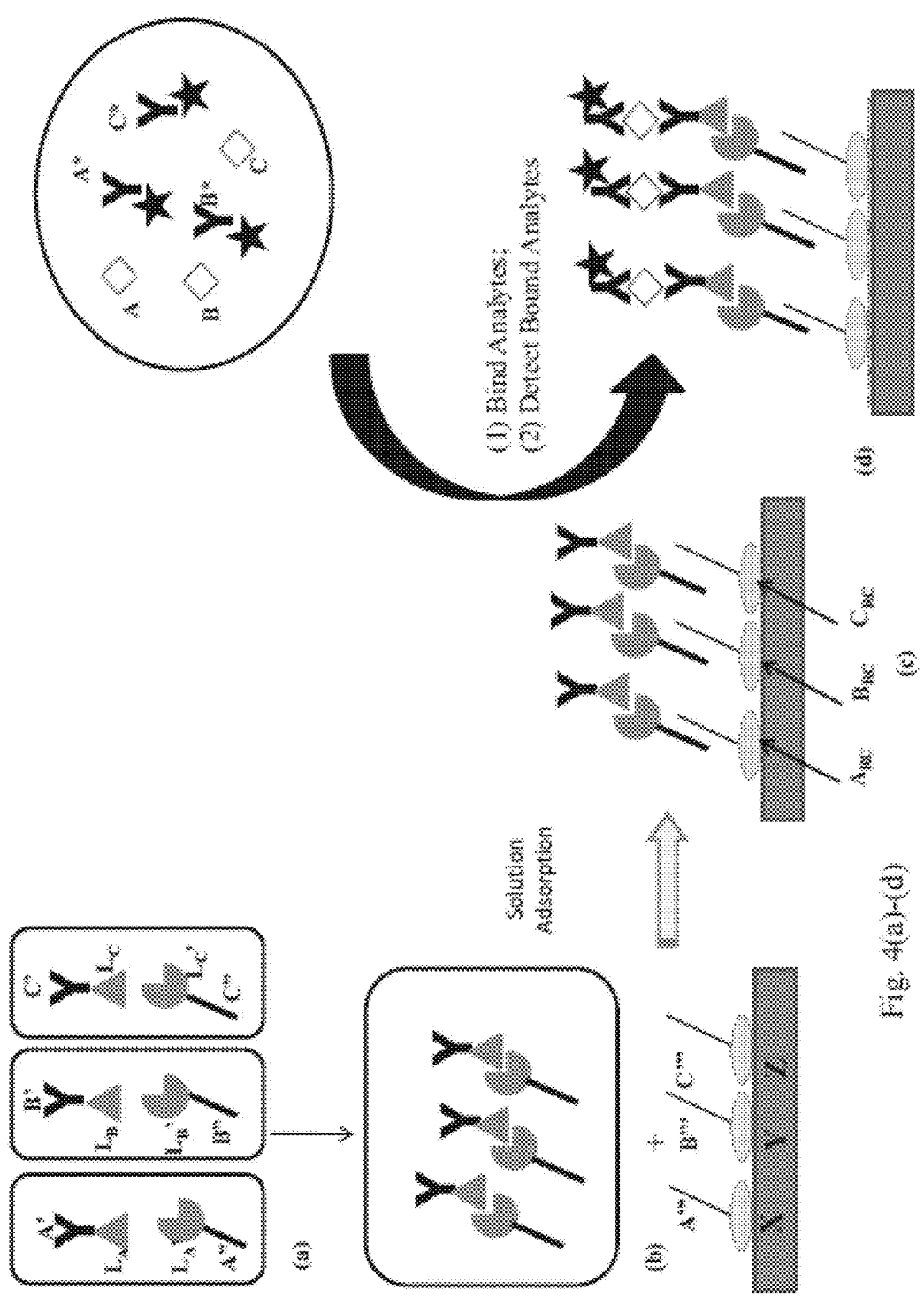
Fig. 4(a)–(d)

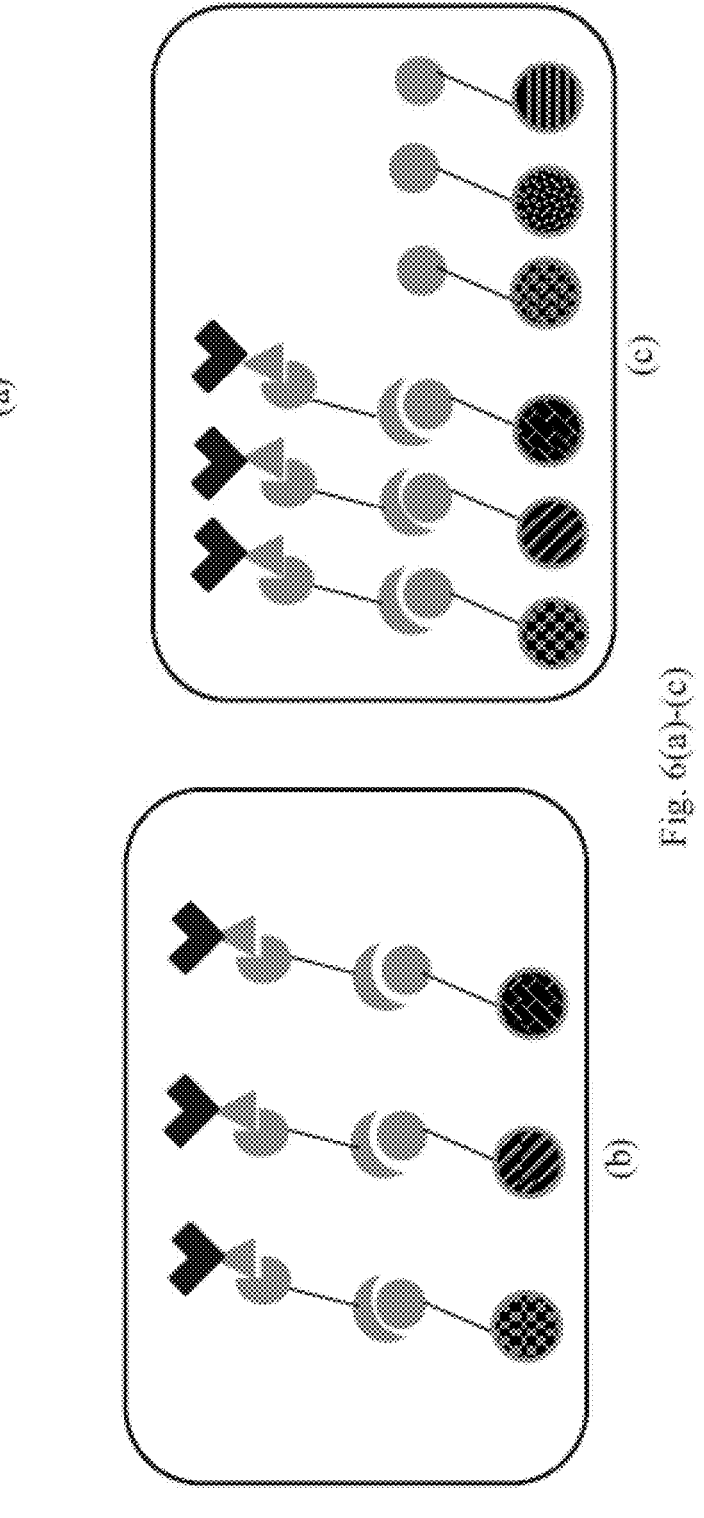
Fig. 6(a)-(c)

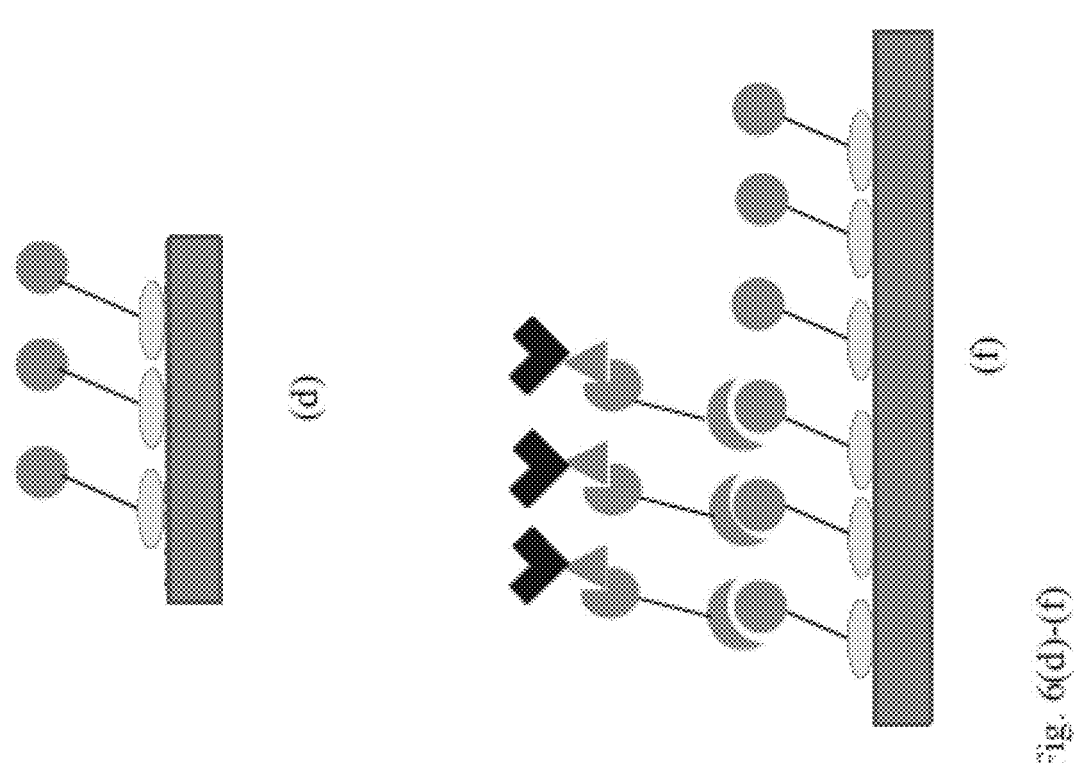
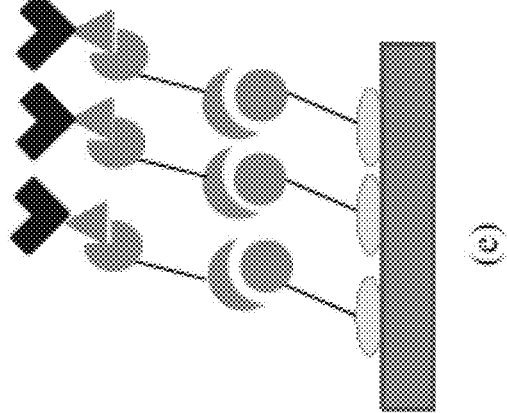
Fig. 6(d)-(f)

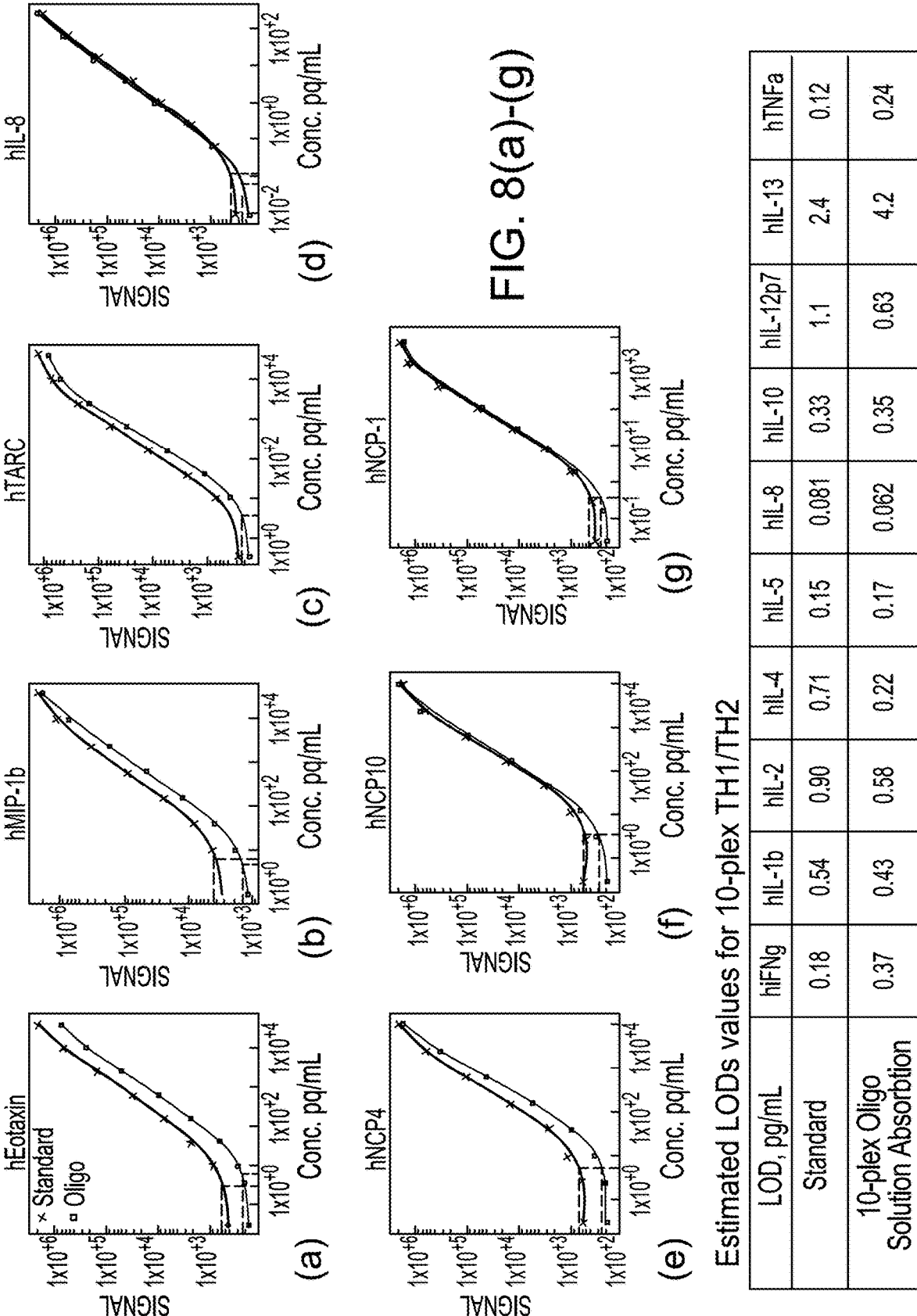
FIG. 8(a)-(g)
Estimated LODs values for 10-plex TH1/TH2
| LOD, pg/mL | hIFNg | hIL-1b | hIL-2 | hIL-4 | hIL-5 | hIL-8 | hIL-10 | hIL-12p7 | hIL-13 | hTNFa |
|---|---|---|---|---|---|---|---|---|---|---|
| Standard | 0.18 | 0.54 | 0.90 | 0.71 | 0.15 | 0.081 | 0.33 | 1.1 | 2.4 | 0.12 |
| 10-plex Oligo Solution Absorbtion | 0.37 | 0.43 | 0.58 | 0.22 | 0.17 | 0.062 | 0.35 | 0.63 | 4.2 | 0.24 |

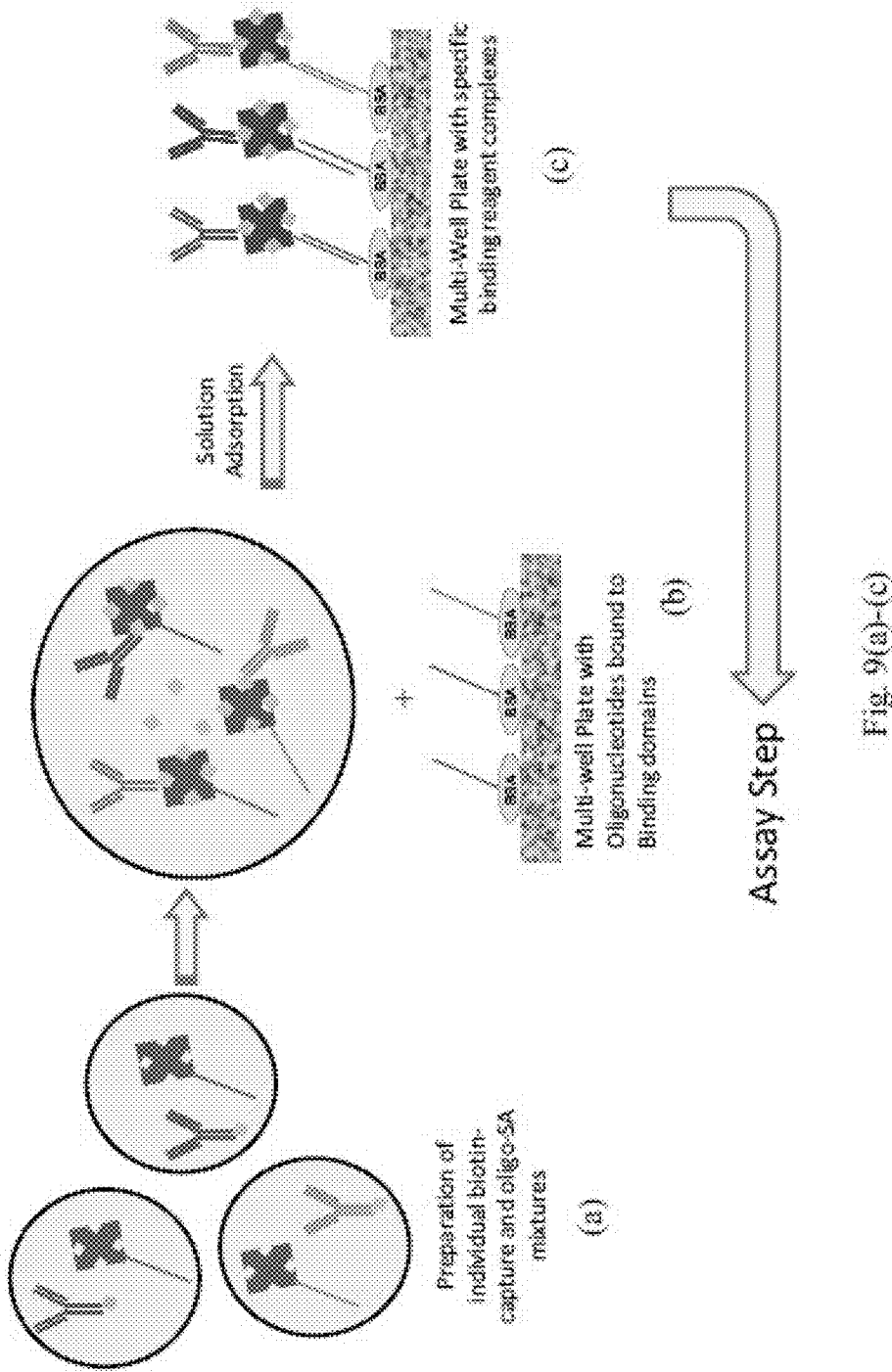
Fig. 9(a)-(c)

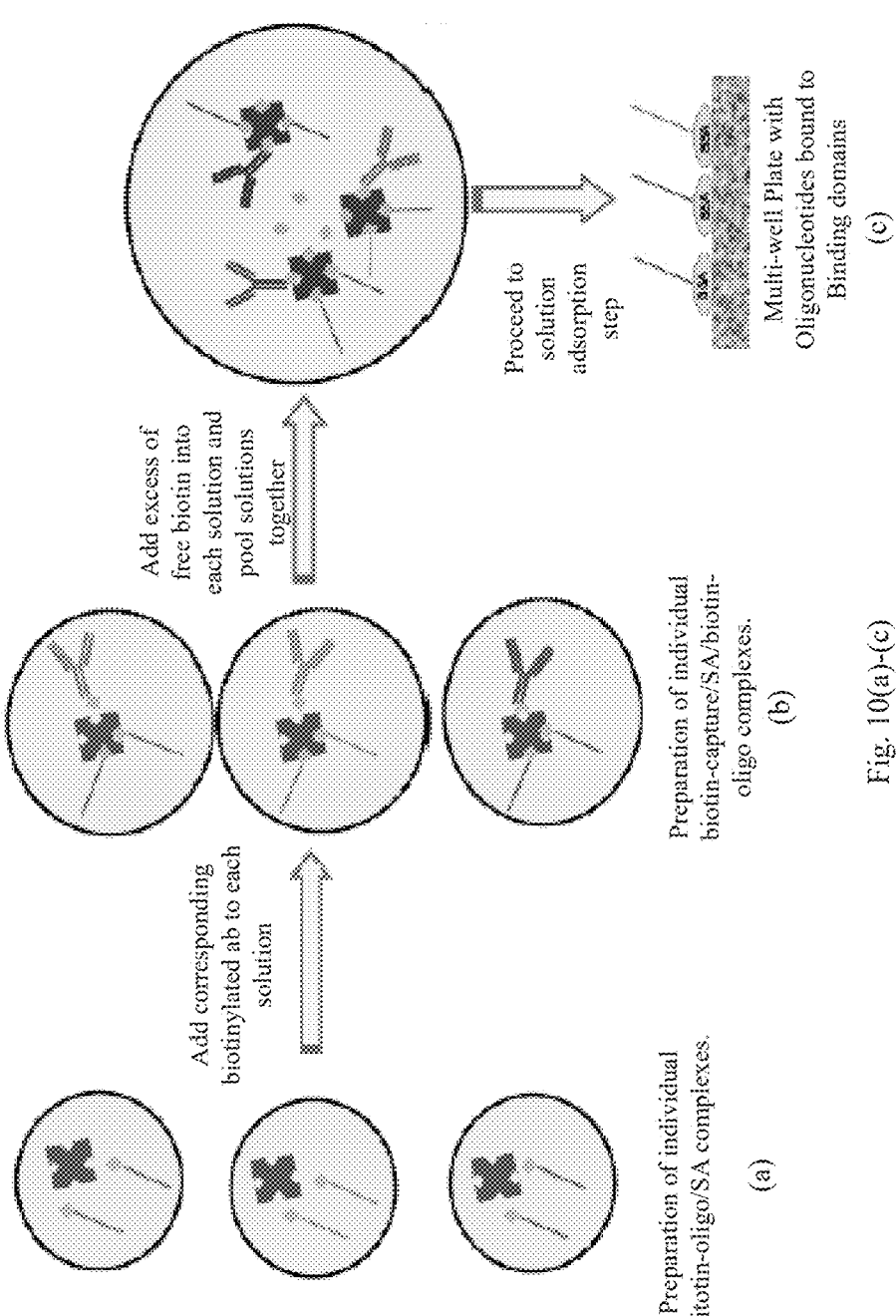

Preparation of individual biotin-oligo/SA complexes.
(a)

Add corresponding biotinylated ab to each solution

Preparation of individual biotin-capture/SA/biotin-oligo complexes.
(b)

Add excess of free biotin into each solution and pool solutions together

Proceed to solution adsorption step

Multi-well Plate with Oligonucleotides bound to Binding domains
(c)

Fig. 10(a)-(c)

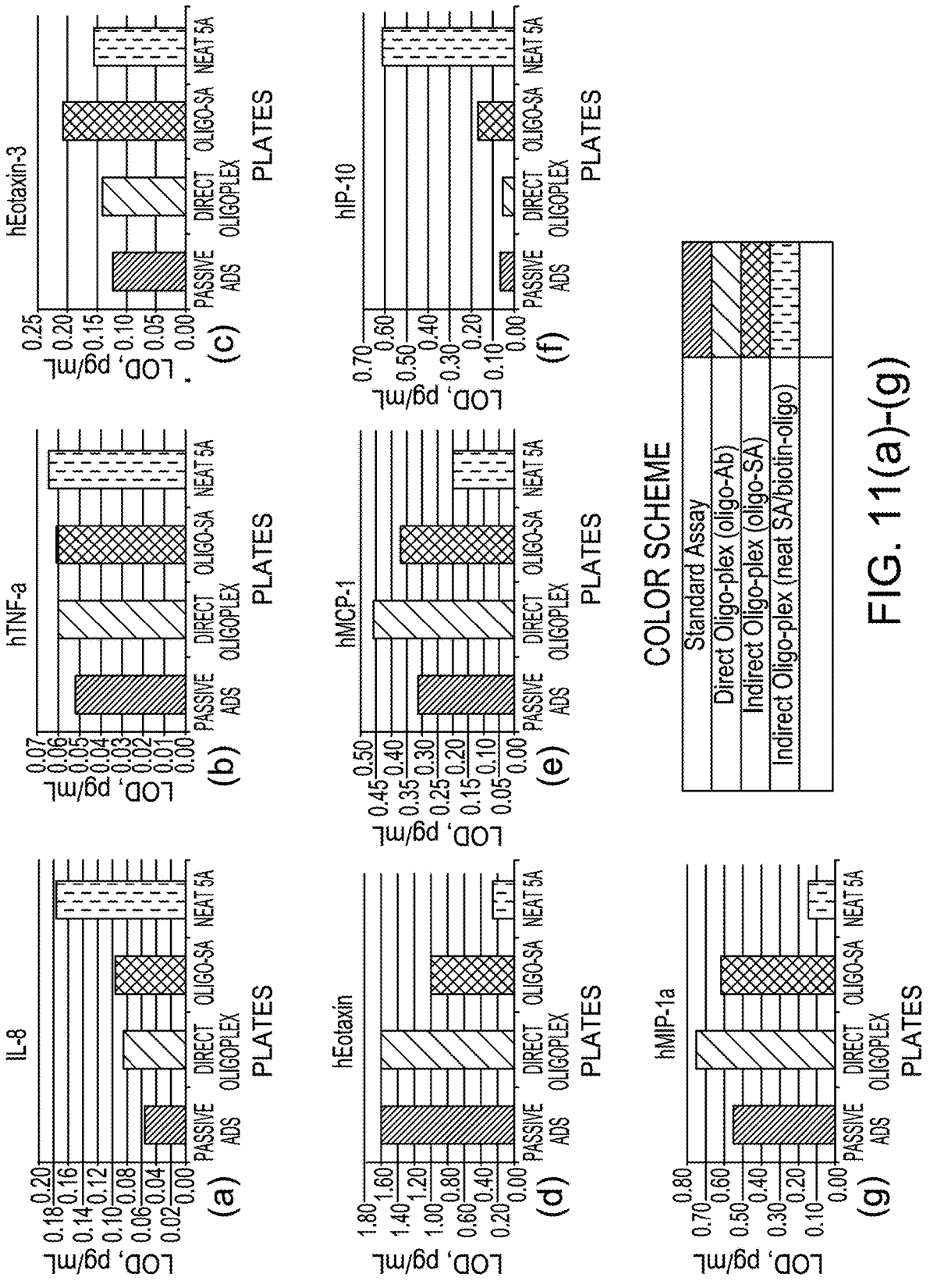
FIG. 11(a)-(g)

METHODS FOR CONDUCTING MULTIPLEXED ASSAYS

CROSS REFERENCE TO RELATED APPLICATIONS

The present application is a continuation of application Ser. No. 16/210,165, filed Dec. 5, 2018, issued as U.S. Pat. No. 11,148,145 on Oct. 19, 2021, which is a divisional of application Ser. No. 14/203,638, filed Mar. 11, 2014, issued as U.S. Pat. No. 10,189,023 on Jan. 29, 2019, which claims priority of U.S. Provisional Application Ser. No. 61/778,727, filed Mar. 13, 2013 and 61/775,860, filed Mar. 11, 2013, respectively, the disclosures of each are incorporated herein by reference in its entirety.

STATEMENT REGARDING FEDERALLY SPONSORED RESEARCH

This invention was made with government support under 5R44CA130391-04 awarded by the National Institutes of Health. The government has certain rights in the invention.

INCORPORATION BY REFERENCE OF SEQUENCE LISTING

The Sequence Listing in the ASCII text file, named as 0076_0023US3_SL.txt, having a size of 9.53 KB, created on Sep. 16, 2021, and submitted to the United States Patent and Trademark Office via EFS-Web, is incorporated herein by reference.

FIELD OF THE INVENTION

Improved methods and products for conducting binding assays are provided. These methods include the use of a linking agent complex that enables the user to configure an assay to meet his/her needs from a standard set of assay materials. The products and methods of the invention greatly enhance productivity and flexibility in assay development.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

Commercially available assays are generally supplied in a pre-set configuration, offering the user little or no flexibility to evaluate target(s) that may be of unique interest to him or her. Such commercial panels may include target analytes that are of little or no interest and/or they may not include the desired target analyte(s). Therefore, there is a need to provide the user a flexible method to configure a user-defined multiplexed assay using a standard set of assay materials and methods.

SUMMARY OF THE INVENTION

The present invention contemplates the following specific embodiments. Various modifications, additions and alterations may be made to embodiments described herein by one skilled in the art without departing from the spirit and scope of the invention. Such modifications, additions, and alterations are intended to fall within the scope of the claims.

Embodiment (1): a method of conducting a multiplexed binding assay for a plurality of analytes of interest comprising:

combining, in one or more steps, the following components: a sample comprising a first analyte of interest and a second analyte of interest, a first targeting agent immobilized on a first binding domain, a first targeting agent complement connected to a linking agent, wherein the first targeting agent complement is a binding partner of the first targeting agent, a first binding reagent connected to a supplemental linking agent, wherein the first binding reagent is a binding partner of the first analyte, a second targeting agent immobilized on a second binding domain, a second targeting agent complement connected to a linking agent, wherein the second targeting agent complement is a binding partner of the second targeting agent, a second binding reagent connected to a supplemental linking agent, wherein the second binding reagent is a binding partner of the second analyte, and optionally, at least two copies of a bridging agent, wherein, if the bridging agent is omitted, each linking agent is a binding partner of the supplemental linking agent, or if the bridging agent is included, the bridging agent has a first binding site for one of the linking agents and an additional binding site for one of the supplemental linking agents;

forming: a first binding complex on the first binding domain comprising the first targeting agent, the first targeting agent complement, the first binding reagent and the first analyte, and a second binding complex on the second binding domain comprising the second targeting agent, the second targeting agent complement, the second binding reagent and the second analyte, and measuring the amount of the first and second analytes on the first and second binding domains, respectively.

In one example of embodiment (1), referred to as embodiment (1)(a), the sample contains one or more additional analytes of interest and for each additional analyte of interest, the combining step further comprises combining, in one or more steps, an additional targeting agent immobilized on an additional binding domain, an additional targeting agent complement connected to a linking agent, and an additional binding reagent connected to a supplemental linking agent, and an additional binding complex on the additional binding domain comprising the additional targeting agent, the additional targeting agent complement, the additional binding reagent and the additional analyte; the forming step further comprises forming an additional binding complex on the additional binding domain comprising the additional targeting agent, the additional targeting agent complement, the additional binding reagent and the additional analyte; and the measurement further comprises measuring the amount of the additional analyte on the additional binding domain.

In a further example of embodiment (1), referred to as embodiment (1)(b), the first targeting agent complement and the first binding reagent are provided as a pre-bound first targeting complex comprising the first targeting agent complement and the first binding reagent linked through a binding interaction between the linking agent and supplemental linking agent; and the second targeting agent complement and the second binding reagent are provided as a pre-bound second targeting complex comprising the second targeting agent complement and the second binding reagent linked through a binding interaction between the linking agent and supplemental linking agent.

Moreover, in another example of embodiment (1), referred to as embodiment (1)(c), the first targeting complex is provided pre-bound to the first targeting agent immobilized on the first binding domain; and the second targeting complex is provided pre-bound to the second targeting agent immobilized on the second binding domain. In this example, combining step further includes: combining the first and second targeting complexes with the sample to form a mixture thereof, binding the first analyte to the first binding reagent in the first targeting complex and binding the second analyte to the second binding reagent in the second targeting complex, contacting a mixture of the first and second targeting complexes bound to first and second analytes, respectively, with the first and second binding domains; and binding the first targeting complex to the first targeting agent on the first binding domain and binding the second targeting complex to the second targeting agent on the second binding domain.

In particular example of embodiment (1), referred to as embodiment (1)(d), the combining step further includes combining, in a first volume of liquid, said first targeting agent complement, said first binding reagent and, if used, said bridging reagent and linking said first targeting agent complement and said first binding reagent through their attached linking agents to form a first targeting complex; and combining, in a second volume of liquid, said second targeting agent complement, said second binding reagent and, if used, said bridging reagent and linking said second targeting agent complex complement and said second binding reagent through their attached linking agents to form a second targeting complex.

In a specific example of embodiment (1), referred to as embodiment (1)(e), the combining step further includes combining said first and second targeting complexes, contacting the combination of said first and second targeting complexes with said first and second binding domains, and binding said first targeting complex to said first targeting agent on said first binding domain and binding said second targeting complex to said second targeting agent on said second binding domain. In this example, the combining step further includes: combining the first and second targeting complexes with the sample to form a mixture thereof, binding the first analyte to the first binding reagent in the first targeting complex and binding the second analyte to the second binding reagent in the second targeting complex, contacting a mixture of the first and second targeting complexes bound to first and second analytes, respectively, with the first and second binding domains; and binding the first targeting complex to the first targeting agent on the first binding domain and binding the second targeting complex to the second targeting agent on the second binding domain.

In embodiments (1)(c) and (1)(e), the first and second targeting complexes can be combined with the sample prior to contacting the first and second targeting complexes with the first and second binding domains. Moreover, in these specific embodiments, the first and second targeting complexes can be combined with the sample after contacting the first and second targeting complexes with the first and second binding domains; or the first and second targeting complexes can be combined with the sample and contacted with the first and second binding domains at the same time.

In embodiment (1)(d), the combining step can further include the steps of: contacting said first and second targeting complexes on said first and second binding domains with said sample, binding said first analyte to the first binding reagent in said first targeting complex and binding said second analyte to said second binding reagent in said second targeting complex.

In embodiments (1) and (1)(a)-(e), the bridging agent can be omitted and the linking agent can be bound to the supplemental linking agent through a binding interaction between (a) a thiol group and a maleimide or iodoacetamide groups; (b) an aldehyde and a hydrazide; or (c) an alkyne and an azide.

In embodiments (1) and (1)(a)-(e), the bridging agent can be omitted and (a) the linking agent is biotin and supplemental linking agent is streptavidin or avidin; (b) the linking agent is streptavidin or avidin and the supplemental linking agent is biotin; (c) the linking agent is a peptide and the supplemental linking agent is an anti-peptide antibody; or (d) the linking agent is an anti-peptide antibody and the supplemental linking agent is a peptide.

Alternatively or additionally, in embodiments (1) and (1)(a)-(e), the bridging agent can be included, the bridging agent can be streptavidin or avidin, and the linking agents and the supplemental linking agents can each comprise biotin.

The first and second binding reagents referenced in embodiments (1) and (1)(a)-(e), each can comprise a receptor, ligand, antibody, hapten, antigen, epitope, mimitope, aptamer, or an intercalater capable of binding to said first and second analytes, respectively. For example, the first and second binding reagents are antigens. Alternatively or additionally, the first and second binding reagents are antibodies.

In embodiments (1) and (1)(a)-(e), the method can include conducting a sandwich binding assay.

In one specific example of embodiments (1) and (1)(a)-(e), the components combined in the combining step further comprise a first detection reagent that binds the first analyte and a second detection reagent that binds the second analyte, and the first and second complexes formed in the second step further comprise the first and second detection reagents, respectively. For example, the first and second detection reagents each comprise a detectable label. In another example of this embodiment, the first and second binding reagents and the first and second detection reagents are antibodies. Moreover, the first and second detection reagents can bind to either the first or second analyte, and optionally, the first and second detection reagents each comprise a detectable label. In a specific example, the first and second binding reagents are antigens, the analytes are antibodies against the antigens and the detection reagents comprise anti-immunoglobulin antibodies, protein A, protein G or protein L.

The method of embodiments (1) and (1)(a)-(e), can include conducting a competitive binding assay.

Still further, the components combined in embodiments (1) and (1)(a)-(e), can further comprise a first detection reagent that competes with the first analyte for binding to the first binding reagent and a second detection reagent that competes with the second analyte for binding to the second binding reagent.

In embodiments (1) and (1)(a)-(e), one or more of the following additional elements of the method are included: the first and second detection reagents can comprise detectable labels; the first and second binding reagents are antibodies and the first and second detection reagents are structural analogs of the analytes; the measuring step can comprise measuring the presence of the first and second detectable labels via optical absorbance, fluorescence, phosphorescence, chemiluminescence, electrochemiluminescence, light scattering, or magnetism; the first and second detectable label is an electrochemiluminescent label and the measuring step further comprises measuring an electrochemiluminescent signal and correlating the signal with an amount of first and second analyte in the sample; the first and second binding domains are positioned on an electrode and the measuring step further comprises applying a voltage waveform to the electrode to generate electrochemiluminescence; each of the first and second binding domains is an element of an array of binding domains, and optionally, the array is located within a well of a multi-well plate; each of the first and second binding domains are each positioned on a surface of one or more microparticles, and optionally, the particles are coded to allow for identification of specific particles and discrimination between the first and second binding domains.

Embodiment (1)(f): includes the elements of embodiment (1) and one or more additional features of embodiment (1)(a)-(e), wherein the first targeting agent and first targeting agent complement and the second targeting agent and second targeting agent complement each comprise a complementary oligonucleotide pair. In this specific example, the first and second binding reagents can each be antibodies. Moreover, in this specific example, the complementary oligonucleotide pair positioned on each of the first and second binding domains is different and selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |

6

-continued

| pair # | Sequence (5'-3') |
|---|---|
| 14 | cttacaacgcca (SEQ ID NO: 27)<br>tggcgttgtaag (SEQ ID NO: 28) |
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 19 | ggtcgtgtttca (SEQ ID NO: 37)<br>tgaaacacgacc (SEQ ID NO: 38) |
| 20 | gttgattctgtc (SEQ ID NO: 39)<br>gacagaatcaac (SEQ ID NO: 40) |
| 21 | tacccggaataa (SEQ ID NO: 41)<br>ttattccgggta (SEQ ID NO: 42) |
| 22 | tgcttgacttgg (SEQ ID NO: 43)<br>ccaagtcaagca (SEQ ID NO: 44) |
| 23 | ttccacttaggg (SEQ ID NO: 45)<br>ccctaagtggaa (SEQ ID NO: 46) |
| 24 | ttgtctagcggc (SEQ ID NO: 47)<br>gccgctagacaa (SEQ ID NO: 48) |
| 25 | tttcccttgcta (SEQ ID NO: 49)<br>tagcaagggaaa (SEQ ID NO: 50) |

Embodiment (1)(g): includes the elements of embodiment (1) and one or more additional features of embodiment (1)(a)-(e), wherein the first targeting agent and first targeting agent complement and the second targeting agent and second targeting agent complement each comprise a complementary oligonucleotide pair. In this specific example, the first and second binding reagents can each be antibodies. Moreover, in this specific example, the complementary oligonucleotide pair positioned on each of the first and second binding domains is different and selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |

7

-continued

| Pair | Sequence |
|------|----------|
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

In embodiments (1)(f) and/or (1)(g), there are at least 7 binding domains, or at least 10 binding domains; or at least 16 binding domains; or at least 25 binding domains.

In embodiments (1) and (1)(a), each of the first and second complementary targeting agents can selectively bind to one of the first and second binding domains, respectively. For example, the cross-reactivity for binding of the complementary targeting agent to other binding domains is less than 5% of the binding to the one of the binding domains; or the cross-reactivity for binding of each first and second complementary targeting agent to a third binding domain is less than 1% of the binding to the one of the binding domains; or the cross-reactivity for binding of each first and second complementary targeting agent to a third binding domain is less than 0.5% of the binding to the one of the binding domains; or the cross-reactivity for binding of each first and second complementary targeting agent to a third binding domain is less than 0.1% of the binding to the one of the binding domains.

In embodiments (1) and (1)(a), the first and second binding reagents can each bind different analytes of interest; or the first and second binding reagents are each preferentially selective for a different analyte of interest.

The first and second binding reagents of any one of the foregoing embodiments can differ in the affinity and/or selectivity for different analytes of interest, e.g., the cross-reactivity of the first analyte to the second binding reagent is less than 5% of the binding to the first binding reagent, or the cross-reactivity of the first analyte to the second binding reagent is less than 1% of the binding to the first binding reagent, or the cross-reactivity of the first analyte to the second binding reagent is less than 0.5% of the binding to the first binding reagent, or the cross-reactivity of the first analyte to the second binding reagent is less than 0.1% of the binding to the first binding reagent, or the observed cross-reactivity of an analyte of interest for non-specific binding reagents is less than 5% of the binding to the binding reagent selected for binding to that analyte, or the observed cross-reactivity of an analyte of interest for non-specific binding reagents is less than 1% of the binding to the binding reagent selected for binding to that analyte, or the observed cross-reactivity of an analyte of interest for non-specific binding reagents is less than 0.5% of the binding to the binding reagent selected for binding to that analyte, or the observed cross-reactivity of an analyte of interest for non-specific binding reagents is less than 0.1% of the binding to the binding reagent selected for binding to that analyte. Still further in this specific example of the foregoing embodiments, the cross-reactivity of the first analyte to a binding reagent located in the second binding domain is less than 5% of the binding to a binding reagent located in the first binding domain, or the cross-reactivity of the first analyte to a binding reagent located in the second binding domain is less than 1% of the binding to a binding reagent located in the first binding domain, or the cross-reactivity of the first analyte to a binding reagent located in the second binding domain is less than 0.5% of the binding to a binding reagent located in the first binding domain, or the cross-reactivity of the first analyte to a binding reagent located in the second binding domain is less than 0.1% of the binding to a binding reagent located in the first binding domain, or the observed cross-reactivity of an analyte of interest for binding reagents located in a non-specific binding domain is less than 5% of the binding to the binding reagents in the binding domain assigned to that analyte, or the observed cross-reactivity of an analyte of interest for binding reagents located in a non-specific binding domain is less than 1% of the binding to the binding reagents in the binding domain assigned to that analyte, or the observed cross-reactivity of an analyte of interest for binding reagents located in a non-specific binding domain is less than 0.5% of the binding to the binding reagents in the binding domain assigned to that analyte, or the observed cross-reactivity of an analyte of interest for binding reagents located in a non-specific binding domain is less than 0.1% of the binding to the binding reagents in the binding domain assigned to that analyte.

In embodiments (1) and (1)(a), the first and second targeting agents and first and second targeting agent complements, respectively, can be used to map a set of binding reagents to a set of binding domains and each of the binding reagents in the set bind to a different analyte of interest. For example, each of the binding reagents in the set is preferentially selective for a different analyte of interest, or each of the binding reagents in the set differ in the affinity and/or selectivity for different analytes of interest.

Embodiment (2): an oligonucleotide selected from:

| | |
|---|---|
| acatcggtagtt | (SEQ ID NO: 1) |
| aactaccgatgt | (SEQ ID NO: 2) |
| acgtcccagttg | (SEQ ID NO: 3) |
| caactgggacgt | (SEQ ID NO: 4) |
| agaagaagatcc | (SEQ ID NO: 5) |
| ggatcttcttct | (SEQ ID NO: 6) |
| aggttcagtgca | (SEQ ID NO: 7) |
| tgcactgaacct | (SEQ ID NO: 8) |
| atcaggatacgc | (SEQ ID NO: 9) |
| gcgtatcctgat | (SEQ ID NO: 10) |
| atcattaccacc | (SEQ ID NO: 11) |
| ggtggtaatgat | (SEQ ID NO: 12) |
| attaacgggagc | (SEQ ID NO: 13) |
| gctcccgttaat | (SEQ ID NO: 14) |

-continued cagaggtcttaa (SEQ ID NO: 15)

ttaagacctctg (SEQ ID NO: 16)

caggtgtccatt (SEQ ID NO: 17)

aatggacacctg (SEQ ID NO: 18)

catccaatccag (SEQ ID NO: 19)

ctggattggatg (SEQ ID NO: 20)

cctacgatatac (SEQ ID NO: 21)

gtatatcgtagg (SEQ ID NO: 22)

cgaatgtagagt (SEQ ID NO: 23)

actctacattcg (SEQ ID NO: 24)

cggtttgagata (SEQ ID NO: 25)

tatctcaaaccg (SEQ ID NO: 26)

cttacaacgcca (SEQ ID NO: 27)

tggcgttgtaag (SEQ ID NO: 28)

ctttctcggcac (SEQ ID NO: 29)

gtgccgagaaag (SEQ ID NO: 30)

gacataaagcga (SEQ ID NO: 31)

tcgctttatgtc (SEQ ID NO: 32)

gccatagtctct (SEQ ID NO: 33)

agagactatggc (SEQ ID NO: 34)

gctaattcacca (SEQ ID NO: 35)

tggtgaattagc (SEQ ID NO: 36)

ggtcgtgtttca (SEQ ID NO: 37)

tgaaacacgacc (SEQ ID NO: 38)

gttgattctgtc (SEQ ID NO: 39)

gacagaatcaac (SEQ ID NO: 40)

tacccggaataa (SEQ ID NO: 41)

ttattccgggta (SEQ ID NO: 42)

tgcttgacttgg (SEQ ID NO: 43)

ccaagtcaagca (SEQ ID NO: 44)

ttccacttaggg (SEQ ID NO: 45)

ccctaagtggaa (SEQ ID NO: 46)

ttgtctagcggc (SEQ ID NO: 47)

gccgctagacaa (SEQ ID NO: 48)

tttcccttgcta (SEQ ID NO: 49)

tagcaagggaaa (SEQ ID NO: 50)

Embodiment (3): an oligonucleotide selected from:

| Pair | Sequence |
|---|---|
| 1 | acatcggtagtt (SEQ ID NO: 1) |
|  | aactaccgatgt (SEQ ID NO: 2) |
| 3 | agaagaagatcc (SEQ ID NO: 5) |
|  | ggatcttcttct (SEQ ID NO: 6) |
| 6 | atcattaccacc (SEQ ID NO: 11) |
|  | ggtggtaatgat (SEQ ID NO: 12) |
| 7 | attaacgggagc (SEQ ID NO: 13) |
|  | gctcccgttaat (SEQ ID NO: 14) |
| 8 | cagaggtcttaa (SEQ ID NO: 15) |
|  | ttaagacctctg (SEQ ID NO: 16) |
| 9 | caggtgtccatt (SEQ ID NO: 17) |
|  | aatggacacctg (SEQ ID NO: 18) |
| 11 | cctacgatatac (SEQ ID NO: 21) |
|  | gtatatcgtagg (SEQ ID NO: 22) |
| 12 | cgaatgtagagt (SEQ ID NO: 23) |
|  | actctacattcg (SEQ ID NO: 24) |
| 13 | cggtttgagata (SEQ ID NO: 25) |
|  | tatctcaaaccg (SEQ ID NO: 26) |
| 16 | gacataaagcga (SEQ ID NO: 31) |
|  | tcgctttatgtc (SEQ ID NO: 32) |
| 17 | gccatagtctct (SEQ ID NO: 33) |
|  | agagactatggc (SEQ ID NO: 34) |
| 18 | gctaattcacca (SEQ ID NO: 35) |
|  | tggtgaattagc (SEQ ID NO: 36) |
| 20 | gttgattctgtc (SEQ ID NO: 39) |
|  | gacagaatcaac (SEQ ID NO: 40) |
| 23 | ttccacttaggg (SEQ ID NO: 45) |
|  | ccctaagtggaa (SEQ ID NO: 46) |
| 25 | tttcccttgcta (SEQ ID NO: 49) |
|  | tagcaagggaaa (SEQ ID NO: 50) |

Embodiment (4): a kit comprising, in separate vials, at least 4 oligonucleotides, each comprising a different sequence selected from:

acatcggtagtt (SEQ ID NO: 1)

aactaccgatgt (SEQ ID NO: 2)

acgtcccagttg (SEQ ID NO: 3)

caactgggacgt (SEQ ID NO: 4)

agaagaagatcc (SEQ ID NO: 5)

ggatcttcttct (SEQ ID NO: 6)

aggttcagtgca (SEQ ID NO: 7)

tgcactgaacct (SEQ ID NO: 8)

atcaggatacgc (SEQ ID NO: 9)

gcgtatcctgat (SEQ ID NO: 10)

atcattaccacc (SEQ ID NO: 11)

ggtggtaatgat (SEQ ID NO: 12)

-continued

```
attaacgggagc    (SEQ ID NO: 13)

gctcccgttaat    (SEQ ID NO: 14)

cagaggtcttaa    (SEQ ID NO: 15)

ttaagacctctg    (SEQ ID NO: 16)

caggtgtccatt    (SEQ ID NO: 17)

aatggacacctg    (SEQ ID NO: 18)

catccaatccag    (SEQ ID NO: 19)

ctggattggatg    (SEQ ID NO: 20)

cctacgatatac    (SEQ ID NO: 21)

gtatatcgtagg    (SEQ ID NO: 22)

cgaatgtagagt    (SEQ ID NO: 23)

actctacattcg    (SEQ ID NO: 24)

cggtttgagata    (SEQ ID NO: 25)

tatctcaaaccg    (SEQ ID NO: 26)

cttacaacgcca    (SEQ ID NO: 27)

tggcgttgtaag    (SEQ ID NO: 28)

ctttctcggcac    (SEQ ID NO: 29)

gtgccgagaaag    (SEQ ID NO: 30)

gacataaagcga    (SEQ ID NO: 31)

tcgctttatgtc    (SEQ ID NO: 32)

gccatagtctct    (SEQ ID NO: 33)

agagactatggc    (SEQ ID NO: 34)

gctaattcacca    (SEQ ID NO: 35)

tggtgaattagc    (SEQ ID NO: 36)

ggtcgtgtttca    (SEQ ID NO: 37)

tgaaacacgacc    (SEQ ID NO: 38)

gttgattctgtc    (SEQ ID NO: 39)

gacagaatcaac    (SEQ ID NO: 40)

tacccggaataa    (SEQ ID NO: 41)

ttattccgggta    (SEQ ID NO: 42)

tgcttgacttgg    (SEQ ID NO: 43)

ccaagtcaagca    (SEQ ID NO: 44)

ttccacttaggg    (SEQ ID NO: 45)

ccctaagtggaa    (SEQ ID NO: 46)

ttgtctagcggc    (SEQ ID NO: 47)

gccgctagacaa    (SEQ ID NO: 48)

tttcccttgcta    (SEQ ID NO: 49)

tagcaagggaaa    (SEQ ID NO: 50)
```

Embodiment (5): a kit comprising, in separate vials, at least 4 oligonucleotides, each comprising a different sequence selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

In the kit of embodiments (4) and (5), the kit can comprise at least 7 oligonucleotides, or at least 10 oligonucleotides, or at least 16 oligonucleotides, or at least 25 oligonucleotides. Moreover, each of the oligonucleotides of these specific embodiments can be modified with a linking agent comprising a biotin, streptavidin, avidin, amino group, thiol group, aldehyde group, hydrazide group, azide group, alkyne group, maleimide group or iodoacetamide group. In another specific example of embodiments (4) and (5), each of the at least 4 oligonucleotides can be coupled to a different antibody, and optionally, each different sequence is not a complement of an additional different sequence of the at least 4 oligonucleotides.

Embodiment (6): a mixture comprising at least 4 oligonucleotides, each comprising a different sequence selected from:

```
acatcggtagtt    (SEQ ID NO: 1)

aactaccgatgt    (SEQ ID NO: 2)

acgtcccagttg    (SEQ ID NO: 3)

caactgggacgt    (SEQ ID NO: 4)

agaagaagatcc    (SEQ ID NO: 5)
```

-continued

```
ggatcttcttct (SEQ ID NO: 6)

aggttcagtgca (SEQ ID NO: 7)

tgcactgaacct (SEQ ID NO: 8)

atcaggatacgc (SEQ ID NO: 9)

gcgtatcctgat (SEQ ID NO: 10)

atcattaccacc (SEQ ID NO: 11)

ggtggtaatgat (SEQ ID NO: 12)

attaacgggagc (SEQ ID NO: 13)

gctcccgttaat (SEQ ID NO: 14)

cagaggtcttaa (SEQ ID NO: 15)

ttaagacctctg (SEQ ID NO: 16)

caggtgtccatt (SEQ ID NO: 17)

aatggacacctg (SEQ ID NO: 18)

catccaatccag (SEQ ID NO: 19)

ctggattggatg (SEQ ID NO: 20)

cctacgatatac (SEQ ID NO: 21)

gtatatcgtagg (SEQ ID NO: 22)

cgaatgtagagt (SEQ ID NO: 23)

actctacattcg (SEQ ID NO: 24)

cggtttgagata (SEQ ID NO: 25)

tatctcaaaccg (SEQ ID NO: 26)

cttacaacgcca (SEQ ID NO: 27)

tggcgttgtaag (SEQ ID NO: 28)

ctttctcggcac (SEQ ID NO: 29)

gtgccgagaaag (SEQ ID NO: 30)

gacataaagcga (SEQ ID NO: 31)

tcgctttatgtc (SEQ ID NO: 32)

gccatagtctct (SEQ ID NO: 33)

agagactatggc (SEQ ID NO: 34)

gctaattcacca (SEQ ID NO: 35)

tggtgaattagc (SEQ ID NO: 36)

ggtcgtgtttca (SEQ ID NO: 37)

tgaaacacgacc (SEQ ID NO: 38)

gttgattctgtc (SEQ ID NO: 39)

gacagaatcaac (SEQ ID NO: 40)

tacccggaataa (SEQ ID NO: 41)

ttattccgggta (SEQ ID NO: 42)

tgcttgacttgg (SEQ ID NO: 43)

ccaagtcaagca (SEQ ID NO: 44)

ttccacttaggg (SEQ ID NO: 45)
```

-continued

```
ccctaagtggaa (SEQ ID NO: 46)

ttgtctagcggc (SEQ ID NO: 47)

gccgctagacaa (SEQ ID NO: 48)

tttcccttgcta (SEQ ID NO: 49)

tagcaagggaaa (SEQ ID NO: 50)
``` wherein each of the different sequences are coupled to a different antibody.

Embodiment (7): a mixture comprising at least 4 oligo-nucleotides, each comprising a different sequence selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) | wherein each of the different sequences are coupled to a different antibody.

In embodiments (6) and (7), the mixture can include at least 7 oligonucleotides, or at least 10 oligonucleotides; or at least 16 oligonucleotides; or at least 25 oligonucleotides. Moreover, in a specific example of embodiments (6) and (7), each different sequence is not a complement of an additional different sequence of the at least 4 oligonucleotides.

Embodiment (8): an array comprising a plurality of at least 4 binding domains, wherein one or more, and optionally, each binding domain has immobilized thereon a different oligonucleotide sequence selected from:

```
acatcggtagtt  (SEQ ID NO: 1)

aactaccgatgt  (SEQ ID NO: 2)

acgtcccagttg  (SEQ ID NO: 3)

caactgggacgt  (SEQ ID NO: 4)

agaagaagatcc  (SEQ ID NO: 5)

ggatcttcttct  (SEQ ID NO: 6)

aggttcagtgca  (SEQ ID NO: 7)

tgcactgaacct  (SEQ ID NO: 8)

atcaggatacgc  (SEQ ID NO: 9)

gcgtatcctgat  (SEQ ID NO: 10)

atcattaccacc  (SEQ ID NO: 11)

ggtggtaatgat  (SEQ ID NO: 12)

attaacgggagc  (SEQ ID NO: 13)

gctcccgttaat  (SEQ ID NO: 14)

cagaggtcttaa  (SEQ ID NO: 15)

ttaagacctctg  (SEQ ID NO: 16)

caggtgtccatt  (SEQ ID NO: 17)

aatggacacctg  (SEQ ID NO: 18)

catccaatccag  (SEQ ID NO: 19)

ctggattggatg  (SEQ ID NO: 20)

cctacgatatac  (SEQ ID NO: 21)

gtatatcgtagg  (SEQ ID NO: 22)

cgaatgtagagt  (SEQ ID NO: 23)

actctacattcg  (SEQ ID NO: 24)

cggtttgagata  (SEQ ID NO: 25)

tatctcaaaccg  (SEQ ID NO: 26)

cttacaacgcca  (SEQ ID NO: 27)

tggcgttgtaag  (SEQ ID NO: 28)

ctttctcggcac  (SEQ ID NO: 29)

gtgccgagaaag  (SEQ ID NO: 30)

gacataaagcga  (SEQ ID NO: 31)

tcgctttatgtc  (SEQ ID NO: 32)

gccatagtctct  (SEQ ID NO: 33)

agagactatggc  (SEQ ID NO: 34)

gctaattcacca  (SEQ ID NO: 35)

tggtgaattagc  (SEQ ID NO: 36)

ggtcgtgtttca  (SEQ ID NO: 37)

tgaaacacgacc  (SEQ ID NO: 38)

gttgattctgtc  (SEQ ID NO: 39)
```

-continued

```
gacagaatcaac  (SEQ ID NO: 40)

tacccggaataa  (SEQ ID NO: 41)

ttattccgggta  (SEQ ID NO: 42)

tgcttgacttgg  (SEQ ID NO: 43)

ccaagtcaagca  (SEQ ID NO: 44)

ttccacttaggg  (SEQ ID NO: 45)

ccctaagtggaa  (SEQ ID NO: 46)

ttgtctagcggc  (SEQ ID NO: 47)

gccgctagacaa  (SEQ ID NO: 48)

tttcccttgcta  (SEQ ID NO: 49)

tagcaagggaaa  (SEQ ID NO: 50)
```

Embodiment (9): an array comprising a plurality of at least 4 binding domains, wherein one or more and optionally, each binding domain has immobilized thereon a different oligonucleotide sequence selected from:

| Pair | Sequence | |
|---|---|---|
| 1 | acatcggtagtt | (SEQ ID NO: 1) |
| | aactaccgatgt | (SEQ ID NO: 2) |
| 3 | agaagaagatcc | (SEQ ID NO: 5) |
| | ggatcttcttct | (SEQ ID NO: 6) |
| 6 | atcattaccacc | (SEQ ID NO: 11) |
| | ggtggtaatgat | (SEQ ID NO: 12) |
| 7 | attaacgggagc | (SEQ ID NO: 13) |
| | gctcccgttaat | (SEQ ID NO: 14) |
| 8 | cagaggtcttaa | (SEQ ID NO: 15) |
| | ttaagacctctg | (SEQ ID NO: 16) |
| 9 | caggtgtccatt | (SEQ ID NO: 17) |
| | aatggacacctg | (SEQ ID NO: 18) |
| 11 | cctacgatatac | (SEQ ID NO: 21) |
| | gtatatcgtagg | (SEQ ID NO: 22) |
| 12 | cgaatgtagagt | (SEQ ID NO: 23) |
| | actctacattcg | (SEQ ID NO: 24) |
| 13 | cggtttgagata | (SEQ ID NO: 25) |
| | tatctcaaaccg | (SEQ ID NO: 26) |
| 16 | gacataaagcga | (SEQ ID NO: 31) |
| | tcgctttatgtc | (SEQ ID NO: 32) |
| 17 | gccatagtctct | (SEQ ID NO: 33) |
| | agagactatggc | (SEQ ID NO: 34) |
| 18 | gctaattcacca | (SEQ ID NO: 35) |
| | tggtgaattagc | (SEQ ID NO: 36) |
| 20 | gttgattctgtc | (SEQ ID NO: 39) |
| | gacagaatcaac | (SEQ ID NO: 40) |
| 23 | ttccacttaggg | (SEQ ID NO: 45) |
| | ccctaagtggaa | (SEQ ID NO: 46) |
| 25 | tttcccttgcta | (SEQ ID NO: 49) |
| | tagcaagggaaa | (SEQ ID NO: 50) |

In embodiments (8) and (9), the array can comprise at least 7 binding domains, or at least 10 binding domains, or at least 16 binding domains, or at least 25 binding domains, and optionally, each different sequence is not a complement of an additional different sequence of the at least 4 oligo-nucleotides Embodiment (10): a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from:

```
acatcggtagtt (SEQ ID NO: 1)

aactaccgatgt (SEQ ID NO: 2)

acgtcccagttg (SEQ ID NO: 3)

caactgggacgt (SEQ ID NO: 4)

agaagaagatcc (SEQ ID NO: 5)

ggatcttcttct (SEQ ID NO: 6)

aggttcagtgca (SEQ ID NO: 7)

tgcactgaacct (SEQ ID NO: 8)

atcaggatacgc (SEQ ID NO: 9)

gcgtatcctgat (SEQ ID NO: 10)

atcattaccacc (SEQ ID NO: 11)

ggtggtaatgat (SEQ ID NO: 12)

attaacgggagc (SEQ ID NO: 13)

gctcccgttaat (SEQ ID NO: 14)

cagaggtcttaa (SEQ ID NO: 15)

ttaagacctctg (SEQ ID NO: 16)

caggtgtccatt (SEQ ID NO: 17)

aatggacacctg (SEQ ID NO: 18)

catccaatccag (SEQ ID NO: 19)

ctggattggatg (SEQ ID NO: 20)

cctacgatatac (SEQ ID NO: 21)

gtatatcgtagg (SEQ ID NO: 22)

cgaatgtagagt (SEQ ID NO: 23)

actctacattcg (SEQ ID NO: 24)

cggtttgagata (SEQ ID NO: 25)

tatctcaaaccg (SEQ ID NO: 26)

cttacaacgcca (SEQ ID NO: 27)

tggcgttgtaag (SEQ ID NO: 28)

ctttctcggcac (SEQ ID NO: 29)

gtgccgagaaag (SEQ ID NO: 30)

gacataaagcga (SEQ ID NO: 31)

tcgctttatgtc (SEQ ID NO: 32)

gccatagtctct (SEQ ID NO: 33)

agagactatggc (SEQ ID NO: 34)
```

-continued

```
gctaattcacca (SEQ ID NO: 35)

tggtgaattagc (SEQ ID NO: 36)

ggtcgtgtttca (SEQ ID NO: 37)

tgaaacacgacc (SEQ ID NO: 38)

gttgattctgtc (SEQ ID NO: 39)

gacagaatcaac (SEQ ID NO: 40)

tacccggaataa (SEQ ID NO: 41)

ttattccgggta (SEQ ID NO: 42)

tgcttgacttgg (SEQ ID NO: 43)

ccaagtcaagca (SEQ ID NO: 44)

ttccacttaggg (SEQ ID NO: 45)

ccctaagtggaa (SEQ ID NO: 46)

ttgtctagcggc (SEQ ID NO: 47)

gccgctagacaa (SEQ ID NO: 48)

tttcccttgcta (SEQ ID NO: 49)

tagcaagggaaa (SEQ ID NO: 50)
```

Embodiment (11): a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from:

| Pair | Sequence |
|------|----------|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |

-continued

| Pair | Sequence |
|------|----------|
| 17 | gccatagtctct (SEQ ID NO: 33) |
|    | agagactatggc (SEQ ID NO: 34) |
| 18 | gctaattcacca (SEQ ID NO: 35) |
|    | tggtgaattagc (SEQ ID NO: 36) |
| 20 | gttgattctgtc (SEQ ID NO: 39) |
|    | gacagaatcaac (SEQ ID NO: 40) |
| 23 | ttccacttaggg (SEQ ID NO: 45) |
|    | ccctaagtggaa (SEQ ID NO: 46) |
| 25 | tttcccttgcta (SEQ ID NO: 49) |
|    | tagcaagggaaa (SEQ ID NO: 50) |

The plate of embodiments (10) and (11) can include at least 24 wells, or at least 96 wells, or at least 384 wells, and/or optionally, the array comprises at least 7 oligonucleotides, or at least 10 oligonucleotides, or at least 16 oligonucleotides, or at least 25 oligonucleotides, wherein optionally, each different sequence is not a complement of an additional different sequence of the at least 4 oligonucleotides Embodiment (12): a kit comprising a set of at least 4 microparticle reagents, in one or more vials, wherein each microparticle reagent of the set comprises a microparticle having immobilized thereon a different oligonucleotide sequence selected from:

| | |
|---|---|
| acatcggtagtt | (SEQ ID NO: 1) |
| aactaccgatgt | (SEQ ID NO: 2) |
| acgtcccagttg | (SEQ ID NO: 3) |
| caactgggacgt | (SEQ ID NO: 4) |
| agaagaagatcc | (SEQ ID NO: 5) |
| ggatcttcttct | (SEQ ID NO: 6) |
| aggttcagtgca | (SEQ ID NO: 7) |
| tgcactgaacct | (SEQ ID NO: 8) |
| atcaggatacgc | (SEQ ID NO: 9) |
| gcgtatcctgat | (SEQ ID NO: 10) |
| atcattaccacc | (SEQ ID NO: 11) |
| ggtggtaatgat | (SEQ ID NO: 12) |
| attaacgggagc | (SEQ ID NO: 13) |
| gctcccgttaat | (SEQ ID NO: 14) |
| cagaggtcttaa | (SEQ ID NO: 15) |
| ttaagacctctg | (SEQ ID NO: 16) |
| caggtgtccatt | (SEQ ID NO: 17) |
| aatggacacctg | (SEQ ID NO: 18) |
| catccaatccag | (SEQ ID NO: 19) |
| ctggattggatg | (SEQ ID NO: 20) |
| cctacgatatac | (SEQ ID NO: 21) |
| gtatatcgtagg | (SEQ ID NO: 22) |

-continued

| | |
|---|---|
| cgaatgtagagt | (SEQ ID NO: 23) |
| actctacattcg | (SEQ ID NO: 24) |
| cggtttgagata | (SEQ ID NO: 25) |
| tatctcaaaccg | (SEQ ID NO: 26) |
| cttacaacgcca | (SEQ ID NO: 27) |
| tggcgttgtaag | (SEQ ID NO: 28) |
| ctttctcggcac | (SEQ ID NO: 29) |
| gtgccgagaaag | (SEQ ID NO: 30) |
| gacataaagcga | (SEQ ID NO: 31) |
| tcgctttatgtc | (SEQ ID NO: 32) |
| gccatagtctct | (SEQ ID NO: 33) |
| agagactatggc | (SEQ ID NO: 34) |
| gctaattcacca | (SEQ ID NO: 35) |
| tggtgaattagc | (SEQ ID NO: 36) |
| ggtcgtgtttca | (SEQ ID NO: 37) |
| tgaaacacgacc | (SEQ ID NO: 38) |
| gttgattctgtc | (SEQ ID NO: 39) |
| gacagaatcaac | (SEQ ID NO: 40) |
| tacccggaataa | (SEQ ID NO: 41) |
| ttattccgggta | (SEQ ID NO: 42) |
| tgcttgacttgg | (SEQ ID NO: 43) |
| ccaagtcaagca | (SEQ ID NO: 44) |
| ttccacttaggg | (SEQ ID NO: 45) |
| ccctaagtggaa | (SEQ ID NO: 46) |
| ttgtctagcggc | (SEQ ID NO: 47) |
| gccgctagacaa | (SEQ ID NO: 48) |
| tttcccttgcta | (SEQ ID NO: 49) |
| tagcaagggaaa | (SEQ ID NO: 50) |

Embodiment (13): a kit comprising a set of at least 4 microparticle reagents, in one or more vials, wherein each microparticle reagent of the set comprises a microparticle having immobilized thereon a different oligonucleotide sequence selected from:

| Pair | Sequence |
|------|----------|
| 1 | acatcggtagtt (SEQ ID NO: 1) |
|   | aactaccgatgt (SEQ ID NO: 2) |
| 3 | agaagaagatcc (SEQ ID NO: 5) |
|   | ggatcttcttct (SEQ ID NO: 6) |
| 6 | atcattaccacc (SEQ ID NO: 11) |
|   | ggtggtaatgat (SEQ ID NO: 12) |
| 7 | attaacgggagc (SEQ ID NO: 13) |
|   | gctcccgttaat (SEQ ID NO: 14) |

-continued

| Pair | Sequence |
|------|----------|
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

The kit of embodiments (12) and (13) can include a set of at least 7 microparticles, or a set of at least 10 microparticles, or a set of at least 16 microparticles, or a set of at least 25 microparticles, and/or optionally, each different sequence is not a complement of an additional different sequence of the at least 4 oligonucleotides.

The microparticles of embodiments (12) and (13) can be coded and the different microparticle reagents can have different identifying codes.

Embodiment (14): a kit comprising a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from:

acatcggtagtt (SEQ ID NO: 1)

aactaccgatgt (SEQ ID NO: 2)

acgtcccagttg (SEQ ID NO: 3)

caactgggacgt (SEQ ID NO: 4)

agaagaagatcc (SEQ ID NO: 5)

ggatcttcttct (SEQ ID NO: 6)

aggttcagtgca (SEQ ID NO: 7)

tgcactgaacct (SEQ ID NO: 8)

atcaggatacgc (SEQ ID NO: 9)

gcgtatcctgat (SEQ ID NO: 10)

-continued atcattaccacc (SEQ ID NO: 11)

ggtggtaatgat (SEQ ID NO: 12)

attaacgggagc (SEQ ID NO: 13)

gctcccgttaat (SEQ ID NO: 14)

cagaggtcttaa (SEQ ID NO: 15)

ttaagacctctg (SEQ ID NO: 16)

caggtgtccatt (SEQ ID NO: 17)

aatggacacctg (SEQ ID NO: 18)

catccaatccag (SEQ ID NO: 19)

ctggattggatg (SEQ ID NO: 20)

cctacgatatac (SEQ ID NO: 21)

gtatatcgtagg (SEQ ID NO: 22)

cgaatgtagagt (SEQ ID NO: 23)

actctacattcg (SEQ ID NO: 24)

cggtttgagata (SEQ ID NO: 25)

tatctcaaaccg (SEQ ID NO: 26)

cttacaacgcca (SEQ ID NO: 27)

tggcgttgtaag (SEQ ID NO: 28)

ctttctcggcac (SEQ ID NO: 29)

gtgccgagaaag (SEQ ID NO: 30)

gacataaagcga (SEQ ID NO: 31)

tcgctttatgtc (SEQ ID NO: 32)

gccatagtctct (SEQ ID NO: 33)

agagactatggc (SEQ ID NO: 34)

gctaattcacca (SEQ ID NO: 35)

tggtgaattagc (SEQ ID NO: 36)

ggtcgtgtttca (SEQ ID NO: 37)

tgaaacacgacc (SEQ ID NO: 38)

gttgattctgtc (SEQ ID NO: 39)

gacagaatcaac (SEQ ID NO: 40)

tacccggaataa (SEQ ID NO: 41)

ttattccgggta (SEQ ID NO: 42)

tgcttgacttgg (SEQ ID NO: 43)

ccaagtcaagca (SEQ ID NO: 44)

ttccacttaggg (SEQ ID NO: 45)

ccctaagtggaa (SEQ ID NO: 46)

ttgtctagcggc (SEQ ID NO: 47)

gccgctagacaa (SEQ ID NO: 48)

-continued

```
tttcccttgcta (SEQ ID NO: 49)

tagcaagggaaa (SEQ ID NO: 50)
``` and
(i) a set of oligonucleotides comprised of two or more oligonucleotides selected from:

```
acatcggtagtt (SEQ ID NO: 1)

aactaccgatgt (SEQ ID NO: 2)

acgtcccagttg (SEQ ID NO: 3)

caactgggacgt (SEQ ID NO: 4)

agaagaagatcc (SEQ ID NO: 5)

ggatcttcttct (SEQ ID NO: 6)

aggttcagtgca (SEQ ID NO: 7)

tgcactgaacct (SEQ ID NO: 8)

atcaggatacgc (SEQ ID NO: 9)

gcgtatcctgat (SEQ ID NO: 10)

atcattaccacc (SEQ ID NO: 11)

ggtggtaatgat (SEQ ID NO: 12)

attaacgggagc (SEQ ID NO: 13)

gctcccgttaat (SEQ ID NO: 14)

cagaggtcttaa (SEQ ID NO: 15)

ttaagacctctg (SEQ ID NO: 16)

caggtgtccatt (SEQ ID NO: 17)

aatggacacctg (SEQ ID NO: 18)

catccaatccag (SEQ ID NO: 19)

ctggattggatg (SEQ ID NO: 20)

cctacgatatac (SEQ ID NO: 21)

gtatatcgtagg (SEQ ID NO: 22)

cgaatgtagagt (SEQ ID NO: 23)

actctacattcg (SEQ ID NO: 24)

cggtttgagata (SEQ ID NO: 25)

tatctcaaaccg (SEQ ID NO: 26)

cttacaacgcca (SEQ ID NO: 27)

tggcgttgtaag (SEQ ID NO: 28)

ctttctcggcac (SEQ ID NO: 29)

gtgccgagaaag (SEQ ID NO: 30)

gacataaagcga (SEQ ID NO: 31)

tcgctttatgtc (SEQ ID NO: 32)

gccatagtctct (SEQ ID NO: 33)

agagactatggc (SEQ ID NO: 34)

gctaattcacca (SEQ ID NO: 35)
```

-continued

```
tggtgaattagc (SEQ ID NO: 36)

ggtcgtgtttca (SEQ ID NO: 37)

tgaaacacgacc (SEQ ID NO: 38)

gttgattctgtc (SEQ ID NO: 39)

gacagaatcaac (SEQ ID NO: 40)

tacccggaataa (SEQ ID NO: 41)

ttattccgggta (SEQ ID NO: 42)

tgcttgacttgg (SEQ ID NO: 43)

ccaagtcaagca (SEQ ID NO: 44)

ttccacttaggg (SEQ ID NO: 45)

ccctaagtggaa (SEQ ID NO: 46)

ttgtctagcggc (SEQ ID NO: 47)

gccgctagacaa (SEQ ID NO: 48)

tttcccttgcta (SEQ ID NO: 49)

tagcaagggaaa (SEQ ID NO: 50)
``` wherein the oligonucleotides in component (ii) are complementary to the oligonucleotides in component (i).

Embodiment (15): a kit comprising a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from:

| Pair | Sequence |
|---|---|
| 1 | acatcggtagtt (SEQ ID NO: 1) |
|  | aactaccgatgt (SEQ ID NO: 2) |
| 3 | agaagaagatcc (SEQ ID NO: 5) |
|  | ggatcttcttct (SEQ ID NO: 6) |
| 6 | atcattaccacc (SEQ ID NO: 11) |
|  | ggtggtaatgat (SEQ ID NO: 12) |
| 7 | attaacgggagc (SEQ ID NO: 13) |
|  | gctcccgttaat (SEQ ID NO: 14) |
| 8 | cagaggtcttaa (SEQ ID NO: 15) |
|  | ttaagacctctg (SEQ ID NO: 16) |
| 9 | caggtgtccatt (SEQ ID NO: 17) |
|  | aatggacacctg (SEQ ID NO: 18) |
| 11 | cctacgatatac (SEQ ID NO: 21) |
|  | gtatatcgtagg (SEQ ID NO: 22) |
| 12 | cgaatgtagagt (SEQ ID NO: 23) |
|  | actctacattcg (SEQ ID NO: 24) |
| 13 | cggtttgagata (SEQ ID NO: 25) |
|  | tatctcaaaccg (SEQ ID NO: 26) |

-continued

| Pair | Sequence |
|------|----------|
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) | and (i) a set of oligonucleotides comprised of two or more oligonucleotides selected from:

| Pair | Sequence |
|------|----------|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) | wherein the oligonucleotides in component (ii) are complementary to the oligonucleotides in component (i).

Embodiment (16): a method of conducting a binding assay for a plurality of analytes comprising: (a) contacting a sample with two or more binding domains linked to at least a first and second binding reagent that each bind a first and second analyte, respectively, of the plurality of analytes to form complexes comprising the first analyte bound to the first binding reagent and the second analyte bound to the second binding reagent, wherein (x) the first binding domain comprises a first binding reagent complex comprising (i) a first targeting agent bound to the first binding domain and to a first targeting agent complement; and (ii) the first binding reagent bound to the first targeting agent complement via a linking complex; and (y) the second binding domain comprises a second binding reagent complex comprising (i) a second targeting agent bound to the second binding domain and to a second targeting agent complement; and (ii) the second binding reagent bound to the second targeting agent complement via a linking complex;

(b) contacting the first and second binding reagent complexes with a plurality of detection reagents comprising a first detection reagent that binds the first analyte or a complex comprising the first analyte, and a second detection reagent that binds the second analyte or a complex comprising the second analyte; and (c) measuring the amount of the first and second analytes bound to the two or more binding domains.

In embodiment (16), one or more of the following features can be adopted: the first and second binding reagents each comprise a receptor, ligand, antibody, hapten, antigen, epitope, mimitope, aptamer, or an intercalater capable of binding to the first and second analyte, respectively, e.g., the first and second binding reagents each comprise an antibody capable of binding to the first and second analyte, respectively; the first targeting agent and the first targeting agent complement comprise an oligonucleotide and a complementary oligonucleotide, a receptor-ligand pair, an antigen-antibody pair, a hapten-antibody pair, an epitope-antibody pair, an mimitope-antibody pair, an aptamer-target molecule pair, a hybridization partners, or an intercalater-target molecule pair; the second targeting agent and the second targeting agent complement comprise an oligonucleotide and a complementary oligonucleotide, a receptor-ligand pair, an antigen-antibody pair, a hapten-antibody pair, an epitope-antibody pair, an mimitope-antibody pair, an aptamer-target molecule pair, a hybridization partners, or an intercalater-target molecule pair; the first targeting agent and the first targeting agent complement comprise an oligonucleotide and a complementary oligonucleotide, respectively; the second targeting agent and the second targeting agent complement comprise an oligonucleotide and a complementary oligonucleotide, respectively; the linking complex comprises a linking agent and a supplemental linking agent connected thereto, e.g., the linking complex is formed by a binding interaction between (a) a thiol group and a maleimide or iodoacetamide; (b) an aldehyde and a hydrazide; or (c) an alkyne and an azide; or the (a) the linking agent is biotin and supplemental linking agent is streptavidin or avidin; (b) the linking agent is streptavidin or avidin and the supplemental linking agent is biotin; (c) the linking agent is a peptide and the supplemental linking agent is an anti-peptide antibody; or (d) the linking agent is an anti-peptide antibody and the supplemental linking agent is a peptide.

Moreover, embodiment (16) can optionally include one or more of the following features: each of the plurality of detection reagents comprise a detectable label; a subset of the plurality of detection reagents comprise a detectable label; the measuring step comprises measuring the presence of the detectable label in the sample via optical absorbance, fluorescence, phosphorescence, chemiluminescence, electrochemiluminescence, light scattering, or magnetism; the detectable label is an electrochemiluminescent label and the measuring step comprises measuring an electrochemiluminescent signal and correlating the signal with an amount of analyte in the sample, e.g., the two or more binding domains are positioned on an electrode and the measuring step further comprises applying a voltage waveform to the electrode to generate electrochemiluminescence, and optionally, the two or more binding domains are located within one or more wells of a multi-well plate.

Embodiment (16) can include conducting a sandwich immunoassay or a competitive immunoassay.

In embodiment (16), the first targeting agent and the first targeting agent complement can comprise a pair of oligonucleotides, wherein the pair is selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 14 | cttacaacgcca (SEQ ID NO: 27)<br>tggcgttgtaag (SEQ ID NO: 28) |
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 19 | ggtcgtgtttca (SEQ ID NO: 37)<br>tgaaacacgacc (SEQ ID NO: 38) |
| 20 | gttgattctgtc (SEQ ID NO: 39)<br>gacagaatcaac (SEQ ID NO: 40) |

-continued

| pair # | Sequence (5'-3') |
|---|---|
| 21 | tacccggaataa (SEQ ID NO: 41)<br>ttattccgggta (SEQ ID NO: 42) |
| 22 | tgcttgacttgg (SEQ ID NO: 43)<br>ccaagtcaagca (SEQ ID NO: 44) |
| 23 | ttccacttaggg (SEQ ID NO: 45)<br>ccctaagtggaa (SEQ ID NO: 46) |
| 24 | ttgtctagcggc (SEQ ID NO: 47)<br>gccgctagacaa (SEQ ID NO: 48) |
| 25 | tttcccttgcta (SEQ ID NO: 49)<br>tagcaagggaaa (SEQ ID NO: 50) |

Moreover, in embodiment (16), the first targeting agent and the first targeting agent complement can comprise a pair of oligonucleotides, wherein the pair is selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

In one example of embodiment (16), the second targeting agent and the second targeting agent complement can include a pair of oligonucleotides, wherein the pair is selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 14 | cttacaacgcca (SEQ ID NO: 27)<br>tggcgttgtaag (SEQ ID NO: 28) |
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 19 | ggtcgtgtttca (SEQ ID NO: 37)<br>tgaaacacgacc (SEQ ID NO: 38) |
| 20 | gttgattctgtc (SEQ ID NO: 39)<br>gacagaatcaac (SEQ ID NO: 40) |
| 21 | tacccggaataa (SEQ ID NO: 41)<br>ttattccgggta (SEQ ID NO: 42) |
| 22 | tgcttgacttgg (SEQ ID NO: 43)<br>ccaagtcaagca (SEQ ID NO: 44) |
| 23 | ttccacttaggg (SEQ ID NO: 45)<br>ccctaagtggaa (SEQ ID NO: 46) |
| 24 | ttgtctagcggc (SEQ ID NO: 47)<br>gccgctagacaa (SEQ ID NO: 48) |
| 25 | tttcccttgcta (SEQ ID NO: 49)<br>tagcaagggaaa (SEQ ID NO: 50) |

In a further example of embodiment (16), the second targeting agent and the second targeting agent complement can include a pair of oligonucleotides, wherein the pair is selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

Embodiment (16) can include one or more of the following elements: the first targeting agent and first targeting agent complement comprise a first oligonucleotide and a first complementary oligonucleotide, respectively, and the first oligonucleotide and the first complementary oligonucleotide each comprise approximately 10 to 50 bases; the first targeting agent and first targeting agent complement comprise a first oligonucleotide and a first complementary oligonucleotide, respectively, and the first oligonucleotide and the first complementary oligonucleotide each comprise approximately 10 to 25 bases; the first binding reagent is an antibody comprising a biotin molecule and the first targeting agent is a first oligonucleotide comprising a streptavidin molecule and the linking complex is formed by a reaction between the biotin and streptavidin molecules; and/or second binding reagent is an antibody comprising an additional biotin molecule and the second targeting agent is a second oligonucleotide comprising an additional streptavidin molecule and the linking complex is formed by a reaction between the additional biotin and the additional streptavidin molecules.

Embodiment (17): a method of conducting a binding assay for a plurality of analytes comprising: (a) forming a first binding reagent complex comprising a first binding reagent specific for a first analyte in the plurality of analytes and a first targeting agent, wherein the first binding reagent is bound to a linking agent and the first targeting agent is bound to a supplemental linking agent wherein the first binding reagent complex is formed by a reaction between the linking agent and the supplemental linking agent; (b) forming a second binding reagent complex comprising a second binding reagent specific for a second analyte in the plurality of analytes and a second targeting agent, wherein the second binding reagent is bound to a second linking agent and the second targeting agent is bound to a second linking agent complement wherein the second binding reagent complex is formed by a reaction between the second linking agent and the second linking agent complement; (c) mixing the first and second binding reagent complexes with two or more binding domains each linked to a first targeting agent complement and a second targeting agent complement, respectively, under conditions sufficient to bind the first targeting agent to the first targeting agent complement and the second targeting agent to the second targeting agent complement; (d) mixing a sample comprising the plurality of analytes to the mixture formed in step (c); (e) adding a plurality of additional binding reagents to the mixture formed in step (d), wherein the plurality of additional binding reagents includes (i) a first detection reagent specific for the first analyte and/or a first binding reagent-first analyte complex; and (ii) a second detection reagent specific for the second analyte and/or a second binding reagent-second analyte complex; and (f) measuring the amount of the first and second analytes bound to the binding domains.

Embodiment (17) can include one or more of the following features: the first and second binding reagents each comprise a receptor, ligand, antibody, hapten, antigen, epitope, mimitope, aptamer, or an intercalater capable of binding to the first and second analytes, respectively, e.g., the first and second binding reagents each comprise an antibody capable of binding to the first and second analyte, respectively; the first targeting agent and the first targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the second targeting agent and the second targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the first targeting agent and the first targeting agent complement comprise an oligonucleotide and a complementary oligonucleotide; the second targeting agent and the second targeting agent complement comprise an oligonucleotide and a complementary oligonucleotide; the linking complex comprises a linking agent and a supplemental linking agent connected thereto, e.g., the linking complex is formed by a binding interaction between (a) a thiol group and a maleimide or iodoacetamide; (b) an aldehyde and a hydrazide; or (c) an alkyne and an azide; the (a) the linking agent is biotin and supplemental linking agent is streptavidin or avidin; (b) the linking agent is streptavidin or avidin and the supplemental linking agent is biotin; (c) the linking agent is a peptide and the supplemental linking agent is an anti-peptide antibody; or (d) the linking agent is an anti-peptide antibody and the supplemental linking agent is a peptide.

Moreover, embodiment (17) can further include one or more of the following features: each of the plurality of detection reagents comprise a detectable label, e.g., a subset of the plurality of detection reagents comprise a detectable label; the measuring step comprises measuring the presence of the detectable label in the sample via optical absorbance, fluorescence, phosphorescence, chemiluminescence, electrochemiluminescence, light scattering, or magnetism; the detectable label is an electrochemiluminescent label and the measuring step comprises measuring an electrochemiluminescent signal and correlating the signal with an amount of analyte in the sample; the two or more binding domains are positioned on an electrode and the measuring step further comprises applying a voltage waveform to the electrode to generate electrochemiluminescence, e.g., the two or more binding domains are located within one or more wells of a multi-well plate.

Embodiment (17) can comprise conducting a sandwich immunoassay or a competitive immunoassay.

In embodiment (17), the first targeting agent and the first targeting agent complement comprise a pair of oligonucleotides, wherein the pair is selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 14 | cttacaacgcca (SEQ ID NO: 27)<br>tggcgttgtaag (SEQ ID NO: 28) |

-continued

| pair # | Sequence (5'-3') |
|---|---|
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 19 | ggtcgtgtttca (SEQ ID NO: 37)<br>tgaaacacgacc (SEQ ID NO: 38) |
| 20 | gttgattctgtc (SEQ ID NO: 39)<br>gacagaatcaac (SEQ ID NO: 40) |
| 21 | tacccggaataa (SEQ ID NO: 41)<br>ttattccgggta (SEQ ID NO: 42) |
| 22 | tgcttgacttgg (SEQ ID NO: 43)<br>ccaagtcaagca (SEQ ID NO: 44) |
| 23 | ttccacttaggg (SEQ ID NO: 45)<br>ccctaagtggaa (SEQ ID NO: 46) |
| 24 | ttgtctagcggc (SEQ ID NO: 47)<br>gccgctagacaa (SEQ ID NO: 48) |
| 25 | tttcccttgcta (SEQ ID NO: 49)<br>tagcaagggaaa (SEQ ID NO: 50) |

In a specific example of embodiment (17), the first targeting agent and the first targeting agent complement comprise a pair of oligonucleotides, wherein the pair is selected from:

| Pair | Sequence |
|---|---|
| 1 | acatcggtagtt (SEQ ID NO: 1)<br>aactaccgatgt (SEQ ID NO: 2) |
| 3 | agaagaagatcc (SEQ ID NO: 5)<br>ggatcttcttct (SEQ ID NO: 6) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 16 | gacataaagcga (SEQ ID NO: 31)<br>tcgctttatgtc (SEQ ID NO: 32) |

-continued

| Pair | Sequence |
|---|---|
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 20 | gttgattctgtc (SEQ ID NO: 39)<br>gacagaatcaac (SEQ ID NO: 40) |
| 23 | ttccacttaggg (SEQ ID NO: 45)<br>ccctaagtggaa (SEQ ID NO: 46) |
| 25 | tttcccttgcta (SEQ ID NO: 49)<br>tagcaagggaaa (SEQ ID NO: 50) |

In a further example of embodiment (17), the second targeting agent and the second targeting agent complement comprise a pair of oligonucleotides, wherein the pair is selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 14 | cttacaacgcca (SEQ ID NO: 27)<br>tggcgttgtaag (SEQ ID NO: 28) |
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |

-continued

| pair # | Sequence (5'-3') |
|--------|------------------|
| 18 | gctaattcacca (SEQ ID NO: 35) <br> tggtgaattagc (SEQ ID NO: 36) |
| 19 | ggtcgtgtttca (SEQ ID NO: 37) <br> tgaaacacgacc (SEQ ID NO: 38) |
| 20 | gttgattctgtc (SEQ ID NO: 39) <br> gacagaatcaac (SEQ ID NO: 40) |
| 21 | tacccggaataa (SEQ ID NO: 41) <br> ttattccgggta (SEQ ID NO: 42) |
| 22 | tgcttgacttgg (SEQ ID NO: 43) <br> ccaagtcaagca (SEQ ID NO: 44) |
| 23 | ttccacttaggg (SEQ ID NO: 45) <br> ccctaagtggaa (SEQ ID NO: 46) |
| 24 | ttgtctagcggc (SEQ ID NO: 47) <br> gccgctagacaa (SEQ ID NO: 48) |
| 25 | tttcccttgcta (SEQ ID NO: 49) <br> tagcaagggaaa (SEQ ID NO: 50) |

In yet a further example of embodiment (17), the second targeting agent and the second targeting agent complement comprise a pair of oligonucleotides, wherein the pair is selected from:

| Pair | Sequence |
|------|----------|
| 1 | acatcggtagtt (SEQ ID NO: 1) <br> aactaccgatgt (SEQ ID NO: 2) |
| 3 | agaagaagatcc (SEQ ID NO: 5) <br> ggatcttcttct (SEQ ID NO: 6) |
| 6 | atcattaccacc (SEQ ID NO: 11) <br> ggtggtaatgat (SEQ ID NO: 12) |
| 7 | attaacgggagc (SEQ ID NO: 13) <br> gctcccgttaat (SEQ ID NO: 14) |
| 8 | cagaggtcttaa (SEQ ID NO: 15) <br> ttaagacctctg (SEQ ID NO: 16) |
| 9 | caggtgtccatt (SEQ ID NO: 17) <br> aatggacacctg (SEQ ID NO: 18) |
| 11 | cctacgatatac (SEQ ID NO: 21) <br> gtatatcgtagg (SEQ ID NO: 22) |
| 12 | cgaatgtagagt (SEQ ID NO: 23) <br> actctacattcg (SEQ ID NO: 24) |
| 13 | cggtttgagata (SEQ ID NO: 25) <br> tatctcaaaccg (SEQ ID NO: 26) |
| 16 | gacataaagcga (SEQ ID NO: 31) <br> tcgctttatgtc (SEQ ID NO: 32) |
| 17 | gccatagtctct (SEQ ID NO: 33) <br> agagactatggc (SEQ ID NO: 34) |
| 18 | gctaattcacca (SEQ ID NO: 35) <br> tggtgaattagc (SEQ ID NO: 36) |
| 20 | gttgattctgtc (SEQ ID NO: 39) <br> gacagaatcaac (SEQ ID NO: 40) |

-continued

| Pair | Sequence |
|------|----------|
| 23 | ttccacttaggg (SEQ ID NO: 45) <br> ccctaagtggaa (SEQ ID NO: 46) |
| 25 | tttcccttgcta (SEQ ID NO: 49) <br> tagcaagggaaa (SEQ ID NO: 50) |

Embodiment (17) can include one or more of the following elements: the first targeting agent and the first targeting agent complement comprise a first oligonucleotide and a first complementary oligonucleotide, respectively, and the first oligonucleotide and the first complementary oligonucleotide each comprise approximately 10 to 50 bases; the first targeting agent and the first targeting agent complement comprise a first oligonucleotide and a first complementary oligonucleotide, respectively, and the first oligonucleotide and the first complementary oligonucleotide each comprise approximately 10 to 25 bases; the first binding reagent is an antibody comprising a biotin molecule and the first targeting agent comprises a first oligonucleotide including a streptavidin molecule and the linking complex is formed by a reaction between the biotin and streptavidin molecules; the second binding reagent is an antibody comprising an additional biotin molecule and the second targeting agent comprises a second oligonucleotide including an additional streptavidin molecule and the linking complex is formed by a reaction between the additional biotin and the additional streptavidin molecules; the second targeting agent and the second targeting agent complement comprise a second oligonucleotide and a second complementary oligonucleotide, respectively, and the second oligonucleotide and the second complementary oligonucleotide each comprise approximately 10 to 50 bases; the second targeting agent and the second targeting agent complement comprise a second oligonucleotide and a second complementary oligonucleotide, respectively, and the second oligonucleotide and the second complementary oligonucleotide each comprise approximately 10 to 25 bases; the second binding reagent is an antibody comprising a biotin molecule and the second targeting agent comprises a second oligonucleotide including a streptavidin molecule and the linking complex is formed by a reaction between the biotin and streptavidin molecules; and/or the method further comprises the step of washing the mixture formed in step (c) prior to mixing step (d).

Embodiment (18): a method of conducting a binding assay for a plurality of analytes in a sample comprising: (a) forming a first binding reagent complex comprising a first binding reagent specific for a first analyte in the plurality of analytes and a first targeting agent, wherein the first binding reagent is bound to a linking agent and the first targeting agent is bound to a supplemental linking agent wherein the first binding reagent complex is formed by a reaction between the linking agent and the supplemental linking agent; (b) forming a second binding reagent complex comprising a second binding reagent specific for a second analyte in the plurality of analytes and a second targeting agent, wherein the second binding reagent is bound to a second linking agent and the second targeting agent is bound to a second linking agent complement wherein the second binding reagent complex is formed by a reaction between the second linking agent and the second linking agent complement; (c) mixing the first and second binding reagent complexes and the sample with two or more binding domains each linked to a first targeting agent complement and a second targeting agent complement, respectively, under conditions sufficient to bind the first targeting agent to the first targeting agent complement and the second targeting agent to the second targeting agent complement; (d) adding a plurality of additional binding reagents to the mixture formed in step (c), wherein the plurality of additional binding reagents includes (i) a first detection reagent specific for the first analyte and/or a first binding reagent-first analyte complex; and (ii) a second detection reagent specific for the second analyte and/or a second binding reagent-second analyte complex; and (e) measuring the amount of the first and second analytes bound to the binding domains.

In addition, embodiment (18) can include one or more of the following: the first and second binding reagents each comprise a receptor, ligand, antibody, hapten, antigen, epitope, mimitope, aptamer, or an intercalater capable of binding to the first and second analytes, respectively; first and second binding reagents each comprise an antibody capable of binding to the first and second analyte, respectively; first targeting agent and the first targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the second targeting agent and the second targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the first targeting agent and the first targeting agent complement comprise an oligonucleotide and a complementary oligonucleotide; the second targeting agent and the second targeting agent complement comprise an oligonucleotide and a complementary oligonucleotide; the linking complex comprises a linking agent and a supplemental linking agent connected thereto, e.g., the linking complex is formed by a binding interaction between (a) a thiol group and a maleimide or iodoacetamide; (b) an aldehyde and a hydrazide; or (c) an alkyne and an azide; e.g., (a) the linking agent is biotin and supplemental linking agent is streptavidin or avidin; (b) the linking agent is streptavidin or avidin and the supplemental linking agent is biotin; (c) the linking agent is a peptide and the supplemental linking agent is an anti-peptide antibody; or (d) the linking agent is an anti-peptide antibody and the supplemental linking agent is a peptide.

Still further, embodiment (18) can include one or more of the following elements: each of the plurality of detection reagents comprise a detectable label; the plurality of detection reagents comprise a detectable label; the measuring step comprises measuring the presence of the detectable label in the sample via optical absorbance, fluorescence, phosphorescence, chemiluminescence, electrochemiluminescence, light scattering, or magnetism; the detectable label is an electrochemiluminescent label and the measuring step comprises measuring an electrochemiluminescent signal and correlating the signal with an amount of analyte in the sample; the two or more binding domains are positioned on an electrode and the measuring step further comprises applying a voltage waveform to the electrode to generate electrochemiluminescence; and/or the two or more binding domains are located within one or more wells of a multi-well plate.

Embodiment (18) can include conducting a sandwich immunoassay or a competitive immunoassay.

In a specific example of embodiment (18), the first targeting agent and the first targeting agent complement comprise a pair of oligonucleotides, wherein the pair is selected from:

| pair # | Sequence (5'-3') |
|---|---|
| 1 | acatcggtagtt (SEQ ID NO: 1)<br>aactaccgatgt (SEQ ID NO: 2) |
| 2 | acgtcccagttg (SEQ ID NO: 3)<br>caactgggacgt (SEQ ID NO: 4) |
| 3 | agaagaagatcc (SEQ ID NO: 5)<br>ggatcttcttct (SEQ ID NO: 6) |
| 4 | aggttcagtgca (SEQ ID NO: 7)<br>tgcactgaacct (SEQ ID NO: 8) |
| 5 | atcaggatacgc (SEQ ID NO: 9)<br>gcgtatcctgat (SEQ ID NO: 10) |
| 6 | atcattaccacc (SEQ ID NO: 11)<br>ggtggtaatgat (SEQ ID NO: 12) |
| 7 | attaacgggagc (SEQ ID NO: 13)<br>gctcccgttaat (SEQ ID NO: 14) |
| 8 | cagaggtcttaa (SEQ ID NO: 15)<br>ttaagacctctg (SEQ ID NO: 16) |
| 9 | caggtgtccatt (SEQ ID NO: 17)<br>aatggacacctg (SEQ ID NO: 18) |
| 10 | catccaatccag (SEQ ID NO: 19)<br>ctggattggatg (SEQ ID NO: 20) |
| 11 | cctacgatatac (SEQ ID NO: 21)<br>gtatatcgtagg (SEQ ID NO: 22) |
| 12 | cgaatgtagagt (SEQ ID NO: 23)<br>actctacattcg (SEQ ID NO: 24) |
| 13 | cggtttgagata (SEQ ID NO: 25)<br>tatctcaaaccg (SEQ ID NO: 26) |
| 14 | cttacaacgcca (SEQ ID NO: 27)<br>tggcgttgtaag (SEQ ID NO: 28) |
| 15 | ctttctcggcac (SEQ ID NO: 29)<br>gtgccgagaaag (SEQ ID NO: 30) |
| 16 | gacataaagcga (SEQ ID NO: 31)<br>tcgctttatgtc (SEQ ID NO: 32) |
| 17 | gccatagtctct (SEQ ID NO: 33)<br>agagactatggc (SEQ ID NO: 34) |
| 18 | gctaattcacca (SEQ ID NO: 35)<br>tggtgaattagc (SEQ ID NO: 36) |
| 19 | ggtcgtgtttca (SEQ ID NO: 37)<br>tgaaacacgacc (SEQ ID NO: 38) |
| 20 | gttgattctgtc (SEQ ID NO: 39)<br>gacagaatcaac (SEQ ID NO: 40) |
| 21 | tacccggaataa (SEQ ID NO: 41)<br>ttattccgggta (SEQ ID NO: 42) |

-continued

| pair # | Sequence (5'-3') |
|---|---|
| 22 | tgcttgacttgg (SEQ ID NO: 43) |
| | ccaagtcaagca (SEQ ID NO: 44) |
| 23 | ttccacttaggg (SEQ ID NO: 45) |
| | ccctaagtggaa (SEQ ID NO: 46) |
| 24 | ttgtctagcggc (SEQ ID NO: 47) |
| | gccgctagacaa (SEQ ID NO: 48) |
| 25 | tttcccttgcta (SEQ ID NO: 49) |
| | tagcaagggaaa (SEQ ID NO: 50) |

In a another example of embodiment (18), the first targeting agent and the first targeting agent complement comprise a pair of oligonucleotides, wherein the pair is selected from:

| Pair | Sequence |
|---|---|
| 1 | acatcggtagtt (SEQ ID NO: 1) |
| | aactaccgatgt (SEQ ID NO: 2) |
| 3 | agaagaagatcc (SEQ ID NO: 5) |
| | ggatcttcttct (SEQ ID NO: 6) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |
| 18 | gctaattcacca (SEQ ID NO: 35) |
| | tggtgaattagc (SEQ ID NO: 36) |
| 20 | gttgattctgtc (SEQ ID NO: 39) |
| | gacagaatcaac (SEQ ID NO: 40) |
| 23 | ttccacttaggg (SEQ ID NO: 45) |
| | ccctaagtggaa (SEQ ID NO: 46) |
| 25 | tttcccttgcta (SEQ ID NO: 49) |
| | tagcaagggaaa (SEQ ID NO: 50) |

In yet another example of embodiment (18), the second targeting agent and the second targeting agent complement comprise a pair of oligonucleotides, wherein the pair is selected from:

| pair # | Sequence (5'-3') |
|---|---|
| 1 | acatcggtagtt (SEQ ID NO: 1) |
| | aactaccgatgt (SEQ ID NO: 2) |
| 2 | acgtcccagttg (SEQ ID NO: 3) |
| | caactgggacgt (SEQ ID NO: 4) |
| 3 | agaagaagatcc (SEQ ID NO: 5) |
| | ggatcttcttct (SEQ ID NO: 6) |
| 4 | aggttcagtgca (SEQ ID NO: 7) |
| | tgcactgaacct (SEQ ID NO: 8) |
| 5 | atcaggatacgc (SEQ ID NO: 9) |
| | gcgtatcctgat (SEQ ID NO: 10) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 10 | catccaatccag (SEQ ID NO: 19) |
| | ctggattggatg (SEQ ID NO: 20) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 14 | cttacaacgcca (SEQ ID NO: 27) |
| | tggcgttgtaag (SEQ ID NO: 28) |
| 15 | ctttctcggcac (SEQ ID NO: 29) |
| | gtgccgagaaag (SEQ ID NO: 30) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |
| 18 | gctaattcacca (SEQ ID NO: 35) |
| | tggtgaattagc (SEQ ID NO: 36) |
| 19 | ggtcgtgtttca (SEQ ID NO: 37) |
| | tgaaacacgacc (SEQ ID NO: 38) |
| 20 | gttgattctgtc (SEQ ID NO: 39) |
| | gacagaatcaac (SEQ ID NO: 40) |
| 21 | tacccggaataa (SEQ ID NO: 41) |
| | ttattccgggta (SEQ ID NO: 42) |
| 22 | tgcttgacttgg (SEQ ID NO: 43) |
| | ccaagtcaagca (SEQ ID NO: 44) |
| 23 | ttccacttaggg (SEQ ID NO: 45) |
| | ccctaagtggaa (SEQ ID NO: 46) |
| 24 | ttgtctagcggc (SEQ ID NO: 47) |
| | gccgctagacaa (SEQ ID NO: 48) |
| 25 | tttcccttgcta (SEQ ID NO: 49) |
| | tagcaagggaaa (SEQ ID NO: 50) |

41

In a further example of embodiment (18), the second targeting agent and the second targeting agent complement comprise a pair of oligonucleotides, wherein the pair is selected from:

| Pair | Sequence |
|---|---|
| 1 | acatcggtagtt (SEQ ID NO. 1) |
| | aactaccgatgt (SEQ ID NO: 2) |
| 3 | agaagaagatcc (SEQ ID NO: 5) |
| | ggatcttcttct (SEQ ID NO: 6) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 11 | cctacgatatac (SEQ ID NO: 21) |
| | gtatatcgtagg (SEQ ID NO: 22) |
| 12 | cgaatgtagagt (SEQ ID NO. 23) |
| | actctacattcg (SEQ ID NO: 24) |
| 13 | cggtttgagata (SEQ ID NO: 25) |
| | tatctcaaaccg (SEQ ID NO: 26) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |

42

-continued

| Pair | Sequence |
|---|---|
| 18 | gctaattcacca (SEQ ID NO: 35) |
| | tggtgaattagc (SEQ ID NO: 36) |
| 20 | gttgattctgtc (SEQ ID NO: 39) |
| | gacagaatcaac (SEQ ID NO: 40) |
| 23 | ttccacttaggg (SEQ ID NO: 45) |
| | ccctaagtggaa (SEQ ID NO: 46) |
| 25 | tttcccttgcta (SEQ ID NO: 49) |
| | tagcaagggaaa (SEQ ID NO: 50) |

Embodiment (18) can include one or more of the following features: the first targeting agent and the first targeting agent complement comprise a first oligonucleotide and a first complementary oligonucleotide, respectively, and the first oligonucleotide and the first complementary oligonucleotide each comprise approximately 10 to 50 bases; the first targeting agent and the first targeting agent complement comprise a first oligonucleotide and a first complementary oligonucleotide, respectively, and the first oligonucleotide and the first complementary oligonucleotide each comprise approximately 10 to 25 bases; the first binding reagent is an antibody comprising a biotin molecule and the first targeting agent comprises a first oligonucleotide including a streptavidin molecule and the linking complex is formed by a reaction between the biotin and streptavidin molecules; the second binding reagent is an antibody comprising an additional biotin molecule and the second targeting agent comprises a second oligonucleotide including an additional streptavidin molecule and the linking complex is formed by a reaction between the additional biotin and the additional streptavidin molecules; the second targeting agent and the second targeting agent complement comprise a second oligonucleotide and a second complementary oligonucleotide, respectively, and the second oligonucleotide and the second complementary oligonucleotide each comprise approximately 10 to 50 bases; the second targeting agent and the second targeting agent complement comprise a second oligonucleotide and a second complementary oligonucleotide, respectively, and the second oligonucleotide and the second complementary oligonucleotide each comprise approximately 10 to 25 bases; the second binding reagent is an antibody comprising a biotin molecule and the second targeting agent comprises a second oligonucleotide including a streptavidin molecule and the linking complex is formed by a reaction between the biotin and streptavidin molecules; and/or the method further comprises the step of washing the mixture formed in step (c) prior to mixing step (d).

Embodiment (19): a kit comprising: (a) a multi-well plate comprising a plurality of discrete binding domains each comprising a first and second oligonucleotide, respectively; (b) in a separate vial, container, or compartment, a set of targeting reagents comprising a first oligonucleotide complement bound to a linking agent and a second oligo-nucleotide complement bound to a second linking agent, wherein (i) the first oligonucleotide and the first oligonucle-otide complement comprise a first pair of oligonucleotides, and (ii) the second oligonucleotide and the second oligo-nucleotide complement comprise a second pair of oligo-nucleotides, wherein the first and second pair of oligonucle-otides, respectively, are selected from:

| pair # | Sequence (5'-3') |
|---|---|
| 1 | acatcggtagtt (SEQ ID NO: 1) |
| | aactaccgatgt (SEQ ID NO: 2) |
| 2 | acgtcccagttg (SEQ ID NO: 3) |
| | caactgggacgt (SEQ ID NO: 4) |
| 3 | agaagaagatcc (SEQ ID NO: 5) |
| | ggatcttcttct (SEQ ID NO: 6) |
| 4 | aggttcagtgca (SEQ ID NO: 7) |
| | tgcactgaacct (SEQ ID NO: 8) |
| 5 | atcaggatacgc (SEQ ID NO: 9) |
| | gcgtatcctgat (SEQ ID NO: 10) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 10 | catccaatccag (SEQ ID NO: 19) |
| | ctggattggatg (SEQ ID NO: 20) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 14 | cttacaacgcca (SEQ ID NO: 27) |
| | tggcgttgtaag (SEQ ID NO: 28) |
| 15 | ctttctcggcac (SEQ ID NO: 29) |
| | gtgccgagaaag (SEQ ID NO: 30) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |

-continued

| pair # | Sequence (5'-3') |
|---|---|
| 18 | gctaattcacca (SEQ ID NO: 35) |
| | tggtgaattagc (SEQ ID NO: 36) |
| 19 | ggtcgtgtttca (SEQ ID NO: 37) |
| | tgaaacacgacc (SEQ ID NO: 38) |
| 20 | gttgattctgtc (SEQ ID NO: 39) |
| | gacagaatcaac (SEQ ID NO: 40) |
| 21 | tacccggaataa (SEQ ID NO: 41) |
| | ttattccgggta (SEQ ID NO: 42) |
| 22 | tgcttgacttgg (SEQ ID NO: 43) |
| | ccaagtcaagca (SEQ ID NO: 44) |
| 23 | ttccacttaggg (SEQ ID NO: 45) |
| | ccctaagtggaa (SEQ ID NO: 46) |
| 24 | ttgtctagcggc (SEQ ID NO: 47) |
| | gccgctagacaa (SEQ ID NO: 48) |
| 25 | tttcccttgcta (SEQ ID NO: 49) |
| | tagcaagggaaa (SEQ ID NO: 50) |

Embodiment (20): a kit comprising: (a) a multi-well plate comprising a plurality of discrete binding domains each comprising a first and second oligonucleotide, respectively; (b) in a separate vial, container, or compartment, a set of targeting reagents comprising a first oligonucleotide complement bound to a linking agent and a second oligo-nucleotide complement bound to a second linking agent, wherein (i) the first oligonucleotide and the first oligonucle-otide complement comprise a first pair of oligonucleotides, and (ii) the second oligonucleotide and the second oligo-nucleotide complement comprise a second pair of oligo-nucleotides, wherein the first and second pair of oligonucle-otides, respectively, are selected from:

| Pair | Sequence |
|---|---|
| 1 | acatcggtagtt (SEQ ID NO: 1) |
| | aactaccgatgt (SEQ ID NO: 2) |
| 3 | agaagaagatcc (SEQ ID NO: 5) |
| | ggatcttcttct (SEQ ID NO: 6) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |

-continued

| Pair | Sequence |
|------|----------|
| 8 | cagaggtcttaa<br>(SEQ ID NO: 15) |
| | ttaagacctctg<br>(SEQ ID NO: 16) |
| 9 | caggtgtccatt<br>(SEQ ID NO: 17) |
| | aatggacacctg<br>(SEQ ID NO: 18) |
| 11 | cctacgatatac<br>(SEQ ID NO: 21) |
| | gtatatcgtagg<br>(SEQ ID NO: 22) |
| 12 | cgaatgtagagt<br>(SEQ ID NO: 23) |
| | actctacattcg<br>(SEQ ID NO: 24) |
| 13 | cggtttgagata<br>(SEQ ID NO: 25) |
| | tatctcaaaccg<br>(SEQ ID NO: 26) |
| 16 | gacataaagcga<br>(SEQ ID NO: 31) |
| | tcgctttatgtc<br>(SEQ ID NO: 32) |
| 17 | gccatagtctct<br>(SEQ ID NO: 33) |
| | agagactatggc<br>(SEQ ID NO: 34) |
| 18 | gctaattcacca<br>(SEQ ID NO: 35) |
| | tggtgaattagc<br>(SEQ ID NO: 36) |
| 20 | gttgattctgtc<br>(SEQ ID NO: 39) |
| | gacagaatcaac<br>(SEQ ID NO: 40) |
| 23 | ttccacttaggg<br>(SEQ ID NO: 45) |
| | ccctaagtggaa<br>(SEQ ID NO: 46) |
| 25 | tttcccttgcta<br>(SEQ ID NO: 49) |
| | tagcaagggaaa<br>(SEQ ID NO: 50) |

Embodiments (19) and (20) can further include (b) one or more additional containers, vessels or compartments comprising: (i) a first binding reagent comprising a linking agent, wherein the first binding reagent is specific for a first analyte in the sample, (ii) a first targeting agent complement comprising a supplemental linking agent, provided in a separate container, vessel or compartment or as a component of (b)(i), (iii) a second binding reagent comprising a second linking agent, wherein the second binding reagent is specific for a second analyte in the sample, and (iv) a second targeting agent complement comprising a second linking agent complement, provided in a separate container, vessel or compartment or as a component of (b)(iii).

Embodiment (21): a kit for measuring a plurality of different analytes in a sample, the kit comprising: (a) a container, vessel or compartment comprising on a solid support a first targeting agent immobilized to a first region of the solid support and a second targeting agent immobilized to a second region of the solid support; and (b) one or more additional containers, vessels or compartments comprising: (i) a first binding reagent comprising a linking agent, wherein the first binding reagent is specific for a first analyte in the sample, (ii) a first targeting agent complement comprising a supplemental linking agent, provided in a separate container, vessel or compartment or as a component of (b)(i), (iii) a second binding reagent comprising a second linking agent, wherein the second binding reagent is specific for a second analyte in the sample, and (iv) a second targeting agent complement comprising a second linking agent complement, provided in a separate container, vessel or compartment or as a component of (b)(iii).

Embodiment (22): a kit for measuring a plurality of different analytes in a sample, the kit comprising: (a) a container, vessel or compartment comprising on a solid support a first targeting agent immobilized to a first region of the solid support and a second targeting agent immobilized to a second region of the solid support; and (b) four or more additional containers, vessels or compartments comprising: (i) a first container comprising a first binding reagent comprising a first linking agent, wherein the first binding reagent is specific for a first analyte in the sample, (ii) a second container comprising a first targeting agent complement comprising a supplemental linking agent, provided in a separate container, vessel or compartment, (iii) a third container comprising a second binding reagent comprising a second linking agent, wherein the second binding reagent is specific for a second analyte in the sample, and (iv) a fourth container comprising a second targeting agent complement comprising a second linking agent complement, provided in a separate container, vessel or compartment.

Embodiment (23): a kit for measuring a plurality of different analytes in a sample, the kit comprising: (a) a container, vessel or compartment comprising on a solid support a first targeting agent immobilized to a first region of the solid support and a second targeting agent immobilized to a second region of the solid support; and (b) two or more additional containers, vessels or compartments comprising: (i) a first container comprising a first binding reagent comprising a first linking agent, wherein the first binding reagent is specific for a first analyte in the sample, and a first targeting agent complement comprising a first linking agent complement, and (ii) a second container comprising a second binding reagent comprising a second linking agent, wherein the second binding reagent is specific for a second analyte in the sample, and a second targeting agent complement comprising a second linking agent complement.

Embodiment (24): a kit comprising (a) a multi-well plate comprising a plurality of discrete binding domains each comprising a first and second oligonucleotide, respectively, each of the first and second oligonucleotides are selected from:

| Sequence (5'-3') | |
|---|---|
| acatcggtagtt | (SEQ ID NO: 1) |
| aactaccgatgt | (SEQ ID NO: 2) |
| acgtcccagttg | (SEQ ID NO: 3) |
| caactgggacgt | (SEQ ID NO: 4) |
| agaagaagatcc | (SEQ ID NO: 5) |
| ggatcttcttct | (SEQ ID NO: 6) |
| aggttcagtgca | (SEQ ID NO: 7) |
| tgcactgaacct | (SEQ ID NO: 8) |
| atcaggatacgc | (SEQ ID NO: 9) |
| gcgtatcctgat | (SEQ ID NO: 10) |
| atcattaccacc | (SEQ ID NO: 11) |
| ggtggtaatgat | (SEQ ID NO: 12) |
| attaacgggagc | (SEQ ID NO: 13) |
| gctcccgttaat | (SEQ ID NO: 14) |
| cagaggtcttaa | (SEQ ID NO: 15) |
| ttaagacctctg | (SEQ ID NO: 16) |
| caggtgtccatt | (SEQ ID NO: 17) |
| aatggacacctg | (SEQ ID NO: 18) |
| catccaatccag | (SEQ ID NO: 19) |
| ctggattggatg | (SEQ ID NO: 20) |
| cctacgatatac | (SEQ ID NO: 21) |
| gtatatcgtagg | (SEQ ID NO: 22) |
| cgaatgtagagt | (SEQ ID NO: 23) |
| actctacattcg | (SEQ ID NO: 24) |
| cggtttgagata | (SEQ ID NO: 25) |
| tatctcaaaccg | (SEQ ID NO: 26) |

-continued

| Sequence (5'-3') | |
|---|---|
| cttacaacgcca | (SEQ ID NO: 27) |
| tggcgttgtaag | (SEQ ID NO: 28) |
| ctttctcggcac | (SEQ ID NO: 29) |
| gtgccgagaaag | (SEQ ID NO: 30) |
| gacataaagcga | (SEQ ID NO: 31) |
| tcgctttatgtc | (SEQ ID NO: 32) |
| gccatagtctct | (SEQ ID NO: 33) |
| agagactatggc | (SEQ ID NO: 34) |
| gctaattcacca | (SEQ ID NO: 35) |
| tggtgaattagc | (SEQ ID NO: 36) |
| ggtcgtgtttca | (SEQ ID NO: 37) |
| tgaaacacgacc | (SEQ ID NO: 38) |
| gttgattctgtc | (SEQ ID NO: 39) |
| gacagaatcaac | (SEQ ID NO: 40) |
| tacccggaataa | (SEQ ID NO: 41) |
| ttattccgggta | (SEQ ID NO: 42) |
| tgcttgacttgg | (SEQ ID NO: 43) |
| ccaagtcaagca | (SEQ ID NO: 44) |
| ttccacttaggg | (SEQ ID NO: 45) |
| ccctaagtggaa | (SEQ ID NO: 46) |
| ttgtctagcggc | (SEQ ID NO: 47) |
| gccgctagacaa | (SEQ ID NO: 48) |
| tttccettgcta | (SEQ ID NO: 49) |
| tagcaagggaaa | (SEQ ID NO: 50) |

The kit of embodiment (24) can include one or more of the following sequences:

| Sequence |
| --- |
| acatcggtagtt (SEQ ID NO: 1) |
| aactaccgatgt (SEQ ID NO: 2) |
| agaagaagatcc (SEQ ID NO: 5) |
| ggatcttcttct (SEQ ID NO: 6) |
| atcattaccacc (SEQ ID NO: 11) |
| ggtggtaatgat (SEQ ID NO: 12) |
| attaacgggagc (SEQ ID NO: 13) |
| gctcccgttaat (SEQ ID NO: 14) |
| cagaggtcttaa (SEQ ID NO: 15) |
| ttaagacctctg (SEQ ID NO: 16) |
| caggtgtccatt (SEQ ID NO: 17) |
| aatggacacctg (SEQ ID NO: 18) |
| cctacgatatac (SEQ ID NO: 21) |
| gtatatcgtagg (SEQ ID NO: 22) |
| cgaatgtagagt (SEQ ID NO: 23) |
| actctacattcg (SEQ ID NO: 24) |
| cggtttgagata (SEQ ID NO: 25) |
| tatctcaaaccg (SEQ ID NO: 26) |
| gacataaagcga (SEQ ID NO: 31) |
| tcgctttatgtc (SEQ ID NO: 32) |
| gccatagtctct (SEQ ID NO: 33) |
| agagactatggc (SEQ ID NO: 34) |
| gctaattcacca (SEQ ID NO: 35) |
| tggtgaattagc (SEQ ID NO: 36) |
| gttgattctgtc (SEQ ID NO: 39) |
| gacagaatcaac (SEQ ID NO: 40) |
| ttccacttaggg (SEQ ID NO: 45) |
| ccctaagtggaa (SEQ ID NO: 46) |
| tttcccttgcta (SEQ ID NO: 49) |
| tagcaagggaaa (SEQ ID NO: 50) |

Embodiment (24) can further include instructions for use of the multi-well plate in a method of conducting a binding assay for a plurality of analytes, the method comprising the steps of: (a) forming a first binding reagent complex comprising a first binding reagent specific for a first analyte in the plurality of analytes and the first oligonucleotide, wherein the first binding reagent is bound to a linking agent and the first oligonucleotide is bound to a supplemental linking agent wherein the first binding reagent complex is formed by a reaction between the linking agent and the supplemental linking agent; (b) forming a second binding reagent complex comprising a second binding reagent specific for a second analyte in the plurality of analytes and the second oligonucleotide, wherein the second binding reagent is bound to a second linking agent and the second oligonucleotide is bound to a second linking agent complement wherein the second binding reagent complex is formed by a reaction between the second linking agent and the second linking agent complement; (c) mixing the first and second binding reagent complexes with the two or more binding domains each linked to a first oligonucleotide complement and a second oligonucleotide complement, respectively, under conditions sufficient to bind the first oligonucleotide to the first oligonucleotide complement and the second oligonucleotide to the second oligonucleotide complement; (d) mixing a sample comprising the plurality of analytes to the mixture formed in step (c); (e) adding a plurality of additional binding reagents to the mixture formed in step (d), wherein the plurality of additional binding reagents includes (i) a first detection reagent specific for the first analyte and/or a first binding reagent-first analyte complex; and (ii) a second detection reagent specific for the second analyte and/or a second binding reagent-second analyte complex; and (f) measuring the amount of the first and second analytes bound to the binding domains.

In addition, embodiment (24) can include one or more of the following elements: the first and second binding reagents each comprise a receptor, ligand, antibody, hapten, antigen, epitope, mimitope, aptamer, or an intercalater capable of binding to the first and second analytes, respectively, e.g., the first and second binding reagents each comprise an antibody capable of binding to the first and second analyte, respectively; the first targeting agent and the first targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the second targeting agent and the second targeting agent complement comprise an oligonucleotide and a complementary oligonucleotide, a receptor-ligand pair, an antigen-antibody pair, a hapten-antibody pair, an antigen-antibody pair, an epitope-antibody pair, an mimitope-antibody pair, an aptamer-target molecule pair, hybridization partners, or an intercalater-target molecule pair; the first targeting agent and the first targeting agent complement comprise an oligonucleotide and a complementary oligonucleotide; the second targeting agent and the second targeting agent complement comprise an oligonucleotide and a complementary oligonucleotide; the linking complex comprises a linking agent and a supplemental linking agent connected thereto, e.g., the linking complex is formed by a binding interaction between (a) a thiol group and a maleimide or iodoacetamide; (b) an aldehyde and a hydrazide; or (c) an alkyne and an azide; or the (a) the linking agent is biotin and supplemental linking agent is streptavidin or avidin; (b) the linking agent is streptavidin or avidin and the supplemental linking agent is biotin; (c) the linking agent is a peptide and the supplemental linking agent is an anti-peptide antibody; or (d) the linking agent is an anti-peptide antibody and the supplemental linking agent is a peptide.

In addition, embodiment (24) can further comprise, in a separate vial, container, or compartment, a plurality of detection reagents. For example, the plurality of detection reagents can comprise a detectable label, e.g., a subset of the plurality of detection reagents comprise a detectable label. In one example, the detectable label is an electrochemilumi-nescent label. The two or more binding domains can be positioned on an electrode. Optionally, the two or more binding domains are located within one or more wells of a multi-well plate.

In a specific example of embodiment (24), the first targeting agent and the first targeting agent complement comprise a pair of oligonucleotides, wherein the pair is selected from:

| Pair | Sequence |
|------|----------|
| 1 | acatcggtagtt (SEQ ID NO: 1) |
| | aactaccgatgt (SEQ ID NO: 2) |
| 3 | agaagaagatcc (SEQ ID NO: 5) |
| | ggatcttcttct (SEQ ID NO: 6) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |
| 18 | gctaattcacca (SEQ ID NO: 35) |
| | tggtgaattagc (SEQ ID NO: 36) |
| 20 | gttgattctgtc (SEQ ID NO: 39) |
| | gacagaatcaac (SEQ ID NO: 40) |
| 23 | ttccacttaggg (SEQ ID NO: 45) |
| | ccctaagtggaa (SEQ ID NO: 46) |
| 25 | tttcccttgcta (SEQ ID NO: 49) |
| | tagcaagggaaa (SEQ ID NO: 50) |

In embodiment (24), the second targeting agent and the second targeting agent complement comprise a pair of oligonucleotides, wherein the pair is selected from:

| pair # | Sequence (5'-3') |
|--------|------------------|
| 1 | acatcggtagtt (SEQ ID NO: 1) |
| | aactaccgatgt (SEQ ID NO: 2) |

-continued

| pair # | Sequence (5'-3') |
|--------|------------------|
| 2 | acgtcccagttg (SEQ ID NO: 3) |
| | caactgggacgt (SEQ ID NO: 4) |
| 3 | agaagaagatcc (SEQ ID NO: 5) |
| | ggatcttcttct (SEQ ID NO: 6) |
| 4 | aggttcagtgca (SEQ ID NO: 7) |
| | tgcactgaacct (SEQ ID NO: 8) |
| 5 | atcaggatacgc (SEQ ID NO: 9) |
| | gcgtatcctgat (SEQ ID NO: 10) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 10 | catccaatccag (SEQ ID NO: 19) |
| | ctggattggatg (SEQ ID NO: 20) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 14 | cttacaacgcca (SEQ ID NO: 27) |
| | tggcgttgtaag (SEQ ID NO: 28) |
| 15 | ctttctcggcac (SEQ ID NO: 29) |
| | gtgccgagaaag (SEQ ID NO: 30) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |
| 18 | gctaattcacca (SEQ ID NO: 35) |
| | tggtgaattagc (SEQ ID NO: 36) |
| 19 | ggtcgtgtttca (SEQ ID NO: 37) |
| | tgaaacacgacc (SEQ ID NO: 38) |
| 20 | gttgattctgtc (SEQ ID NO: 39) |
| | gacagaatcaac (SEQ ID NO: 40) |

-continued

| pair # | Sequence (5'-3') |
|--------|------------------|
| 21 | tacccggaataa (SEQ ID NO: 41) |
| | ttattccgggta (SEQ ID NO: 42) |
| 22 | tgcttgacttgg (SEQ ID NO: 43) |
| | ccaagtcaagca (SEQ ID NO: 44) |
| 23 | ttccacttaggg (SEQ ID NO: 45) |
| | ccctaagtggaa (SEQ ID NO: 46) |
| 24 | ttgtctagcggc (SEQ ID NO: 47) |
| | gccgctagacaa (SEQ ID NO: 48) |
| 25 | tttcccttgcta (SEQ ID NO: 49) |
| | tagcaagggaaa (SEQ ID NO: 50) |

In another specific example of embodiment (24), the first targeting agent and the first targeting agent complement comprise a pair of oligonucleotides, wherein the pair is selected from:

| Pair | Sequence |
|------|----------|
| 1 | acatcggtagtt (SEQ ID NO: 1) |
| | aactaccgatgt (SEQ ID NO: 2) |
| 3 | agaagaagatcc (SEQ ID NO: 5) |
| | ggatcttcttct (SEQ ID NO: 6) |
| 6 | atcattaccacc (SEQ ID NO: 11) |
| | ggtggtaatgat (SEQ ID NO: 12) |
| 7 | attaacgggagc (SEQ ID NO: 13) |
| | gctcccgttaat (SEQ ID NO: 14) |
| 8 | cagaggtcttaa (SEQ ID NO: 15) |
| | ttaagacctctg (SEQ ID NO: 16) |
| 9 | caggtgtccatt (SEQ ID NO: 17) |
| | aatggacacctg (SEQ ID NO: 18) |
| 11 | cctacgatatac (SEQ ID NO: 21) |
| | gtatatcgtagg (SEQ ID NO: 22) |
| 12 | cgaatgtagagt (SEQ ID NO: 23) |
| | actctacattcg (SEQ ID NO: 24) |
| 13 | cggtttgagata (SEQ ID NO: 25) |
| | tatctcaaaccg (SEQ ID NO: 26) |
| 16 | gacataaagcga (SEQ ID NO: 31) |
| | tcgctttatgtc (SEQ ID NO: 32) |
| 17 | gccatagtctct (SEQ ID NO: 33) |
| | agagactatggc (SEQ ID NO: 34) |
| 18 | gctaattcacca (SEQ ID NO: 35) |
| | tggtgaattagc (SEQ ID NO: 36) |

-continued

| Pair | Sequence |
|------|----------|
| 20 | gttgattctgtc (SEQ ID NO: 39) |
| | gacagaatcaac (SEQ ID NO: 40) |
| 23 | ttccacttaggg (SEQ ID NO: 45) |
| | ccctaagtggaa (SEQ ID NO: 46) |
| 25 | tttcccttgcta (SEQ ID NO: 49) |
| | tagcaagggaaa (SEQ ID NO: 50) |

Embodiment (24) can also include one or more of the following: the first targeting agent and the first targeting agent complement comprise a first oligonucleotide and a first complementary oligonucleotide, respectively, and the first oligonucleotide and the first complementary oligonucleotide each comprise approximately 10 to 50 bases; the first targeting agent and the first targeting agent complement comprise a first oligonucleotide and a first complementary oligonucleotide, respectively, and the first oligonucleotide and the first complementary oligonucleotide each comprise approximately 10 to 25 bases; the first binding reagent is an antibody comprising a biotin molecule and the first targeting agent comprises a first oligonucleotide including a streptavidin molecule and the linking complex is formed by a reaction between the biotin and streptavidin molecules; the second binding reagent is an antibody comprising an additional biotin molecule and the second targeting agent comprises a second oligonucleotide including an additional streptavidin molecule and the linking complex is formed by a reaction between the additional biotin and the additional streptavidin molecules; the second targeting agent and the second targeting agent complement comprise a second oligonucleotide and a second complementary oligonucleotide, respectively, and the second oligonucleotide and the second complementary oligonucleotide each comprise approximately 10 to 50 bases; the second targeting agent and the second targeting agent complement comprise a second oligonucleotide and a second complementary oligonucleotide, respectively, and the second oligonucleotide and the second complementary oligonucleotide each comprise approximately 10 to 25 bases; and/or the second binding reagent is an antibody comprising a biotin molecule and the second targeting agent comprises a second oligonucleotide including a streptavidin molecule and the linking complex is formed by a reaction between the biotin and streptavidin molecules.

In any one or more of the preceding embodiments, the amount of the first binding reagent on the second binding domain can be <1% the amount of the first binding reagent on the first binding domain.

Embodiment (25): a kit comprising: a multi-well plate having one or more copies of an oligonucleotide array within at least one well(s) of the plate, the array is positioned on a plurality of binding domains, wherein at least 4 of the binding domains have immobilized thereon a different oligonucleotide sequence selected from:

```
                          (SEQ ID NO: 1)
acatcggtagtt (SEQ ID NO: 2)
aactaccgatgt (SEQ ID NO: 3)
acgtcccagttg (SEQ ID NO: 4)
caactgggacgt (SEQ ID NO: 5)
agaagaagatcc (SEQ ID NO: 6)
ggatcttcttct (SEQ ID NO: 7)
aggttcagtgca (SEQ ID NO: 8)
tgcactgaacct (SEQ ID NO: 9)
atcaggatacgc (SEQ ID NO: 10)
gcgtatcctgat (SEQ ID NO: 11)
atcattaccacc (SEQ ID NO: 12)
ggtggtaatgat (SEQ ID NO: 13)
attaacgggagc (SEQ ID NO: 14)
gctcccgttaat (SEQ ID NO: 15)
cagaggtcttaa (SEQ ID NO: 16)
ttaagacctctg (SEQ ID NO: 17)
caggtgtccatt (SEQ ID NO: 18)
aatggacacctg (SEQ ID NO: 19)
catccaatccag (SEQ ID NO: 20)
ctggattggatg (SEQ ID NO: 21)
cctacgatatac (SEQ ID NO: 22)
gtatatcgtagg (SEQ ID NO: 23)
cgaatgtagagt (SEQ ID NO: 24)
actctacattcg (SEQ ID NO: 25)
cggtttgagata (SEQ ID NO: 26)
tatctcaaaccg (SEQ ID NO: 27)
cttacaacgcca
```

-continued

```
                          (SEQ ID NO: 28)
tggcgttgtaag (SEQ ID NO: 29)
ctttctcggcac (SEQ ID NO: 30)
gtgccgagaaag (SEQ ID NO: 31)
gacataaagcga (SEQ ID NO: 32)
tcgctttatgtc (SEQ ID NO: 33)
gccatagtctct (SEQ ID NO: 34)
agagactatggc (SEQ ID NO: 35)
gctaattcacca (SEQ ID NO: 36)
tggtgaattagc (SEQ ID NO: 37)
ggtcgtgtttca (SEQ ID NO: 38)
tgaaacacgacc (SEQ ID NO: 39)
gttgattctgtc (SEQ ID NO: 40)
gacagaatcaac (SEQ ID NO: 41)
tacccggaataa (SEQ ID NO: 42)
ttattccgggta (SEQ ID NO: 43)
tgcttgacttgg (SEQ ID NO: 44)
ccaagtcaagca (SEQ ID NO: 45)
ttccacttaggg (SEQ ID NO: 46)
ccctaagtggaa (SEQ ID NO: 47)
ttgtctagcggc (SEQ ID NO: 48)
gccgctagacaa (SEQ ID NO: 49)
tttcccttgcta (SEQ ID NO: 50)
tagcaagggaaa
``` wherein each of the different oligonucleotide sequences is modified with a linking agent.

Embodiment (26): a kit comprising: a multi-well plate having one or more copies of an oligonucleotide array within at least one well(s) of the plate, the array is positioned on a plurality of binding domains, wherein at least 4 of the binding domains have immobilized thereon a different oligonucleotide sequence selected from:

| Pair | Sequence | |
|------|----------|---|
| 1 | acatcggtagtt | (SEQ ID NO: 1) |
| | aactaccgatgt | (SEQ ID NO: 2) |
| 3 | agaagaagatcc | (SEQ ID NO: 5) |
| | ggatcttcttct | (SEQ ID NO: 6) |
| 6 | atcattaccacc | (SEQ ID NO: 11) |
| | ggtggtaatgat | (SEQ ID NO: 12) |
| 7 | attaacgggagc | (SEQ ID NO: 13) |
| | gctcccgttaat | (SEQ ID NO: 14) |
| 8 | cagaggtcttaa | (SEQ ID NO: 15) |
| | ttaagacctctg | (SEQ ID NO: 16) |
| 9 | caggtgtccatt | (SEQ ID NO: 17) |
| | aatggacacctg | (SEQ ID NO: 18) |
| 11 | cctacgatatac | (SEQ ID NO: 21) |
| | gtatatcgtagg | (SEQ ID NO: 22) |
| 12 | cgaatgtagagt | (SEQ ID NO: 23) |
| | actctacattcg | (SEQ ID NO: 24) |
| 13 | cggtttgagata | (SEQ ID NO: 25) |
| | tatctcaaaccg | (SEQ ID NO: 26) |
| 16 | gacataaagcga | (SEQ ID NO: 31) |
| | tcgctttatgtc | (SEQ ID NO: 32) |
| 17 | gccatagtctct | (SEQ ID NO: 33) |
| | agagactatggc | (SEQ ID NO: 34) |
| 18 | gctaattcacca | (SEQ ID NO: 35) |
| | tggtgaattagc | (SEQ ID NO: 36) |
| 20 | gttgattctgtc | (SEQ ID NO: 39) |
| | gacagaatcaac | (SEQ ID NO: 40) |
| 23 | ttccacttaggg | (SEQ ID NO: 45) |
| | ccctaagtggaa | (SEQ ID NO: 46) |
| 25 | tttcccttgcta | (SEQ ID NO: 49) |
| | tagcaagggaaa | (SEQ ID NO: 50) |

Embodiments (25) and (26) can include one or more of the following elements: the linking agent comprises a biotin, streptavidin, avidin, amino group, thiol group, aldehyde group, hydrazide group, azide group, alkyne group, maleimide group or iodoacetamide group; the linking agent is streptavidin; the kit further includes, in one or more separate vials, containers, or compartments, (a) a set of binding reagent pairs, wherein each binding reagent of the set is specific for an analyte in a sample comprising a plurality of analytes, wherein optionally, a binding reagent pair within the set comprises a first binding reagent comprising a supplemental linking agent, and still further optionally the kit further includes, in one or more separate vials, containers, or compartments, a supplemental linking agent. In one example, the binding reagent is an antibody.

The kits of the preceding embodiments, e.g., embodiments (25) and (26), can further include, in one or more separate vials, containers, or compartments, a labeling kit, as well as one or more additional reagents comprising: an assay buffer, diluent, read buffer, or combinations thereof. The labeling kit can include, in one or more separate vials, containers, or compartments, SULFO-TAG™ NHS ester, LC-biotin NHS ester, a spin column, a labeling buffer solution, ECL read buffer, assay and antibody buffers, assay and antibody diluents, or combinations thereof.

In embodiments (25) and (26), the array comprises at least 7 binding domains, or at least 10 binding domains, or at least 16 binding domains, or at least 25 binding domains. Moreover, the plate can include at least 24 wells, or at least 96 wells, or at least 384 wells. The array can also include at least 10 oligonucleotides, or at least 16 oligonucleotides, or at least 25 oligonucleotides.

In a specific example of any one of the preceding embodiments, the number of binding reagent pairs in the set is equivalent to the number of binding domains in the array, or the number of binding reagent pairs in the set is less than the number of binding domains in the array.

BRIEF DESCRIPTION OF DRAWINGS

The accompanying drawings are provided to illustrate rather than limit the scope of the invention.

FIGS. 1(a)-(d) illustrate an assay format comprising the direct conjugation of binding reagents, A', B', and C', to a plurality of binding domains, X, Y, and Z, respectively, via reactions between targeting agents, A'', B'', and C'', and targeting agent complements, A''', B''', and C''', respectively. The targeting agents are attached to binding reagents, A', B', and C', on a series of binding domains, X, Y, and Z, to form binding reagent complexes, $A_{RC}$, $B_{RC}$, and $C_{RC}$, respectively (panel (b)), which react with analytes A, B, and C, respectively. The presence of analytes A, B, and C on the solid support is detected by the addition of labeled detection reagents, A*, B*, and C*, which react with analytes, A, B, and C, respectively (panel (c)). FIG. 1(d) is an enlarged view of the binding reagent complexes formed on binding domains X, Y, and Z, binding reagent complexes $A_{RC}$, $B_{RC}$, and $C_{RC}$, respectively.

FIGS. 2(a)-(d) illustrates an assay format comprising the direct conjugation of binding reagents, e.g., antibodies, A', B', and C', to a plurality of binding domains, X, Y, and Z, respectively, via reactions between oligonucleotide targeting agents, A'', B'', and C'', and oligonucleotide targeting agent complements, A''', B''', and C''', respectively. The oligonucleotide targeting agents are attached to binding reagents, A', B', and C', on a series of binding domains, X, Y, and Z, to form binding reagent complexes, $A_{RC}$, $B_{RC}$, and $C_{RC}$, respectively (panel (b)), which react with analytes A, B, and C, respectively. The presence of analytes A, B, and C on the solid support is detected by the addition of labeled detection reagents, A*, B*, and C*, which react with analytes, A, B, and C, respectively (panel (c)). FIG. 2(d) is an enlarged view of the binding reagent complexes formed on binding domains X, Y, and Z, binding reagent complexes $A_{RC}$, $B_{RC}$, and $C_{RC}$, respectively.

FIGS. 3(a)-(e) illustrates an assay format involving the conjugation of a plurality of binding reagents, A', B', and C', to a plurality of binding domains, X, Y, and Z, respectively, via a series of linking complexes. As shown in panel (a), binding reagents A', B', and C' are attached to linking agents, $L_A$, $L_B$, and $L_C$, while targeting agents A'', B'', and C' are attached to supplemental linking agents, $L_A'$, $L_B'$, and $L_C'$, respectively. Binding reagents A', B', and C' are mixed with targeting agents to form binding reagent complexes, $A_{RC}$, $B_{RC}$, and $C_{RC}$, respectively. The binding reagent complexes formed in panel (a) are mixed with a plurality of binding domains, X, Y, and Z, to which targeting agent complements, A''', B''', and C''' are bound (panel (b)) to adhere the binding reagent complexes to the binding domains (see panel (c)). A sample comprising analytes A, B, and C, is added to the mixture, and simultaneously or sequentially, a set of detection reagents, A*, B*, and C* are also added to detect analytes bound to the binding domains. FIG. 3(e) is an enlarged view of the binding reagent complexes formed on binding domains X, Y, and Z, binding reagent complexes $A_{RC}$, $B_{RC}$, and $C_{RC}$, respectively.

FIGS. 4(a)-(e) illustrates an assay format involving the conjugation of a plurality of binding reagents, A', B', and C', to a plurality of binding domains, X, Y, and Z, respectively, via a series of linking complexes. As shown in panel (a), binding reagents A', B', and C' are attached to linking agents, $L_A$, $L_B$, and $L_C$, while oligonucleotide targeting agents A'', B'', and C' are attached to supplemental linking agents, $L_A'$, $L_B'$, and $L_C'$, respectively. Binding reagents A', B', and C' are mixed with oligonucleotide targeting agents to form binding reagent complexes, $A_{RC}$, $B_{RC}$, and $C_{RC}$, respectively. The binding reagent complexes formed in panel (a) are mixed with a plurality of binding domains, X, Y, and Z, to which oligonucleotide targeting agent complements, A''', B''', and C''' are bound (panel (b)) to adhere the binding reagent complexes to the binding domains (see panel (c)). A sample comprising analytes A, B, and C, is added to the mixture, and simultaneously or sequentially, a set of detection reagents, A*, B*, and C* are also added to detect analytes bound to the binding domains. FIG. 4(e) is an enlarged view of the binding reagent complexes formed on binding domains X, Y, and Z, binding reagent complexes $A_{RC}$, $B_{RC}$, and $C_{RC}$, respectively.

In FIG. 5(a), all reagents are mixed with the sample in a single step, whereas in FIG. 5(b), all reagents are mixed and then added to the surface, and in 5(c), modified binding reagents and modified targeting agent complements are mixed, added to a surface bearing a plurality of binding domains each including a targeting agent, and the surface-mixture is mixed with the sample and detection reagents in one step or two (one step addition of sample and detection reagents is shown in FIG. 5(c) and the sequential addition of sample and detection reagents is shown in FIG. 5(d).

FIGS. 6(a)-(f) show various modified surfaces, e.g., particles and substrates bearing a plurality of binding domains that can be used in the assay format of the invention.

FIGS. 8(a)-(g) show the results of a direct assay format on a 7-plex chemokine panel and a 10-plex TH1/TH2 panel.

FIGS. 9(a)-(c) show a procedure for the production and use of a multi-well assay plate in an indirect assay format using biotinylated capture antibodies with oligonucleotide modified with streptavidin molecules.

FIGS. 10(a)-(c) show a procedure for the production and use of a multi-well assay plate in an indirect assay format using biotinylated capture antibodies, neat streptavidin, and biotinylated oligonucleotides.

FIGS. 11(a)-(g) show a comparison of LOD values for three different oligonucleotide-mediated assay formats for a cytokine B panel.

DETAILED DESCRIPTION OF THE INVENTION

Figure 1D:
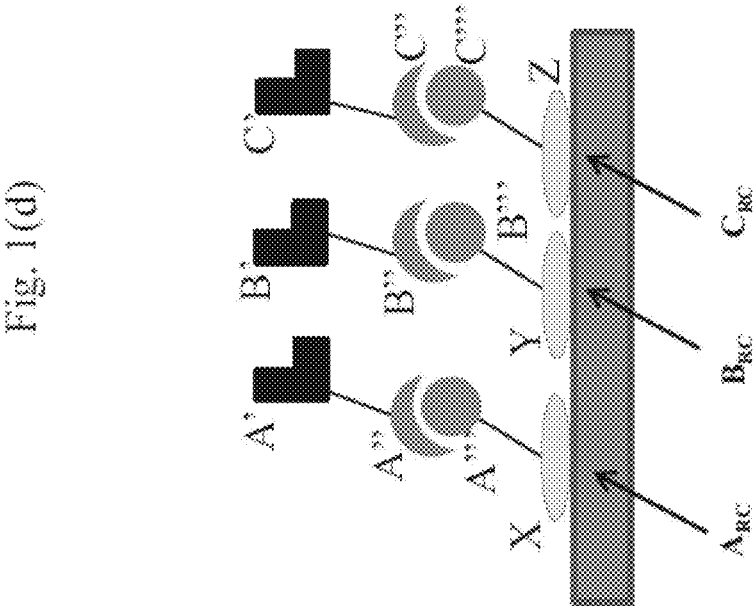

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention provides flexible solid phase binding assay formats that allow a user or manufacturer to configure an assay based on specific user requirements. The methods and kits described herein provide a flexible platform for creating a multiplexed binding assay for a plurality of target analytes. With a support including a plurality of binding domains bearing a series of generic targeting agent complements, it is possible to configure a multiplexed assay for any set of analytes. One only needs to select which analytes will be evaluated in which binding domain and pair the appropriate binding reagents and targeting agents with each selected binding domain. Using this platform, a user can build a personalized assay panel.

Such flexible multiplexed assay formats can be achieved using the methods and products disclosed herein. For example, a method of conducting a multiplexed binding assay for a plurality of analytes of interest can be implemented using the following steps:

(a) combining, in one or more steps, the following components:
(i) a sample comprising a first analyte of interest and a second analyte of interest,
(ii) a first targeting agent immobilized on a first binding domain,
(iii) a first targeting agent complement connected to a linking agent, wherein the first targeting agent complement is a binding partner of the first targeting agent,
(iv) a first binding reagent connected to a supplemental linking agent, wherein the first binding reagent is a binding partner of the first analyte,
(v) a second targeting agent immobilized on a second binding domain,
(vi) a second targeting agent complement connected to a linking agent, wherein the second targeting agent complement is a binding partner of the second targeting agent,
(vii) a second binding reagent connected to a supplemental linking agent, wherein the second binding reagent is a binding partner of the second analyte, and
(viii) optionally, at least two copies of a bridging agent, wherein, if the bridging agent is omitted, each linking agent is a binding partner of the supplemental linking agent, or if the bridging agent is included, the bridging agent has a first binding site for one of the linking agents and an additional binding site for one of the supplemental linking agents;

(b) forming (i) a first binding complex on the first binding domain comprising the first targeting agent, the first targeting agent complement, the first binding reagent and the first analyte, and (ii) a second binding complex on the second binding domain comprising the second targeting agent, the second targeting agent complement, the second binding reagent and the second analyte, and (c) measuring the amount of the first and second analytes on the first and second binding domains, respectively.

In one embodiment, if a bridging agent is not used, the method includes (a) combining components (i)-(vii) in one or more steps, (b) forming the first and second binding complexes on the first and second binding domains, respectively, and (c) measuring the amount of the first and second analytes on the first and second binding domains, respectively. For example, the first targeting agent complement and the first binding reagent can be provided as a pre-bound first targeting complex including the first targeting agent complement and the first binding reagent linked through a binding interaction between the linking agent and supplemental linking agent; and likewise, the second targeting agent complement and the second binding reagent can be provided as a pre-bound second targeting complex comprising the second targeting agent complement and the second binding reagent linked through a binding interaction between the linking agent and supplemental linking agent. In this embodiment, the first targeting complex can be provided pre-bound to the first targeting agent immobilized on the first binding domain; and likewise, the second targeting complex can be provided pre-bound to the second targeting agent immobilized on the second binding domain. When the first and second binding reagents are provided in pre-bound targeting complexes, the combining step may further includes combining the first and second targeting complexes with the sample to form a mixture thereof, binding the first analyte to the first binding reagent in the first targeting complex and binding the second analyte to the second binding reagent in the second targeting complex, contacting a mixture of the first and second targeting complexes bound to first and second analytes, respectively, with the first and second binding domains. The binding complexes on the first and second binding domains are thereby formed by binding the first targeting complex to the first targeting agent on the first binding domain and binding the second targeting complex to the second targeting agent on the second binding domain. Moreover, the combining step can further include combining the first and second targeting complexes with the sample; and binding the first analyte to the first binding reagent in the first targeting complex and binding the second analyte to the second binding reagent in the second targeting complex.

In another alternative embodiment, the combining step (a) includes the steps of combining, in a first volume of liquid, said first targeting agent complement, said first binding reagent and, if used, said bridging reagent and linking said first targeting agent complement and said first binding reagent through their attached linking agents to form a first targeting complex; and combining, in a second volume of liquid, said second targeting agent complement, said second binding reagent and, if used, said bridging reagent and linking said second targeting agent complex complement and said second binding reagent through their attached linking agents to form a second targeting complex. In this embodiment, the combining step (a) can also include the steps of combining said first and second targeting complexes, contacting the combination of said first and second targeting complexes with said first and second binding domains, and binding said first targeting complex to said first targeting agent on said first binding domain and binding said second targeting complex to said second targeting agent on said second binding domain. In this embodiment, the combining step further includes combining the combination of the first and second targeting complexes with the sample and binding the first analyte to the first binding reagent in the first targeting complex and binding the second analyte to the second binding reagent in the second targeting complex. The first and second targeting complexes can be combined with the sample prior to contacting the first and second targeting complexes with the first and second binding domains; the first and second targeting complexes can be combined with the sample after contacting the first and second targeting complexes with the first and second binding domains; or the first and second targeting complexes can be combined with the sample and contacted with the first and second binding domains at the same time.

If a bridging agent is included in the method, then the linking agent and supplemental linking agents each bind to the bridging agent, and the combining step therefore brings those elements attached to the linking agents and supplemental linking agents together. For example, the combining step (a) includes combining, in a first volume of liquid, (xi) the first targeting agent complement, the first binding reagent and the bridging reagent and further includes forming the first targeting complex by linking the first targeting agent complement and the first binding reagent through a bridging complex including the linking agent bound to the bridging agent to which the supplemental linking agent is bound. Combining step (a) also includes combining, in a second volume of liquid, (xii) the second targeting agent complement, the second binding reagent and the bridging reagent and further includes forming the second targeting complex by linking the second targeting agent complement and the second binding reagent through a bridging complex including the linking agent bound to the bridging agent to which the supplemental linking agent is bound. In this embodiment, the combining step (a) can also include combining (xiii) the first and second targeting complexes, and combining the combination of the first and second targeting complexes with the first and second binding domains, and binding the first targeting complex on the first binding domain and binding the second targeting complex on the second binding domain. In this embodiment, the combining step further includes combining (xiv) the first and second targeting complexes with the sample and binding the first analyte to the first binding reagent in the first targeting complex and binding the second analyte to the second binding reagent in the second targeting complex. The first and second targeting complexes can be combined with the sample prior to contacting the first and second targeting complexes with the first and second binding domains; the first and second targeting complexes can be combined with the sample after contacting the first and second targeting complexes with the first and second binding domains; or the first and second targeting complexes can be combined with the sample and contacted with the first and second binding domains at the same time.

The methods described herein can be used to multiplex a plurality of analytes of interest in a sample. In this regard, the sample contains one or more additional analytes of interest and for each additional analyte of interest, the combining step (a) further comprises combining, in one or more steps, (ix) an additional targeting agent immobilized on an additional binding domain, an additional targeting agent complement connected to a linking agent, and an additional binding reagent connected to a supplemental linking agent, and (x) an additional binding complex on the additional binding domain comprising the additional targeting agent, the additional targeting agent complement, the additional binding reagent and the additional analyte; the forming step (b) further comprises forming (iii) an additional binding complex on the additional binding domain comprising the additional targeting agent, the additional targeting agent complement, the additional binding reagent and the additional analyte; and the measurement in step (c) further comprises measuring the amount of the additional analyte on the additional binding domain.

In a specific embodiment, the invention includes a method of conducting a binding assay for a plurality of analytes comprising (a) contacting a sample with two or more binding domains linked to at least a first and second binding reagent that each bind a first and second analyte, respectively, of the plurality of analytes to form complexes comprising the first analyte bound to the first binding reagent and the second analyte bound to the second binding reagent, wherein (x) the first binding domain comprises a first binding reagent complex comprising (i) a first targeting agent bound to the first binding domain and to a first targeting agent complement; and (ii) the first binding reagent bound to the first targeting agent complement via a linking complex; and (y) the second binding domain comprises a second binding reagent complex comprising (i) a second targeting agent bound to the second binding domain and to a second targeting agent complement; and (ii) the second binding reagent bound to the second targeting agent complement via a linking complex; (b) contacting the first and second binding reagent complexes with a plurality of detection reagents comprising a first detection reagent that binds the first analyte or a complex comprising the first analyte, and a second detection reagent that binds the second analyte or a complex comprising the second analyte; and (c) measuring the amount of the first and second analytes bound to the two or more binding domains.

In another specific embodiment, the method includes: (a) forming a first binding reagent complex comprising a first binding reagent specific for a first analyte in the plurality of analytes and a first targeting agent, wherein the first binding reagent is bound to a linking agent and the first targeting agent is bound to a supplemental linking agent wherein the first binding reagent complex is formed by a reaction between the linking agent and the supplemental linking agent; (b) forming a second binding reagent complex comprising a second binding reagent specific for a second analyte in the plurality of analytes and a second targeting agent, wherein the second binding reagent is bound to a second linking agent and the second targeting agent is bound to a second linking agent complement wherein the second binding reagent complex is formed by a reaction between the second linking agent and the second linking agent complement; (c) mixing the first and second binding reagent complexes with two or more binding domains each linked to a first targeting agent complement and a second targeting agent complement, respectively, under conditions sufficient to bind the first targeting agent to the first targeting agent complement and the second targeting agent to the second targeting agent complement; (d) mixing a sample comprising the plurality of analytes to the mixture formed in step (c); (e) adding a plurality of additional binding reagents to the mixture formed in step (d), wherein the plurality of additional binding reagents includes (i) a first detection reagent specific for the first analyte and/or a first binding reagent-first analyte complex; and (ii) a second detection reagent specific for the second analyte and/or a second binding reagent-second analyte complex; and (f) measuring the amount of the first and second analytes bound to the binding domains.

A further specific embodiment includes (a) forming a first binding reagent complex comprising a first binding reagent specific for a first analyte in the plurality of analytes and a first targeting agent, wherein the first binding reagent is bound to a linking agent and the first targeting agent is bound to a supplemental linking agent wherein the first binding reagent complex is formed by a reaction between the linking agent and the supplemental linking agent; (b) forming a second binding reagent complex comprising a second binding reagent specific for a second analyte in the plurality of analytes and a second targeting agent, wherein the second binding reagent is bound to a second linking agent and the second targeting agent is bound to a second linking agent complement wherein the second binding reagent complex is formed by a reaction between the second linking agent and the second linking agent complement; (c) mixing the first and second binding reagent complexes and the sample with two or more binding domains each linked to a first targeting agent complement and a second targeting agent complement, respectively, under conditions sufficient to bind the first targeting agent to the first targeting agent complement and the second targeting agent to the second targeting agent complement; (d) adding a plurality of additional binding reagents to the mixture formed in step (c), wherein the plurality of additional binding reagents includes (i) a first detection reagent specific for the first analyte and/or a first binding reagent-first analyte complex; and (ii) a second detection reagent specific for the second analyte and/or a second binding reagent-second analyte complex; and (e) measuring the amount of the first and second analytes bound to the binding domains.

Specific embodiments of the method of the present invention are illustrated in FIGS. 3-6. FIGS. 1 and 2 illustrate a direct assay method that does not involve a linking complex. These figures are provided for comparative purposes. FIG. 1 illustrates a direct multiplexed assay for analytes A, B, and C. Binding reagents specific for these analytes, A', B', and C', respectively, are attached to targeting agents, A", B", and C". A solution including these binding reagents attached to their corresponding targeting agents is mixed with a solid phase to which targeting agent complements A''', B''', and C''', respectively are bound to a series of discrete binding domains. The binding reagents are adsorbed to the surface to form binding reagent complexes, $A_{RC}$, $B_{RC}$, and $C_{RC}$, each binding reagent affixed via the targeting agent complements to a discrete binding domain on the surface. The surface is contacted with a sample comprising analytes A, B, and C, as well as detection binding reagents, A*, B*, and C*, which are capable of binding to analytes A, B, and C, respectively, and/or a complex comprising those analytes. The detection binding reagents include a detectable label. Alternatively, the surface is contacted with a sample comprising the plurality of analytes and subsequently contacted with a mixture of detection binding reagents. Once the detection binding reagents are bound to the surface, and optionally, the surface is washed to remove unbound reagents, the presence of each analyte is detected via the detection reagents bound to each discrete binding domain. FIG. 2 illustrates a specific embodiment of FIG. 1 involving the use of antibodies as binding reagents and oligonucleotide-complementary oligonucleotide pairs as targeting agent/targeting agent complement pairs. It will be evident to the skilled artisan that the direct methods illustrated in FIGS. 1 and 2 are not configurable by the user. Each individual binding domain includes a predetermined targeting agent complement, such that only a single binding reagent-targeting agent can bind to a single binding domain in the array.

Figure 3E:
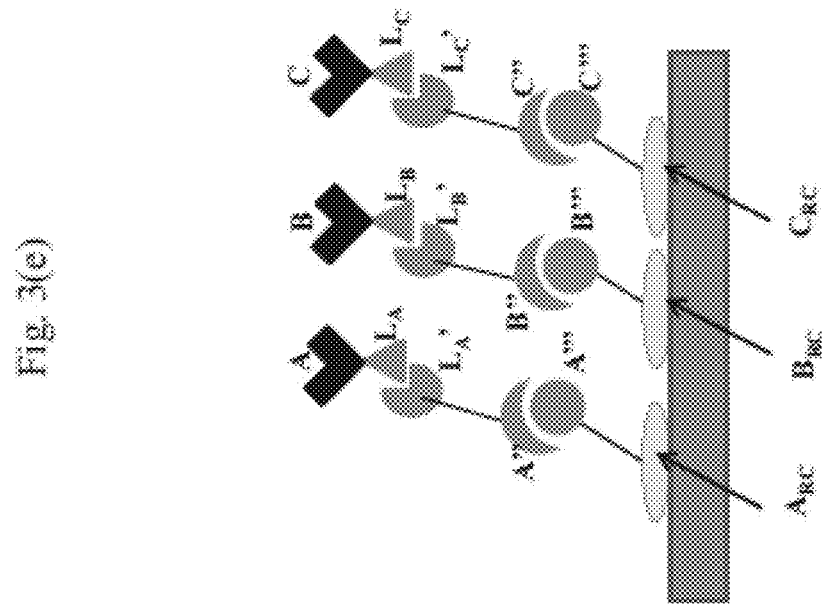
Figure 4E:
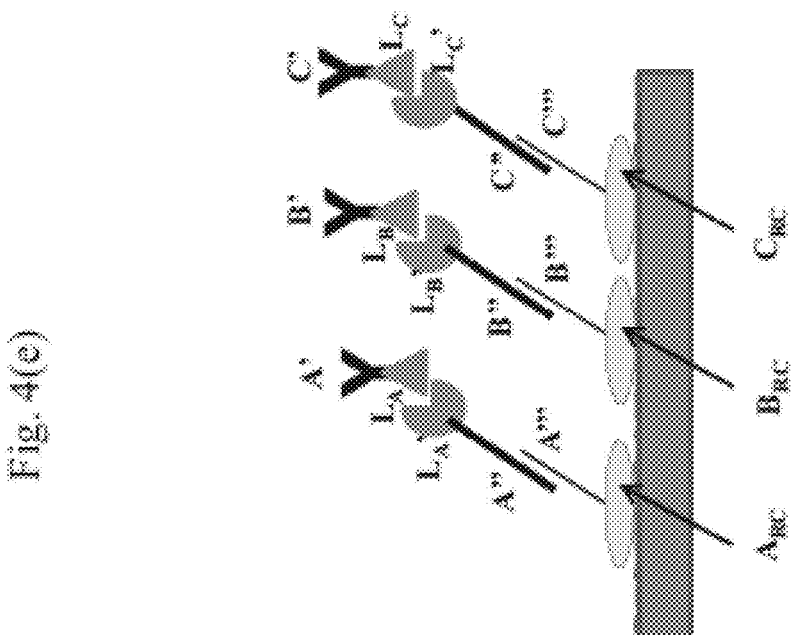

FIGS. 3-4 illustrate particular embodiments of the instant invention that offer the user optimal flexibility in a user-defined assay configuration. FIG. 3 illustrates an indirect binding format for analytes A, B, and C, incorporating a series of linking complexes that allow the user to tailor the assay for his/her needs. FIG. 3(*a*)-(*b*) illustrates a general approach for making the targeting complexes of the invention: a series of solutions are formed that include one of the binding reagents (A', B', and C') bound to a linking agents ($L_A$, $L_B$, and $L_C$, respectively). The solutions also include the corresponding targeting agents, (A" for A', B" for B', and C"' for C'), bound to a supplemental linking agent ($L_A'$, $L_B'$, and $L_C'$, respectively). The solutions are mixed to form the mixture of binding reagent-linking complex-targeting agent complexes shown in panel (b). An advantage of this approach is that it does not require the linking reagents for each targeting complex to be non-cross reactive and, in fact, allows the linking agents to be used in each targeting complex (i.e., $L_A=L_B=L_C$ and $L_A'=L_B'=L_C'$). In one embodiment illustrated in FIG. 3(*c*)-(*e*) the mixture of binding reagent-linking complex-targeting agent complexes are mixed with a surface comprising a plurality of discrete binding domains to which targeting agent complements, A''', B''', and C''' are bound. The binding reagent-linking complex-targeting agent complexes are adsorbed to form binding reagent complexes, $A_{RC}$, $B_{RC}$, and $C_{RC}$ as shown in panel (c). An expanded view of the binding reagent complexes is shown in FIG. 3(*e*). The surface is contacted with a sample comprising analytes A, B, and C, as well as detection binding reagents, A*, B*, and C*, which are capable of binding to analytes A, B, and C, respectively, and/or a complex comprising those analytes. The detection binding reagents include a detectable label. Alternatively, the surface is contacted with a sample comprising the plurality of analytes and subsequently contacted with a mixture of detection binding reagents. Once the detection binding reagents are bound to the surface, and optionally, the surface is washed to remove unbound reagents, the presence of each analyte is detected via the detection reagents bound to each discrete binding domain (panel 3(d)). FIG. 4 illustrates a specific embodiment of FIG. 3 involving the use of antibodies as binding reagents and oligonucleotide-complementary oligonucleotide pairs as targeting agent/targeting agent complement pairs. As noted for FIG. 3, the linking agents for each binding reagent may be the same and the linking agent complements for each targeting agent may be the same.

The skilled artisan will readily appreciate that various permutations of the assay format depicted in FIGS. 3-4 are possible. Certain preferred embodiments are depicted in FIG. 5(*a*)-(*c*). For example, all of the reagents, i.e., binding reagents modified by supplemental linking agents, targeting agent complements modified by linking agents, detection reagents and sample, can be mixed together with the surface bearing targeting agent-modified binding domains in a single step to form the complexes shown in FIGS. 3(*d*) and 4(*d*), optionally washed, and analyzed for the presence of analytes A, B, and C, bound to the surface (FIG. 5(*a*)). Alternatively, binding reagents modified by supplemental linking agents, and targeting agents modified by linking agents can be mixed in a single step, added to the surface having targeting agent-modified binding domains in a subsequent step, sample and detection reagents are added, and analyzed in a final step (FIG. 5(*b*)). In yet another embodiment, binding reagents modified by supplemental linking agents, and targeting agent complements modified by linking agents can be mixed, added to the surface bearing targeting agents in discrete binding domains, mixed with sample, and then detection reagents are added (FIG. 5(*c*)). Individual analyte solutions can be added to each binding domain sequentially or simultaneously in a single mixture, and likewise, individual detection reagents can be added to each binding domain sequentially or simultaneously in a single mixture. Any surface binding step can optionally be followed by a washing step to remove any unbound components of the assay before proceeding to the next step.

The invention also provides kits, components, and consumables that can be used to practice the methods described herein. The following materials/methods are used in the instant invention.

(i) Samples/Analytes

Examples of samples that may be analyzed by the methods of the present invention include, but are not limited to food samples (including food extracts, food homogenates, beverages, etc.), environmental samples (e.g., soil samples, environmental sludges, collected environmental aerosols, environmental wipes, water filtrates, etc.), industrial samples (e.g., starting materials, products or intermediates from an industrial production process), human clinical samples, veterinary samples and other samples of biological origin. Biological samples that may be analyzed include, but are not limited to, feces, mucosal swabs, physiological fluids and/or samples containing suspensions of cells. Specific examples of biological samples include blood, serum, plasma, feces, mucosal swabs, tissue aspirates, tissue homogenates, cell cultures and cell culture supernatants (including cultures of eukaryotic and prokaryotic cells), urine, saliva, sputum, and cerebrospinal fluid.

Analytes that may be measured using the methods of the invention include, but are not limited to proteins, toxins, nucleic acids, microorganisms, viruses, cells, fungi, spores, carbohydrates, lipids, glycoproteins, lipoproteins, polysaccharides, drugs, hormones, steroids, nutrients, metabolites and any modified derivative of the above molecules, or any complex comprising one or more of the above molecules or combinations thereof. The level of an analyte of interest in a sample may be indicative of a disease or disease condition or it may simply indicate whether the patient was exposed to that analyte.

The assays of the present invention may be used to determine the concentration of one or more, e.g., two or more analytes in a sample. Thus, two or more analytes may be measured in the same sample. Panels of analytes that can be measured in the same sample include, for example, panels of assays for analytes or activities associated with a disease state or physiological conditions. Certain such panels include panels of cytokines and/or their receptors (e.g., one or more of TNF-alpha, TNF-beta, IL1-alpha, IL1-beta, IL2, IL4, IL6, IL-10, IL-12, IFN-γ, etc.), growth factors and/or their receptors (e.g., one or more of EGF, VGF, TGF, VEGF, etc.), drugs of abuse, therapeutic drugs, vitamins, pathogen specific antibodies, auto-antibodies (e.g., one or more antibodies directed against the Sm, RNP, SS-A, SS-alpha, J0-1, and Sc1-70 antigens), allergen-specific antibodies, tumor markers (e.g., one or more of CEA, PSA, CA-125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, myoglobin, CKMB, myeloperoxidase, glutathione peroxidase, β-natriuretic protein (BNP), alpha-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (alpha-amyloid, beta-amyloid, Aβ 42, Aβ 40, Aβ 38, Aβ 39, Aβ 37, Aβ 34, tau-protein, etc.), markers of osteoporosis (e.g., one or more of cross-linked Nor C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), lutenizing hormone (LH), prolactin, hCG, testosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in a panel, such as those listed above; e.g., a panel useful for the diagnosis of thyroid disorders may include e.g., one or more of thyroid stimulating hormone (TSH), Total T3, Free T3, Total T4, Free T4, and reverse T3).

The methods of the present invention are designed to allow detection of a wide variety of biological and biochemical agents, as described above. In one embodiment, the methods may be used to detect pathogenic and/or potentially pathogenic virus, bacteria and toxins including biological warfare agents ("BWAs") in a variety of relevant clinical and environmental matrices, including and without limitation, blood, sputum, stool, filters, swabs, etc. A non-limiting list of pathogens and toxins that may be analyzed (alone or in combination) using the methods of the present invention is *Bacillus anthracis* (anthrax), *Yersinia pestis* (plague), *Vibrio cholerae* (cholera), *Francisella tularensis* (tularemia), *Brucella* spp. (Brucellosis), *Coxiella burnetii* (Q fever), *listeria, salmonella, shigella, V. cholera, Chlamydia trachomatis, Burkholderia pseudomallei*, orthopox viruses including variola virus (smallpox), viral encephalitis, Venezuelan equine encephalitis virus (VEE), western equine encephalitis virus (WEE), eastern equine encephalitis virus (EEE), Alphavirus, viral hemorrhagic fevers, Arenaviridae, Bunyaviridae, Filoviridae, Flaviviridae, Ebola virus, staphylococcal enterotoxins, ricin, otulinum toxins (A, B, E), *Clostridium botulinum*, mycotoxin, *Fusarium, Myrotecium, Cephalosporium, Trichoderma, Verticimonosporium, Stachybotrys*, glanders, wheat fungus, *Bacillus globigii, Serratia marcescens*, yellow rain, trichothecene mycotoxins, *Salmonella typhimurium*, aflatoxin, *Xenopsylla cheopis, Diamanus montanus*, alastrim, monkeypox, Arenavirus, Hantavirus, Lassa fever, Argentine hemorrhagic fevers, Bolivian hemorrhagic fevers, Rift Valley fever virus, Crimean-Congo virus, Hanta virus, Marburg hemorrhagic fevers, yellow fever virus, dengue fever viruses, influenza (including human and animal strains including H5N1 avian influenza, influenza A, influenza A, H1 specific, influenza A, H3 specific, influenza A, H5 specific, influenza A, 2009-H1N1 specific, influenza B), RSV, human immunodeficiency viruses I and II (HIV I and II), hepatitis A, hepatitis B, hepatitis C, hepatitis (non-A, B or C), Enterovirus, Epstein-Barr virus, Cytomegalovirus, herpes simplex viruses, *Chlamydia trachomatis, Neisseria gonorrheae, Trichomonas vaginalis*, human papilloma virus, *Treponema pallidum, Streptococcus pneumonia, Borellia burgdorferi, Haemophilus influenzae, Mycoplasma pneumoniae, Chlamydophila pneumoniae, Legionella pneumophila, Staphylococcus aureus, Staphylococcus* Enterotoxin B (SEB), Abrin, Shiga Toxin 1, Shiga Toxin 2, *Moraxella catarrhalis, Streptococcus pyogenes, Clostridium difficile, Neisseria meningitidis, Klebsiella pneumoniae, Mycobacterium tuberculosis*, Group A *streptococcus, E. Coli* 0157, coronavirus, Coxsackie A virus, rhinovirus, parainfluenza virus, respiratory syncytial virus (RSV), metapneumovirus, vaccinia, and adenovirus.

(ii) Binding Reagents

The skilled artisan in the field of binding assays will readily appreciate the scope of binding agents and companion binding partners that may be used in the present methods. A non-limiting list of such pairs include (in either order) oligonucleotides and complements, receptor/ligand pairs, antibodies/antigens, natural or synthetic receptor/ligand pairs, amines and carbonyl compounds (i.e., binding through the formation of a Schiff's base), hapten/antibody pairs, antigen/antibody pairs, epitope/antibody pairs, mimitope/antibody pairs, aptamer/target molecule pairs, hybridization partners, and intercalater/target molecule pairs.

In a preferred embodiment, the binding assays of the methods of the present invention employ antibodies or other receptor proteins as binding reagents. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.*, 67 (Suppl); 51-64 (1966) and Hochman, 1. Inbar, D. and Givol, D. *Biochemistry* 12: 1130 (1973)), as well as antibody constructs that have been chemically modified, e.g., by the introduction of a detectable label.

(iii) Targeting Agents, Linking Agents & Bridging Agents

Binding reagents are linked to components that enable their attachment to each other and/or to solid phases, directly or indirectly. These components are referred to herein as targeting agents and linking agents. As used herein, targeting agents and their complements are used to adhere a binding reagent to a surface or support, whereas linking agents and supplemental linking agents are used to attach a binding reagent to a targeting agent, directly or indirectly through a bridging agent, if one is used.

In one embodiment, a targeting agent and its complement comprise a first oligonucleotide and a complementary oligonucleotide, a receptor-ligand pair, an antigen-antibody pair, a hapten-antibody pair, an epitope-antibody pair, a mimetope-antibody pair, an aptamer-target molecule pair, hybridization partners, or an intercalator-target molecule pair. The targeting agents and complements used in an assay are selected such that the targeting agents and complements associated with a binding reagent for an analyte (for example, a first analyte) measured by the assay are substantially non-cross-reactive with the targeting agents and complements associated with the binding reagents for the other analytes measured by the assay (for example, a second analyte). Accordingly, in an assay of the invention, the binding of a binding reagent to its associated binding domain (through its associated targeting agent and targeting agent complement) should be substantially greater than its binding to binding domains associated with other analytes (and presenting different targeting agent complements). Preferably the cross-reactivity for the binding of binding reagents for an analyte to binding domains associated with other analytes relative to the binding to the correct binding domain is <1%, more preferably <0.1% and more preferably <0.01%. In a preferred embodiment, the targeting agent/targeting agent complement comprise a pair of oligonucleotides including complementary sequences and the targeting agent and its complement are contacted under conditions sufficient to hybridize the targeting agent to its complement.

The preferred length is approximately 5 to 100 bases, preferably, approximately, 10 to 50 bases, and more preferably approximately 10 to 25 bases. In addition, the targeting oligonucleotides sequences need not be identical in length and in certain embodiments it may be beneficial to provide one targeting oligonucleotide sequence that is longer than its binding partner, e.g., by up to 25 bases, or up to 15 bases, or up to 10 bases. Oligonucleotide sequences and their complements can be generated by techniques known in the art for generating pairs of complementary oligonucleotides with similar binding energies (or melting temperatures) and low inter-pair cross-reactivity (e.g., commercial or public software for selecting probes or primers for multiplexed nucleic acid assays). Oligonucleotide sequences can include naturally occurring nucleic acid bases as well as non-naturally occurring and/or modified bases. For example, the oligonucleotide sequences can include Iso-dC and/or Iso-dG, which are chemical variants of cytosine and guanine, respectively, available from EraGen Biosciences, Inc. (www.eragen.com). Incorporation of such modified bases into oligonucleotide sequences effectively expands the genetic alphabet and permits synthesis of oligonucleotides that have increased specificity and decreased mismatch hybridization potential. For example, an oligonucleotide containing Iso-dC can be designed so that it will hybridize to a complementary oligo containing Iso-dG but will not hybridize to any naturally occurring nucleic acids sequence.

In one approach, a computer algorithm can be used to generate oligonucleotide sequence pairs based on one or more, and preferably all, of the following rules: (i) GC content between about 40-60%, e.g., 40-50%; (ii) a maximum string of base repeats in a sequence of no more than three; (iii) a maximum number of base pair matches of six between sequences in different pairs, with no more than four matches in a row; (iv) a rejection of sequences with predicted hairpin loop sizes between 2-5, oligonucleotides if they have four or more base-pair matches in the stem region (loop sizes of six or greater are retained); and (v) a higher free energy)($\Delta G°$) of the specific interactions resulting from a 40-60% or 40-50% GC content ($\Delta G°$ is dependent on temperature and salt concentration, and at 23° C. and 200 mM of a monovalent cation, pH 7.0, $\Delta G°$ preferably exceeds −15 kcal/mol). In a particular embodiment, at least relative GC content and $\Delta G°$ are considered, along with one or more the rules identified above, in oligonucleotide selection. In one embodiment, it may be advantageous to design oligonucleotide sequences that minimize non-specific binding and this can be achieved by a variety of methods. For example, one can design oligonucleotide/oligonucleotide pairs that form no more than three consecutive G/C pairs with other oligonucleotides used in the assay. Alternatively or additionally, one or more of the following configurations can be avoided: formation of single nucleotide loops or single nucleotide mismatches positioned between G/C-rich sequences when paired with other oligonucleotides used in the assay.

In one embodiment, the targeting agent and the targeting agent complement comprise a pair of oligonucleotides, wherein the pair is selected from one of the following sequence pairs in Table 1(a):

| Pair # | Sequence (5'-3') |
|---|---|
| 1 | acatcggtagtt (SEQ ID NO: 1) |
|   | aactaccgatgt (SEQ ID NO: 2) |
| 2 | acgtcccagttg (SEQ ID NO: 3) |
|   | caactgggacgt (SEQ ID NO: 4) |
| 3 | agaagaagatcc (SEQ ID NO: 5) |
|   | ggatcttcttct (SEQ ID NO: 6) |
| 4 | aggttcagtgca (SEQ ID NO: 7) |
|   | tgcactgaacct (SEQ ID NO: 8) |
| 5 | atcaggatacgc (SEQ ID NO: 9) |
|   | gcgtatcctgat (SEQ ID NO: 10) |
| 6 | atcattaccacc (SEQ ID NO: 11) |
|   | ggtggtaatgat (SEQ ID NO: 12) |
| 7 | attaacgggagc (SEQ ID NO: 13) |
|   | gctcccgttaat (SEQ ID NO: 14) |
| 8 | cagaggtcttaa (SEQ ID NO: 15) |
|   | ttaagacctctg (SEQ ID NO: 16) |
| 9 | caggtgtccatt (SEQ ID NO: 17) |
|   | aatggacacctg (SEQ ID NO: 18) |
| 10 | catccaatccag (SEQ ID NO: 19) |
|   | ctggattggatg (SEQ ID NO: 20) |
| 11 | cctacgatatac (SEQ ID NO: 21) |
|   | gtatatcgtagg (SEQ ID NO: 22) |
| 12 | cgaatgtagagt (SEQ ID NO: 23) |
|   | actctacattcg (SEQ ID NO: 24) |
| 13 | cggtttgagata (SEQ ID NO: 25) |
|   | tatctcaaaccg (SEQ ID NO: 26) |
| 14 | cttacaacgcca (SEQ ID NO: 27) |
|   | tggcgttgtaag (SEQ ID NO: 28) |
| 15 | ctttctcggcac (SEQ ID NO: 29) |
|   | gtgccgagaaag (SEQ ID NO: 30) |
| 16 | gacataaagcga (SEQ ID NO: 31) |
|   | tcgctttatgtc (SEQ ID NO: 32) |
| 17 | gccatagtctct (SEQ ID NO: 33) |
|   | agagactatggc (SEQ ID NO: 34) |

-continued

| Pair # | Sequence (5'-3') |
|---|---|
| 18 | gctaattcacca (SEQ ID NO: 35) |
| | tggtgaattagc (SEQ ID NO: 36) |
| 19 | ggtcgtgtttca (SEQ ID NO: 37) |
| | tgaaacacgacc (SEQ ID NO: 38) |
| 20 | gttgattctgtc (SEQ ID NO: 39) |
| | gacagaatcaac (SEQ ID NO: 40) |
| 21 | tacccggaataa (SEQ ID NO: 41) |
| | ttattccgggta (SEQ ID NO: 42) |
| 22 | tgcttgacttgg (SEQ ID NO: 43) |
| | ccaagtcaagca (SEQ ID NO: 44) |
| 23 | ttccacttaggg (SEQ ID NO: 45) |
| | ccctaagtggaa (SEQ ID NO: 46) |
| 24 | ttgtctagcggc (SEQ ID NO: 47) |
| | gccgctagacaa (SEQ ID NO: 48) |
| 25 | tttcccttgcta (SEQ ID NO: 49) |
| | tagcaagggaaa (SEQ ID NO: 50) |

In a particular embodiment, the targeting agent and the targeting agent complement comprise a pair of oligonucleotides, wherein the pair is selected from one of the following sequence pairs in Table 1(b):

| Pair | Name | Modification | Sequence |
|---|---|---|---|
| 1 | 3' Thiol Oligo 12b-1 | 3'-thiol C3 SS | acatcggtagtt (SEQ ID NO: 1) |
| | 3' Biotin Oligo 12b-1 | 3' biotin | aactaccgatgt (SEQ ID NO: 2) |
| 3 | 3'Thiol Oligo 12b-5 | 3'-thiol C3 SS | agaagaagatcc (SEQ ID NO: 5) |
| | 3' Biotin Oligo 12b-5 | 3' biotin | ggatcttcttct (SEQ ID NO: 6) |
| 6 | 3'Thiol Oligo 12b-12 | 3'-thiol C3 SS | atcattaccacc (SEQ ID NO: 11) |
| | 3' Biotin Oligo 12b-12 | 3' biotin | ggtggtaatgat (SEQ ID NO: 12) |
| 7 | 3'Thiol Oligo 12b-14 | 3'-thiol C3 SS | attaacgggagc (SEQ ID NO: 13) |
| | 3' Biotin Oligo 12b-14 | 3' biotin | gctcccgttaat (SEQ ID NO: 14) |
| 8 | 3' Thiol Oligo 12b-17 | 3'-thiol C3 SS | cagaggtcttaa (SEQ ID NO: 15) |
| | 3' Biotin Oligo 12b-17 | 3' biotin | ttaagacctctg (SEQ ID NO: 16) |

-continued

| Pair | Name | Modification | Sequence |
|---|---|---|---|
| 9 | 3'Thiol Oligo 12b-18 | 3'-thiol C3 SS | caggtgtccatt (SEQ ID NO: 17) |
| | 3' Biotin Oligo 12b-18 | 3' biotin | aatggacacctg (SEQ ID NO: 18) |
| 11 | 3'Thiol Oligo 12b-20 | 3'-thiol C3 SS | cctacgatatac (SEQ ID NO: 21) |
| | 3' Biotin Oligo 12b-20 | 3' biotin | gtatatcgtagg (SEQ ID NO: 22) |
| 12 | 3'Thiol Oligo 12b-21 | 3'-thiol C3 SS | cgaatgtagagt (SEQ ID NO: 23) |
| | 3' Biotin Oligo 12b-21 | 3' biotin | actctacattcg (SEQ ID NO: 24) |
| 13 | 3'Thiol Oligo 12b-22 | 3'-thiol C3 SS | cggtttgagata (SEQ ID NO: 25) |
| | 3' Biotin Oligo 12b-22 | 3' biotin | tatctcaaaccg (SEQ ID NO: 26) |
| 16 | 3'Thiol Oligo 12b-26 | 3'-thiol C3 SS | gacataaagcga (SEQ ID NO: 31) |
| | 3' Biotin Oligo 12b-26 | 3' biotin | tcgctttatgtc (SEQ ID NO: 32) |
| 17 | 3'Thiol Oligo 12b-28 | 3'-thiol C3 SS | gccatagtctct (SEQ ID NO: 33) |
| | 3' Biotin Oligo 12b-28 | 3' biotin | agagactatggc (SEQ ID NO: 34) |
| 18 | 3'Thiol Oligo 12b-30 | 3'-thiol C3 SS | gctaattcacca (SEQ ID NO: 35) |
| | 3' Biotin Oligo 12b-30 | 3' biotin | tggtgaattagc (SEQ ID NO: 36) |
| 20 | 3'Thiol Oligo 12b-33 | 3'-thiol C3 SS | gttgattctgtc (SEQ ID NO: 39) |
| | 3' Biotin Oligo 12b-33 | 3' biotin | gacagaatcaac (SEQ ID NO: 40) |
| 23 | 3'Thiol Oligo 12b-41 | 3'-thiol C3 SS | ttccacttaggg (SEQ ID NO: 45) |
| | 3' Biotin Oligo 12b-41 | 3' biotin | ccctaagtggaa (SEQ ID NO: 46) |
| 25 | 3'Thiol Oligo 12b-43 | 3'-thiol C3 SS | tttcccttgcta (SEQ ID NO: 49) |
| | 3' Biotin Oligo 12b-43 | 3' biotin | tagcaagggaaa (SEQ ID NO: 50) |

The targeting agent and targeting agent complement may be present in a 1:1 ratio. Alternatively, the targeting agent may be present in an excess, e.g., in a 2:1 ratio of targeting agent to targeting agent complement, to increase the likelihood of binding the targeting agent to its complement.

In one embodiment, suitable linking agents and supplemental linking agents include chemical moieties that react to form a linking complex. For example, the linking complex is formed by a binding interaction between chemical moieties present on the linking agent and supplemental linking agent, e.g., a thiol group and a maleimide or iodoacetamide groups; an aldehyde and a hydrazide; or an alkyne and an azide.

Alternatively, a linking complex can be formed by a protein-protein binding reaction between a linking agent and a supplemental linking agent. For example, a protein-protein binding reaction can be formed via binding between a receptor/ligand pair, hapten/antibody pair, antigen/antibody pair, epitope/antibody pair, mimitope/antibody pair, aptamer/target molecule pair, hybridization partners, and intercalater/target molecule pair. In one embodiment, the linking agent is biotin and the supplemental linking agent is streptavidin or avidin (or vice versa); or the linking agent is a peptide and the supplemental linking agent is an anti-peptide antibody (or vice versa).

Certain embodiments described herein employ linking agents that bind directly to supplemental linking agents. In these and other such embodiments, the linking and supplemental linking agents that bind to each other can be replaced with linking and supplemental linking agents that can concurrently bind to a bridging agent. In these alternate embodiments, a bridging agent is included in the mixture of the linking agent and supplemental linking agent, when forming the targeting complex. A bridging agent, if one is used, binds to the linking agent and the supplemental linking agent. For example, the bridging agent includes a binding site for the linking agent and an additional binding site for the supplemental linking agent, and the combination of the three components, i.e., the bridging agent, the linking agent, and the supplemental linking agent, comprises a bridging complex. In one embodiment, the bridging agent is streptavidin or avidin (each of which are tetramers with four independent binding sites for biotin) and the linking agent and supplemental linking agent are each biotin, such that the bridging complex comprises (biotin-(streptavidin (or avidin))-biotin).

In a preferred embodiment, a linking complex is formed by a binding reaction between a linking agent, $L_A$, and a supplemental linking agent, $L_A'$. A multiplex assay format may be configured to detect analytes A, B, and C, and therefore, the reagent complexes designed to interact with those individual analytes may include linking agents and supplemental linking agents selected from $L_A$ and $L_A'$, $L_B$ and $L_B'$, and $L_C$ and $L_C'$. Each of the linking agent/supplemental linking agent pairs used to construct the binding complexes may be the same or different. In a preferred embodiment, each of the linking agent/supplemental linking agent pairs comprise the same set of reagents. In a particularly preferred embodiment, each of the linking agent/supplemental linking agent pairs comprise, e.g., a biotin molecule as the linking agent on a binding reagent and a streptavidin or avidin molecule on a targeting agent as the supplemental linking agent (or vice versa). In addition, a linking complex can also be formed by a binding reaction between a biotin molecule on a binding reagent and a streptavidin or avidin molecule on a targeting agent, wherein the streptavidin or avidin molecule is bound to the targeting agent via a reaction with a biotin molecule (acting as a bridging agent) on the targeting agent. In a preferred embodiment, once a linking complex is formed between a biotin and streptavidin molecule on a binding reagent and a targeting agent, respectively (or vice versa), excess free biotin molecule can be added to prevent cross-reactivity between additional binding reagents and targeting agents that may be combined in solution.

(iv) Solid Phases

A wide variety of solid phases are suitable for use in the methods of the present invention including conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable solid phases also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like. A particle used in the present method may be comprised of any material suitable for attachment to one or more binding reagents, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles. The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

FIG. 6(a)-(c) illustrates various set of particles that can be used in the present invention. FIG. 6(a) shows a set of particles, provided in one or more vials, containers, or compartments, that are each modified with a distinct targeting agent. Alternatively, as shown in FIG. 6(b), a set of particles can be provided in one or more vials, containers, or compartments, that are each modified with a distinct binding reagent, the binding reagent being attached to the particle in a targeting complex that comprises the binding reagent (through linking a supplemental linking agents) to a targeting agent complement that is bound to a targeting agent on the surface of the particle. Still further, FIG. 6(c) shows yet another embodiment in which a mixed set of particles is provided, wherein a subset includes particles that are each modified with a distinct binding reagent (as in FIG. 6(b) and a subset includes particles that are each modified with a distinct targeting agent (as in FIG. 6(a)). The particles shown in FIG. 6(c) include a subset of preconfigured particles with binding reagents for a pre-determined set of analytes and a subset of non-configured particles that can be modified by a user to attach an additional set of binding reagents for an additional set of analytes, i.e., by binding the particles to an additional set of targeting complexes comprising additional binding reagents. These additional reagents may be provided by the user thereby allowing the user to add a set of user-defined assays to a pre-defined set of assays.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like. As indicated by the cross-hatching of the particles in FIGS. 6(a)-(c), one or more particles provided in a mixture or set of particles may be coded to be distinguishable from other particles in the mixture by virtue of particle optical properties, size, shape, imbedded optical patterns and the like.

Alternatively or additionally, the binding reagents can be bound via binding reagent complexes to different discrete binding domains on one or more solid phases, e.g., as in a binding array, such that discrete assay signals are generated on each binding domain and therefore, the different analytes bound to those domains can be measured independently. In one example of such an embodiment, the binding domains are prepared by immobilizing, on one or more surfaces, discrete domains of targeting agents that, through a binding reagent complex built on the individual domains, are configured to bind analytes of interest. Optionally, the surface(s) may define, in part, one or more boundaries of a container (e.g., a flow cell, well, cuvette, etc.) which holds the sample or through which the sample is passed. In a preferred embodiment, individual binding domains are formed on electrodes for use in electrochemical or electrochemiluminescence assays. Multiplexed measurement of analytes on a surface comprising a plurality of binding domains using electrochemiluminescence has been used in the Meso Scale Diagnostics, LLC, MULTI-ARRAY® and SECTOR® Imager line or products (see, e.g., U.S. Pat. Nos. 7,842,246 and 6,977,722, the disclosures of which are incorporated herein by reference in their entireties).

FIG. 6(d)-(f) illustrate various alternative plate formats including distinct binding domains that can be used in the present invention. FIG. 6(d) shows a surface bearing a plurality of binding domains that are each modified with a distinct targeting agent. Alternatively, as shown in FIG. 6(e), a surface can be provided bearing a plurality of binding domains that are each modified with a distinct binding reagent, the binding reagent being attached to the binding domain in a targeting complex that comprises the binding reagent (through linking a supplemental linking agents) to a targeting agent complement that is bound to a targeting agent on the binding domain. Still further, FIG. 6(f) shows yet another embodiment in which a mixed set of binding domains on a surface is provided, wherein a subset includes binding domains that are each modified with a distinct binding reagent (as in FIG. 6e) and a subset includes binding domains that are each modified by a distinct targeting agent (as in FIG. 6(d)). The binding domains shown in FIG. 6(f) include a subset of preconfigured binding domains with binding reagents for a pre-determined set of analytes and a subset of non-configured binding domains that can be modified by a user to attach an additional set of binding reagents for an additional set of analytes, i.e., by binding these non-configured binding domains to an additional set of targeting complexes comprising additional binding reagents. These additional reagents may be provided by the user, thereby allowing the user to add a set of user-defined assays to a pre-defined set of assays.

Figure 7:
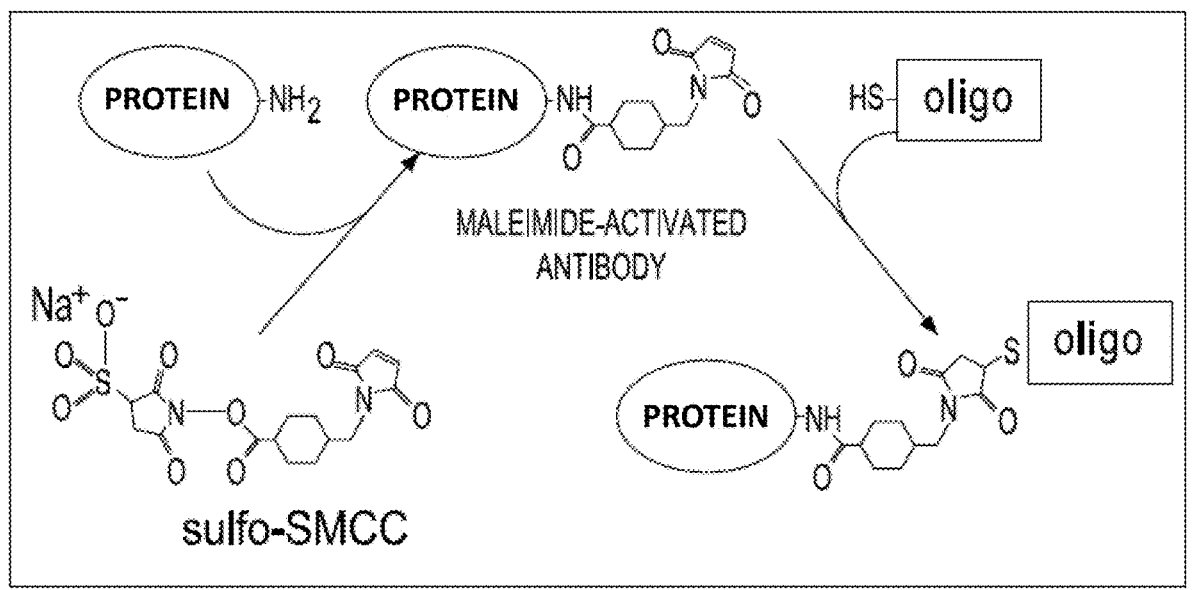
FIG. 7 shows a procedure to chemically modify an antibody with sulfo-SMCC to yield a maleimide-activated antibody which can be conjugated to an oligonucleotide via a thiol group on the oligonucleotide.

Reagents, i.e., targeting agents, can be bound to a surface by known methods, e.g., established methods for modifying particles or for forming arrays. One non-limiting example of a method of attaching a protein or oligonucleotide to a surface is illustrated in FIG. 7. This method uses Sulfosuccinimidyl-4-(N-maleimidomethyl)cyclohexane-1-carboxylate (Sulfo-SMCC), a well-established heterobifunctional cross-linking agent. Reaction of the N-hydroxysuccinimide (NHS) group of SMCC with bovine serum albumin (BSA) labels the BSA with thiol-reactive maleimide groups. The maleimide groups are, in turn, reacted with thiol-modified oligonucleotides to form BSA-oligonucleotide conjugates that are linked through stable thioether bonds. Arrays of these reagents can be formed by printing patterns of the reagents on surfaces that adsorb or react with proteins (such as BSA), thereby generating patterned arrays of the associated oligonucleotides. In one specific example, arrays are formed by printing arrays of the BSA-oligonucleotide conjugates on graphitic carbon surfaces, preferably screen printed carbon ink electrodes. Surprisingly, we have found that thiol-modified reagents including thiol-modified oligonucleotides react irreversibly with graphitic carbon surfaces including screen-printed carbon ink electrodes (even when not conjugated to a protein such as BSA). Accordingly, thiol-modified reagents (including thiol modified oligonucleotides and peptides) can be immobilized on carbon surfaces by incubating the carbon surfaces with a solution containing the reagents and allowing the reagent to irreversibly react with the surface. Furthermore, arrays of such thiol-modified reagents (including arrays comprising thiol-modified oligonucleotides and/or peptides) can be formed by printing solutions containing these reagents on carbon surfaces, incubating the patterned solutions on the surface and allowing the reagents to irreversibly react with the surface.

(v) Assay Devices and Supplementary Reagents

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

(vi) Measurement Methods

The methods of the invention can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase Accordingly, the methods of the invention may comprise such a wash step.

In one embodiment, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147, 806; 5,324,457; 5,591,581; 5,597,910; 5,641,623; 5,643, 713; 5,679,519; 5,705,402; 5,846,485; 5,866,434; 5,786, 141; 5,731,147; 6,066,448; 6,136,268; 5,776,672; 5,308, 754; 5,240,863; 6,207,369; 6,214,552 and 5,589,136 and Published PCT Nos. WO99/63347; WO00/03233; WO99/ 58962; WO99/32662; WO99/14599; WO98/12539; WO97/ 36931 and WO98/57154, all of which are incorporated herein by reference.

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

(vii) Kits

In one embodiment, the invention provides a kit including a surface, e.g., multi-well plate or plurality of particles, comprising a plurality of discrete binding domains each including a first and second targeting agent, e.g., a first and second oligonucleotide, and, in a separate vial, container, or compartment, a first oligonucleotide complement bound to a linking agent and a second oligonucleotide complement bound to a second linking agent. In a preferred embodiment, (i) the first targeting agent and the first targeting agent complement comprise a first pair of targeting agents, and (ii) the second targeting agent and the second targeting agent complement comprise a second pair of targeting agents. Preferably, the first and second pair of targeting agents comprise a first and second pair of oligonucleotides, respectively, selected from the pairs of sequences listed in Table 1.

The kit further includes, in separate vials, containers, or compartments, at least 4 oligonucleotides comprising a different sequence selected from the sequences listed in Table 1(a) and/or Table 1(b). These sequences may include four sequences selected from different pairs or may include more than one member of a pair.

The kit can include at least 7, 10, 16, or 25 surface bound oligonucleotides and corresponding oligonucleotide complements. The oligonucleotides configured for use as targeting agent complements can be provided pre-bound to a binding reagent such as an antibody or can be provided modified with a linking agent for attachment to a binding reagent by the user. Optionally, each oligonucleotide complement in the kit is coupled to a different binding reagent, e.g., antibody. The surface-bound oligonucleotides can be incorporated into an array comprising a plurality of at least 5 (7, 10, 16, or 25) oligonucleotides immobilized to each binding domain such that a different oligonucleotide sequence is immobilized to a discrete binding domain. In a specific embodiment, a multi-well plate can include one or more copies of an oligonucleotide array as described herein within at least one well of the plate, wherein the array is positioned on a plurality of binding domains. The plate can include at least 24, 96, or 384 wells and the array can include at least 7 oligonucleotides, or at least 10, 16, or 25 oligonucleotides.

In a specific embodiment, the kit includes a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from a different sequence pair from the set of sequence pairs listed in Table 1(a). In a specific embodiment, the kit includes a multi-well plate having one or more copies of an oligonucleotide array within at least one well(s) of the plate, the array is positioned on a plurality of binding domains, wherein one or more and optionally, at least 4 of the binding domains have immobilized thereon a different oligonucleotide sequence selected from a different sequence pair from the set of sequence pairs listed in Table 1(b). The kit may further comprise an additional set of oligonucleotides comprised of two or more oligonucleotides selected from the set of sequences in Table 1(a), and in a specific embodiment Table 1(b), wherein the additional oligonucleotides are complementary to the immobilized oligonucleotides.

The kit may further include one or more additional containers, vessels or compartments comprising: (i) a first binding reagent comprising a first linking agent, wherein the first binding reagent is specific for a first analyte in the sample, (ii) a first targeting agent complement comprising a supplemental linking agent, provided in a separate container, vessel or compartment or as a component of (i), (iii) a second binding reagent comprising a second linking agent, wherein the second binding reagent is specific for a second analyte in the sample, and (iv) a second targeting agent complement comprising a second supplemental linking agent, provided in a separate container, vessel or compartment or as a component of (iii).

Alternatively, the invention provides a kit for measuring a plurality of different analytes in a sample, the kit comprising: (a) a container, vessel or compartment comprising a solid support including a first targeting agent immobilized to a first region of the solid support and a second targeting agent immobilized to a second region of said solid support; and (b) one or more additional containers, vessels or compartments comprising: (i) a first binding reagent comprising a first linking agent, wherein said first binding reagent is specific for a first analyte in said sample, (ii) a first targeting agent complement comprising a supplemental linking agent, provided in a separate container, vessel or compartment or as a component of (b)(i), (iii) a second binding reagent comprising a second linking agent, wherein said second binding reagent is specific for a second analyte in said sample, and (iv) a second targeting agent complement comprising a second linking agent complement, provided in a separate container, vessel or compartment or as a component of (b)(iii).

The invention also contemplates a kit for measuring a plurality of different analytes in a sample, the kit comprising: (a) a container, vessel or compartment comprising on a solid support a first targeting agent immobilized to a first region of said solid support and a second targeting agent immobilized to a second region of said solid support; and (b) four or more additional containers, vessels or compartments comprising: (i) a first container comprising a first binding reagent comprising a first linking agent, wherein said first binding reagent is specific for a first analyte in said sample, (ii) a second container comprising a first targeting agent complement comprising a supplemental linking agent, provided in a separate container, vessel or compartment, (iii) a third container comprising a second binding reagent comprising a second linking agent, wherein said second binding reagent is specific for a second analyte in said sample, and (iv) a fourth container comprising a second targeting agent complement comprising a second supplemental linking agent, provided in a separate container, vessel or compartment.

Still further, the invention provides a kit for measuring a plurality of different analytes in a sample, the kit comprising: (a) a container, vessel or compartment comprising on a solid support a first targeting agent immobilized to a first region of said solid support and a second targeting agent immobilized to a second region of said solid support; and (b) two or more additional containers, vessels or compartments comprising: (i) a first container comprising a first binding reagent comprising a first linking agent, wherein said first binding reagent is specific for a first analyte in said sample, and a first targeting agent complement comprising a supplemental linking agent, and (ii) a second container comprising a second binding reagent comprising a second linking agent, wherein said second binding reagent is specific for a second analyte in said sample, and a second targeting agent complement comprising a second supplemental linking agent.

In a specific embodiment, the invention provides a kit comprising: (a) a multi-well plate comprising a plurality of discrete binding domains each comprising a first and second oligonucleotide, respectively, each of said first and second oligonucleotides are selected from the group consisting of the sequences listed in Table 1(a) and/or (b).

The kit can also include instructions for use of the multi-well plate in a method of conducting a binding assay for a plurality of analytes, said method comprising the steps of:

(a) forming a first binding reagent complex comprising a first binding reagent specific for a first analyte in said plurality of analytes and said first oligonucleotide, wherein said first binding reagent is bound to a linking agent and said first oligonucleotide is bound to a supplemental linking agent wherein said first binding reagent complex is formed by a reaction between said linking agent and said supplemental linking agent;

(b) forming a second binding reagent complex comprising a second binding reagent specific for a second analyte in said plurality of analytes and said second oligonucleotide, wherein said second binding reagent is bound to a second linking agent and said second oligonucleotide is bound to a second supplemental linking agent wherein said second binding reagent complex is formed by a reaction between said second linking agent and said second supplemental linking agent;

(c) mixing said first and second binding reagent complexes with said two or more binding domains each linked to a first oligonucleotide complement and a second oligonucleotide complement, respectively, under conditions sufficient to bind said first oligonucleotide to said first oligonucleotide complement and said second oligonucleotide to said second oligonucleotide complement;

(d) mixing a sample comprising said plurality of analytes to the mixture formed in step (c);

(e) adding a plurality of additional binding reagents to the mixture formed in step (d), wherein said plurality of additional binding reagents includes (i) a first detection reagent specific for said first analyte and/or a first binding reagent-first analyte complex; and (ii) a second detection reagent specific for said second analyte and/ or a second (f) binding reagent-second analyte complex; and measuring the amount of said first and second analytes bound to said binding domains.

In one specific embodiment, a multi-well assay plate can be used to configure an end-user developed assay panel, i.e., an assay panel built by the end-user with his/her binding reagents to conduct an assay with the plate. In this embodiment, the end-user designates which binding reagent is bound to each binding domain. A multi-well assay plate is provided that includes a plurality of discrete binding domains including a first binding domain with a first targeting agent and a second binding domain with a second targeting agent and, optionally, additional binding domains with additional targeting agents. Each of the binding domains are functionalized by the user by selecting individual binding reagents that will be attached to each of the plurality of binding domains via a binding reagent complex, as described herein. In a separate vial, container, or compartment, a set of targeting reagents (each attached to a linking agent) is provided that includes a first targeting agent complement, a second targeting agent complement, and optionally additional targeting agent complements. The first targeting agent and first targeting agent complement and the second targeting agent and second targeting agent complement constitute a first and second pair of targeting agents, respectively. Similarly, any additional targeting agent complements form pairs with the different additional targeting agents on the binding domains. In one preferred embodiment, the targeting agents and targeting agent complements are oligonucleotides (i.e., an oligonucleotide and its complement). In this embodiment, the first and second pairs of targeting agents, and any additional pairs of targeting agents, are selected from the list of sequences provided in Table 1(a) and/or Table 1(b).

Therefore, the user selects which targeting agent/targeting agent complement will be bound to each specific binding domain. The user also selects which binding reagent will be bound to each specific binding domain and forms a binding reagent complex that includes the targeting agent complement of the targeting agent attached to the designated binding domain.

The kit may provide reagents for the users to attach the supplementary linking agent to the users' binding reagents. When biotin is the supplementary linking agent, the kit may include biotin modified with a reactive functional group such as an NHS ester or hydrazide or maleimide. The plate and/or set of targeting reagents can further include a labeling kit for attaching a detectable label to an assay component, such as a detection reagent. For example, if the multi-well assay plate is configured to conduct an electrochemiluminescence reaction, the labeling kit can include a SULFO-TAG™ NHS ester, LC-biotin NHS ester, an optional spin column, and optional labeling buffer solution. Further provided can be ECL read buffer and optional assay and antibody diluents.

The set of targeting reagents preferably includes a quantity of targeting reagents that matches the number of binding domains present in the multi-well plate. For example, if the multi-well plate includes ten discrete binding domains, a set of 10 targeting reagents are used with that multi-well plate.

The targeting agents may be provided with a linking agent that directly binds to the supplementary linking agent, e.g., streptavidin or avidin when the supplementary linking agent is biotin. When the linking agent and supplementary linking agent are configured to be linked through a bridging agent (e.g., when both the linking and supplementary linking agents are biotin), the kit may also provide a bridging reagent solution (e.g., a solution of streptavidin or avidin) that can be used to attach the binding reagent to the targeting agent complement. The kit may also provide a reaction buffer that provides the appropriate conditions for the linking/bridging reactions and a reaction stop solution. When one or more of the linking reagents are biotin, the stop solution may include free biotin to block any unused biotin-binding sites in streptavidin or avidin that is present as a linking agent, supplemental linking agent or bridging agent.

In this embodiment, the user supplies the binding reagents, e.g., capture and detection antibodies, and designates which binding reagent will be attached to each of the binding domains. The binding reagent, e.g., capture antibody, is labeled with a selected linking agent, e.g., biotin, and attached to a member of a targeting agent pair via a supplemental linking agent, e.g., streptavidin. Meanwhile, the plate is prepared by binding the targeting agent to the selected binding domain. The modified binding reagent contacts the surface to form a surface-bound binding reagent complex that can be used in a subsequent binding assay for an analyte recognized by the binding reagent. The analyte of interest is detected by contacting the binding domain with a labeled binding reagent and measuring the presence of the label present at that binding domain.

Alternatively, a multi-well assay plate can be configured based on a user's specifications, e.g., from a catalog of available multiplexed assay panels and/or a user can select a set of analytes to configure a user-customized multiplexed assay for that set of analytes. A multiplexed assay panel should be selected and optimized such that individual assays function well together. For example, the sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

For a given immunoassay panel, the detection antibody concentration and the number of detectable labels per protein (L/P ratio) for the detection antibody are adjusted to bring the expected levels of all analytes into a quantifiable range at the same sample dilution. If one wants to increase the high end of the quantifiable range for a given analyte, then the L/P can be decreased and/or the detection antibody concentration is decreased. On the other hand, if one wants to increase the lower end of the quantifiable range, the L/P can be increased, the detection antibody concentration can be increased if it is not at the saturation level, and/or the background signal can be lowered.

Calibration standards for use with an assay panel are selected to provide the appropriate quantifiable range with the recommended sample dilution for the panel. The calibration standards have known concentrations of one of more of the analytes in the panel. Concentrations of the analytes in unknown samples are determined by comparison to these standards. In one embodiment, calibration standards comprise mixtures of the different analytes measured by an assay panel. Preferably, the analyte levels in a combined calibrator are selected such that the assay signals for each analyte are comparable, e.g., within a factor of two, a factor of five or a factor of 10. In another embodiment, calibration standards include mixtures of analytes from multiple different assay panels.

A calibration curve may be fit to the assay signals measured with calibration standards using, e.g., curve fits known in the art such as linear fits, 4-parameter logistic (4-PL) and 5-parameter (5-PL) fits. Using such fits, the concentration of analytes in an unknown sample may be determined by backfitting the measured assay signals to the calculated fits. Measurements with calibration standards may also be used to determine assay characteristics such as the limit of detection (LOD), limit of quantification (LOQ), dynamic range, and limit of linearity (LOL).

As part of a multiplexed panel development, assays are optimized to reduce calibrator and detection antibody non-specific binding. In sandwich immunoassays, specificity mainly comes from capture antibody binding. Some considerations for evaluating multiplexed panels include: (a) detection antibody non-specific binding to capture antibodies is reduced to lower background of assays in the panel, and this can be achieved by adjusting the concentrations and L/P of the detection antibodies; (b) non-specific binding of detection antibodies to other calibrators in the panel is also undesirable and should be minimized; (c) non-specific binding of other calibrators in the panel and other related analytes should be minimized; if there is calibrator non-specific binding, it can reduce the overall specificity of the assays in the panel and it can also yield unreliable results as there will be calibrator competition to bind the capture antibody.

In one specific embodiment, the kit further includes one or more reagents to insure that the correct steps of the assay protocol were followed. In addition, the variability of the assay steps can be measured independent of the assay. In this embodiment, a series of complementary oligonucleotides diluted in diluents used to run an assay are provided in the kit. As the correct steps are performed, the oligonucleotides in the various diluents bind, extending the chain. The final diluent can include the final complementary oligonucleotide with a reporter or label to provide a detectable indicator of the successful processing of the assay. For example, a first binding domain of a multi-well plate is coated with a BSA-oligonucleotide having sequence A. The assay diluent includes an oligonucleotide sequence complementary to sequence A, A', and an additional sequence, B. A and B do not interact with one another and specifically interact only with their complements. The final diluent contains a supplemental oligonucleotide comprising the complement of oligonucleotide B, B', and a detectable label. Therefore, detectable signal from the first binding domain can be used to verify that the sample was added or the detection moiety was added. The signal generated can also be used to detect if the correct volumes and concentrations of reagents were added, as well as whether there was variability in sample handling procedures and/or equipment. The oligonucleotide chain used in the process can include multiple overlapping sequences.

Different assays in the panel may require different incubation times and sample handling requirements for optimal performance. Therefore, the goal is to select a protocol that's optimized for most assays in the panel. Optimization of the assay protocol includes, but is not limited to, adjusting one or more of the following protocol parameters: timing (incubation time of each step), preparation procedure (calibrators, samples, controls, etc.), and number of wash steps.

These and other embodiments of the invention are illustrated in the following non-limited examples.

EXAMPLES

Example 1—Direct Assay Format

The procedure for the preparation and use of a multi-well plate for a direct assay is illustrated in FIG. 2. The experimental layout, i.e., which oligonucleotide sequence was located in which binding domain of a multi-well assay plate, was noted. The multi-well assay plate was obtained from Meso Scale Discovery, a division of Meso Scale Diagnostics, LLC (Rockville, MD). A working solution of each individual oligonucleotide sequence complement (550 uL) was prepared by diluting a stock solution of sequence complement about 50 times in Diluent 100 (stock solutions of oligonucleotide sequence complement and Diluent 100 are available from Meso Scale Discovery).

Figure 5A:
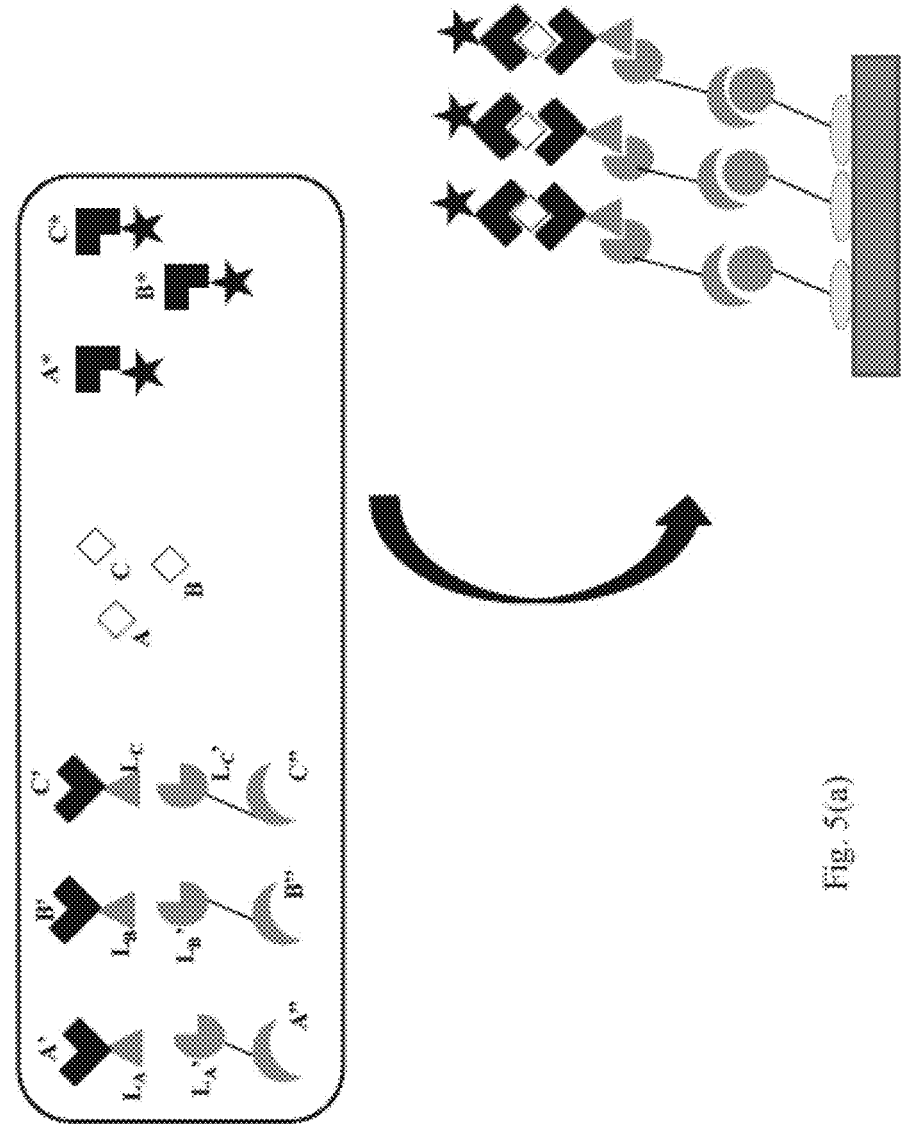
FIGS. 5(a)-(d) illustrate various combinations of reagents that can be used in the assay format of the invention.
Figure 5B:
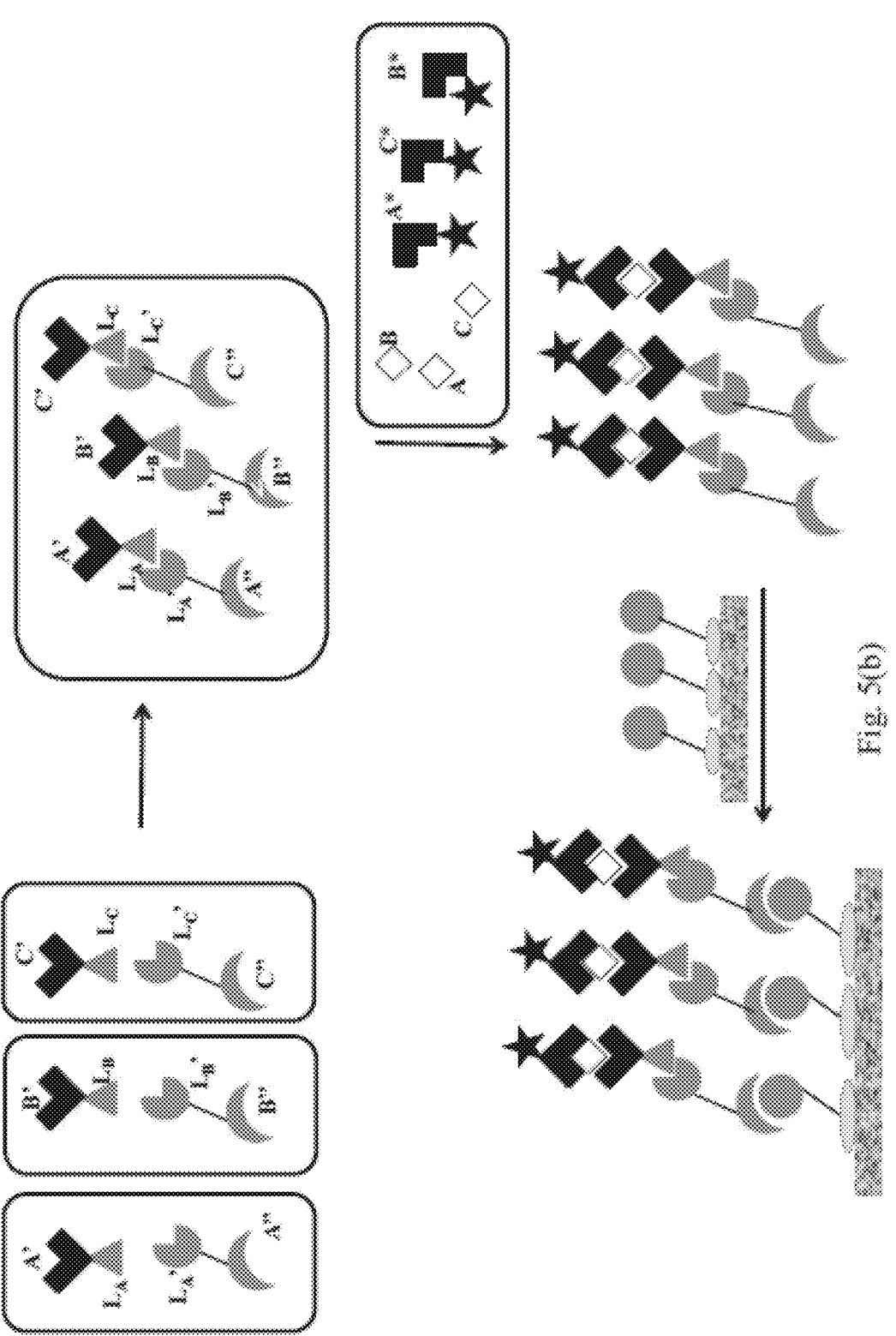
Figure 5C:
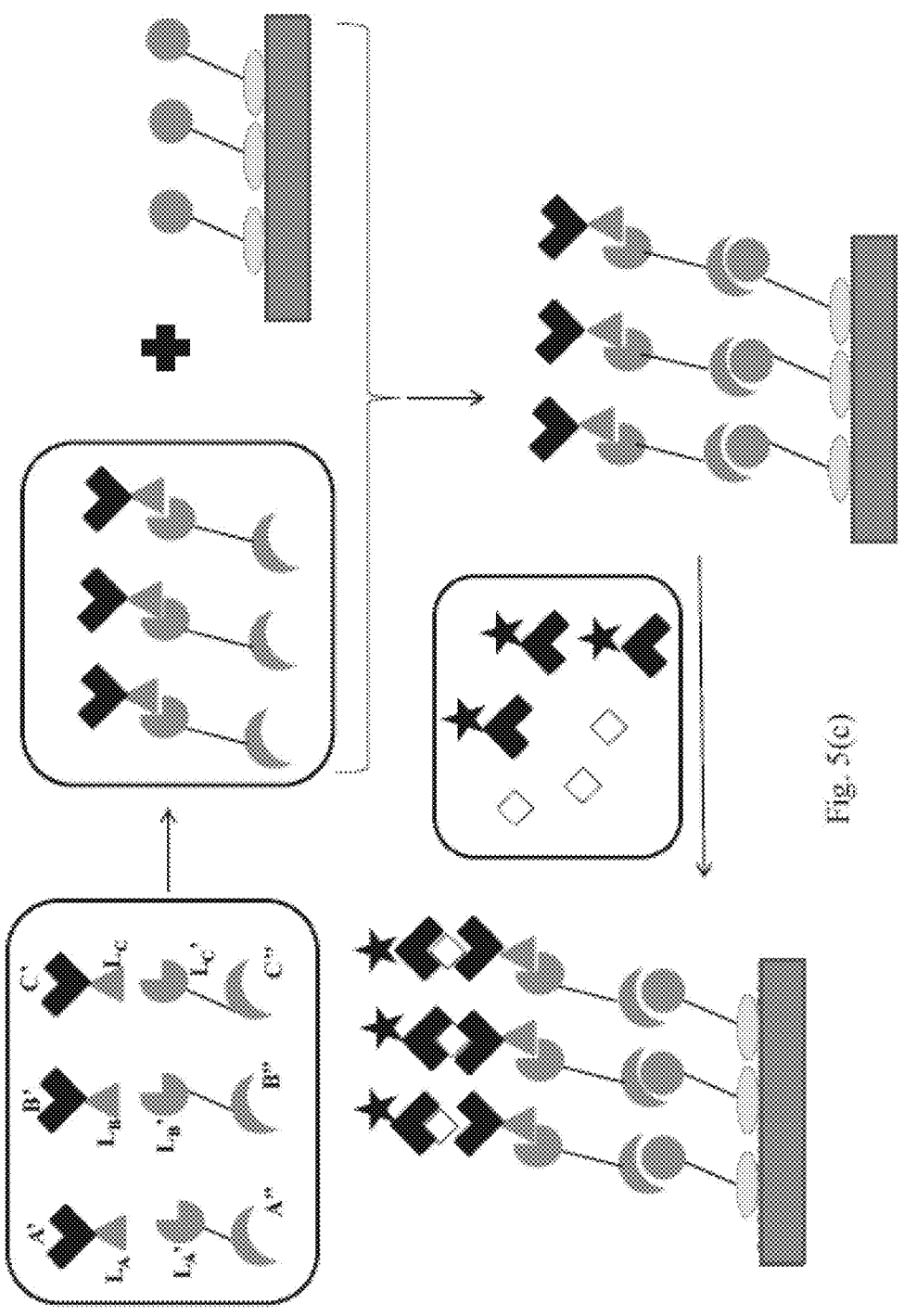
Figure 5D:
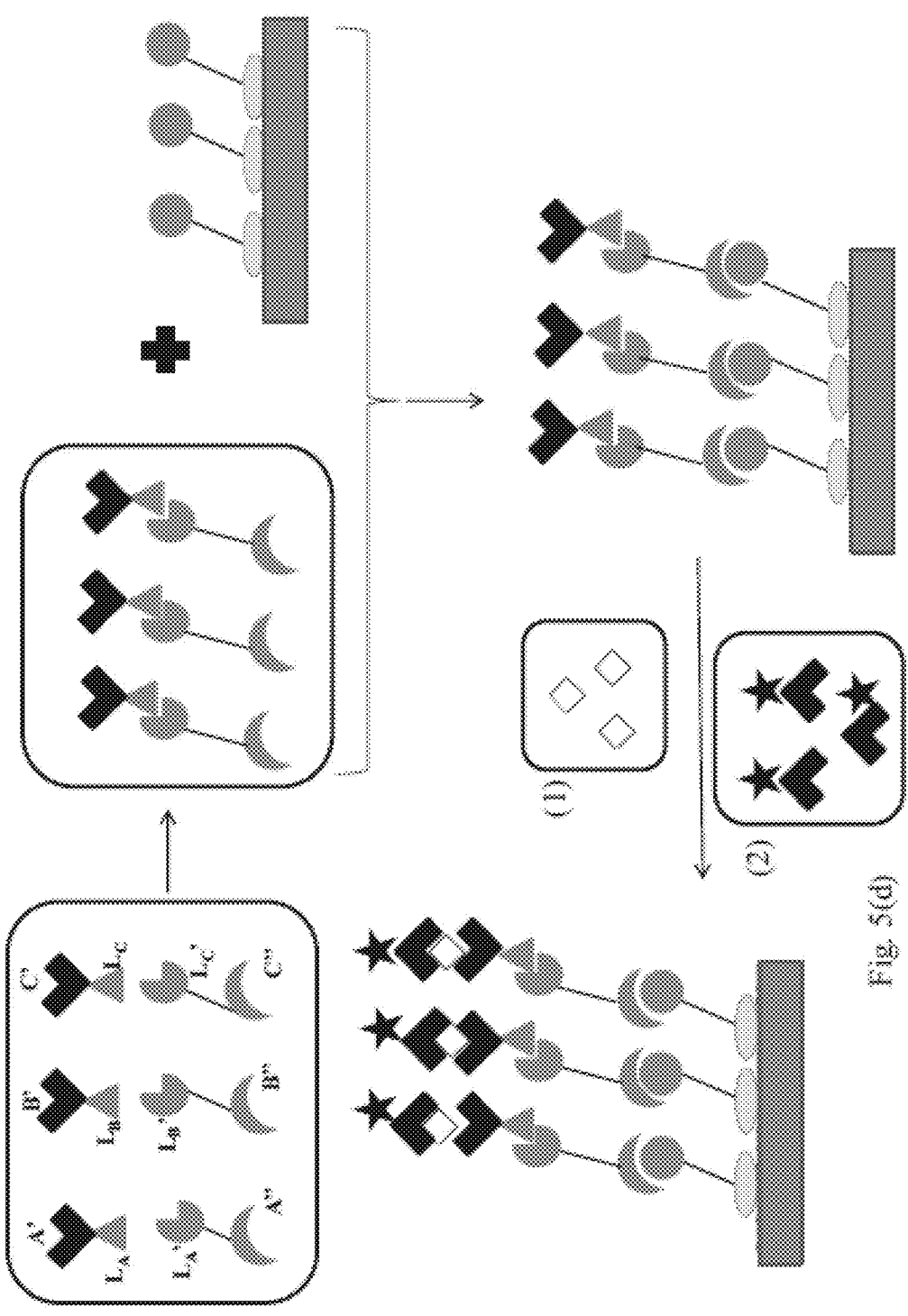

Each capture antibody was labeled with an oligonucleotide having a terminal thiol group using a bifunctional coupling reagent (sulfosuccinimidyl 4-(N-maléimido-méthyl)-1-cyclohexane carboxylate ("SMCC")) and conventional coupling protocols as shown in FIG. 5(d), e.g., protein is reacted with the NETS-ester in SMCC to label the protein and the resulting complex is reacted with thiolated oligonucleotides which reacts with the maleimide group in SMCC. A pooled solution (50 uL) of a set of antibody-oligo-conjugates was then added to each well of the multi-well plate in hybridization buffer for 1 hour at room temperature to hybridize the complementary oligonucleotide sequences and thereby immobilize the capture antibodies to the multi-well plate to form a plurality of binding reagent complexes.

A solution including a plurality of analytes (25 uL of MSD Diluent 2, with 25 uL calibrator solution of MSD Diluent 2) was added to each well of the prepared plate, incubated for 1 hour at room temperature, washed 3×PBS, and a set of labeled detection antibodies (50 uL of MSD Diluent 3) was added to each well of the multi-well plate. The plate was incubated with shaking and the wells were washed with 3×PBS, filled with 150 uL of Read Buffer T (Meso Scale Discovery) and analyzed on a SECTOR® Imager instrument.

This protocol was used to conduct an assay for a 7-plex chemokine panel and the result are shown in FIG. 8(a)-(g). The analytes assayed in this experiment were Eotaxin, MIP-1b, TARC, IL-8, MCP-4, IP-10, and MCP-1 (all human analytes). In addition, this protocol was used to conduct an assay for a 10-plex TH1/TH2 panel including IFNg, IL-1b, IL-2, IL-4, IL-5, IL-8, IL-10, IL-12p70, IL-13, and TNFa (all human analytes). The results for both assays were compared with a standard direct immunoassay absent oligonucleotides linkers.

Example 2—Indirect Assay Format Using an Oligonucleotide-SA Conjugate

The procedure for the preparation and use of a multi-well plate for an indirect assay using oligonucleotide-SA conjugates is illustrated in FIG. 9(a)-(c). The experimental layout for the multi-well assay plate was noted as in Example 1. A working solution of each individual oligonucleotide sequence complement bound to streptavidin (SA) (550 uL) was prepared by diluting a stock solution of sequence complement about 50 times in Diluent 100 (stock solutions of oligonucleotide sequence complement and Diluent 100 are available from Meso Scale Discovery). A solution of biotinylated antibody was added to the desired working solution of oligonucleotide sequence complement to prepare a set of individual biotinylated capture antibody/oligonucleotide-SA mixtures. The concentration of biotinylated antibody in the mixture was in the range of about 5-30 ug/mL. The mixture was gently mixed for 30-45 minutes at room temperature. Fifty (50) uL of biotin solution (Meso Scale Discovery) (approximately a three-fold excess of biotin) was added to each individual biotinylated antibody/oligonucleotide complement mixture and this mixture was gently mixed for 10-15 minutes at room temperature. Equal volumes (550 uL) of individual biotinylated antibody/oligonucleotide complements were combined and the total volume of the solution was adjusted to 5500 uL with the addition of a Conjugation Buffer (PBS with 0.1M EDTA at pH 7.4).

The multi-well plate was allowed to warm to room temperature (approximately 10 minutes). Fifty (50) uL of biotinylated antibodies/oligonucleotide complements was added to each well of the plate. The plate was covered with an adhesive seal and incubated for 1 hour on a plate shaker at room temperature. Each well was washed with phosphate buffered saline (PBS, 3×).

A solution including a plurality of analytes (25 uL of MSD Diluent 2, with 25 uL calibrator solution of MSD Diluent 2) was added to each well of the prepared plate, incubated for 1 hour at room temperature, washed 3×PBS, and a set of labeled detection antibodies (50 uL of MSD Diluent 3) was added to each well of the multi-well plate. The plate was incubated with shaking and the wells were washed with 3×PBS, filled with 150 uL of Read Buffer T (Meso Scale Discovery) and analyzed on a SECTOR® Imager instrument.

Example 3—Indirect Assay Format Using Neat SA/Biotinylated Oligonucleotides

The procedure for the preparation and use of a multi-well plate for an indirect assay using biotinylated capture antibodies, neat streptavidin, and biotinylated oligonucleotides is illustrated in FIG. 10(a)-(c). The experimental layout for the multi-well assay plate was noted as in Example 1. A working solution of an excess of each individual oligonucleotide sequence complement bound to streptavidin (SA) (550 uL) was prepared by diluting a stock solution of sequence complement about 50 times in Diluent 100 (stock solutions of oligonucleotide sequence complement and Diluent 100 are available from Meso Scale Discovery). A solution of biotinylated antibody was added to the desired working solution of oligonucleotide sequence complement to prepare a set of individual biotinylated capture antibody/oligonucleotide-SA mixtures. The concentration of biotinylated antibody in the mixture was in the range of about 5-30 ug/mL. The mixture was gently mixed for 30-45 minutes at room temperature. Fifty (50) uL of biotin solution (Meso Scale Discovery) (approximately a three-fold excess of biotin) was added to each individual biotinylated antibody/oligonucleotide complement mixture and this mixture was gently mixed for 10-15 minutes at room temperature. Equal volumes (550 uL) of individual biotinylated antibody/oligonucleotide complements were combined and the total volume of the solution was adjusted to 5500 uL with the addition of a Conjugation Buffer (available from Meso Scale Discovery).

The multi-well plate was allowed to warm to room temperature (approximately 10 minutes). Fifty (50) uL of biotinylated antibodies/oligonucleotide complements was added to each well of the plate. The plate was covered with an adhesive seal and incubated for 1 hour on a plate shaker at room temperature. Each well was washed with phosphate buffered saline (PBS, 3×).

A solution including a plurality of analytes (25 uL of MSD Diluent 2, with 25 uL calibrator solution of MSD Diluent 2) was added to each well of the prepared plate, incubated for 1 hour at room temperature, washed 3×PBS, and a set of labeled detection antibodies (50 uL of MSD Diluent 3) was added to each well of the multi-well plate. The plate was incubated with shaking and the wells were washed with 3×PBS, filled with 150 uL of Read Buffer T (Meso Scale Discovery) and analyzed on a SECTOR® Imager instrument.

Example 4—Comparative Results of Three Assay Formats Using 7-Plex Cytokine B Panel A 7-plex cytokine B panel (IL-8, hTNF-a, hEotaxin-3, h-Eotaxin, hMCP-1, HIP-10 and hMIP-1a) was tested in the assay formats described in Examples 1, 2, and 3, i.e. direct, indirect with oligonucleotide-SA conjugate and indirect with neat SA/biotinylated oligonucleotides. LOD values for assays were estimated from an 8-point calibration curve assume 2.5 standard deviations. The results are shown in FIG. 11(a)-(g). The LOD values for direct and indirect assay formats compare with LOD values observed for standard passive adsorption and immunoassay formats for all tested assays. The indirect approach with neat SA showed significant spread in LOD values: some assays, IL-8 and hIP-10, showed higher LOD values compared to the remaining assay formats, while Eotaxin and MIP-10 showed lower LOD values.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method of conducting a multiplexed binding assay for a plurality of analytes comprising a first analyte of interest and a second analyte of interest comprising (a) combining, in one or more steps, the following components:

(i) a sample comprising the plurality of analytes comprising the first analyte of interest and the second analyte of interest, (ii) a first targeting agent immobilized on a first binding domain, wherein the first targeting agent comprises an oligonucleotide, (iii) a first targeting agent complement connected to a first linking agent, wherein the first targeting agent complement comprises an oligonucleotide which is complementary to the oligonucleotide of the first targeting agent and forms a first oligonucleotide pair, (iv) a first binding reagent connected to a first supplemental linking agent, wherein the first binding reagent is a binding partner of the first analyte of interest, (v) a second targeting agent immobilized on a second binding domain, wherein the second targeting agent comprises an oligonucleotide, (vi) a second targeting agent complement connected to a second linking agent, wherein the second targeting agent complement comprises an oligonucleotide which is complementary to the oligonucleotide of the second targeting agent and forms a second oligonucleotide pair, and (vii) a second binding reagent connected to a second supplemental linking agent, wherein the second binding reagent is a binding partner of the second analyte of interest, wherein, the first linking agent binds to the first supplemental linking agent and the second linking agent binds to the second supplemental linking agent, (b) forming (i) a first binding complex on the first binding domain comprising the first targeting agent, the first targeting agent complement, the first binding reagent and the first analyte of interest, and (ii) a second binding complex on the second binding domain comprising the second targeting agent, the second targeting agent complement, the second binding reagent and the second analyte of interest, and (c) measuring the amount of the first analyte of interest and second analytes analyte of interest on the first binding domain and the second binding domain, respectively.

2. The method of claim 1, wherein the sample further comprises one or more additional analytes of interest comprising a first additional analyte of interest, and step (a) further comprises combining, in one or more steps, the components of step (a) with an additional targeting agent immobilized on an additional binding domain, an additional targeting agent complement connected to an additional linking agent, wherein the additional targeting agent complement is a binding partner of the additional targeting agent, and an additional binding reagent connected to an additional supplemental linking agent, wherein the additional binding reagent is a binding partner of the first additional analyte of interest, and wherein the additional linking agent binds to the additional supplemental linking agent;

step (b) further comprises forming an additional binding complex on the additional binding domain comprising the additional targeting agent, the additional targeting agent complement, the additional binding reagent and the first additional analyte of interest; and step (c) further comprises measuring the amount of the first additional analyte of interest on the additional binding domain.

3. The method of claim 1, wherein step (a) further comprises the steps of:

combining, in a first volume of liquid, the first targeting agent complement and the first binding reagent and forming a first targeting complex by linking the first targeting agent complement to the first binding reagent through the first linking agent and the first supplemental linking agent; and combining, in a second volume of liquid, the second targeting agent complement and the second binding reagent and forming a second targeting complex by linking the second targeting agent complement to the second binding reagent through the second linking agent and the second supplemental linking agent.

4. The method of claim 3, wherein step (a) further comprises the steps of:

forming a combination of the first targeting complex and the second targeting complex by combining the first targeting complex and the second targeting complex, contacting the combination of the first targeting complex and the second targeting complex with the first binding domain and the second binding domain, and binding the first targeting complex to the first targeting agent on the first binding domain and binding the second targeting complex to the second targeting agent on the second binding domain.

5. The method of claim 4, wherein the first targeting complex and the second targeting complex are combined with the sample prior to contacting the first targeting complex and the second targeting complex with the first binding domain and the second binding domain.

6. The method of claim 5, wherein the first analyte of interest binds to the first binding reagent in the first targeting complex and the second analyte of interest binds to the second binding reagent in the second targeting complex.

7. The method of claim 4, wherein the first targeting complex and the second targeting complex are combined with the sample after contacting the first targeting complex and the second targeting complex with the first binding domain and the second binding domain.

8. The method of claim 7, wherein the first analyte of interest binds to the first binding reagent in the first targeting complex and the second analyte of interest binds to the second binding reagent in the second targeting complex.

9. The method of claim 4, wherein the first targeting complex and the second targeting complex are combined with the sample and contacted with the first binding domain and the second binding domain at the same time.

10. The method of claim 9, wherein the first analyte of interest binds to the first binding reagent in the first targeting complex and the second analyte of interest binds to the second binding reagent in the second targeting complex.

11. The method of claim 3, wherein step (a) further comprises:

producing a mixture by combining the first targeting complex and the second targeting complex with the sample, wherein, in the mixture, the first analyte of interest binds to the first binding reagent in the first targeting complex and the second analyte of interest binds to the second binding reagent in the second targeting complex, and contacting the mixture of the first targeting complex and the second targeting complex, respectively, with the first binding domain and the second binding domain, wherein the first targeting complex binds to the first targeting agent on the first binding domain and the second targeting complex binds to the second targeting agent on the second binding domain.

12. The method of claim 1, wherein the first linking agent is bound to the first supplemental linking agent and the second linking agent is bound to the second supplemental linking agent through binding interactions between (a) a thiol group and a maleimide or iodoacetamide groups; (b) an aldehyde and a hydrazide; or (c) an alkyne and an azide.

13. The method of claim 1, wherein (a) each of the first linking agent and the second linking agent is biotin and each of the first supplemental linking agent and the second supplemental linking agent is streptavidin or avidin; or (b) each of the first linking agent and the second linking agent is streptavidin or avidin and each of the first supplemental linking agent and the second supplemental linking agent is biotin.

14. The method of claim 1, wherein the first binding reagent and the second binding reagent are antigens.

15. The method of claim 1, wherein the first binding reagent and the second binding reagent are antibodies.

16. The method of claim 1, wherein the method is a sandwich binding assay.

17. The method of claim 1, wherein the components combined in step (a) further comprise a first detection reagent that binds the first analyte of interest and a second detection reagent that binds the second analyte of interest, and wherein the first binding complex further comprises the first detection reagent and the second binding complex further comprises the second detection reagent.

18. The method of claim 17, wherein the first detection reagent comprises a first detectable label, wherein the second detection reagent comprises a second detectable label and wherein each of the first detectable label and the second detectable label is an electrochemiluminescent label and the measuring step (c) further comprises applying a voltage waveform to an electrode and measuring electrochemiluminescent signals wherein the first binding domain and the second binding domain are positioned on the electrode, and wherein an amount of an electrochemiluminescent signal from the first detectable label on the first binding complex correlates with an amount of first analyte in the sample and an amount of an electrochemiluminescent signal from the second detectable label on the second binding complex correlates with an amount of second analyte in the sample.

19. The method of claim 1, wherein the method is a competitive binding assay wherein the components of step (a) further comprise a first detection reagent that competes with the first analyte of interest for binding to the first binding reagent and a second detection reagent that competes with the second analyte of interest for binding to the second binding reagent.

20. The method of claim 1, wherein each of the first binding domain and the second binding domain is an element of an array of binding domains.

21. The method of claim 1, wherein each of the first binding domain and the second binding domain is positioned on a surface of a microparticle.

22. The method of claim 1, wherein the first oligonucleotide pair and the second oligonucleotide pair are different and each of the first oligonucleotide pair and the second oligonucleotide pair is selected from:

| Pair | Sequence | |
|---|---|---|
| 1 | acatcggtagtt | (SEQ ID NO: 1) |
|  | aactaccgatgt | (SEQ ID NO: 2) |
| 3 | agaagaagatcc | (SEQ ID NO: 5) |
|  | ggatcttcttct | (SEQ ID NO: 6) |
| 6 | atcattaccacc | (SEQ ID NO: 11) |
|  | ggtggtaatgat | (SEQ ID NO: 12) |
| 7 | attaacgggagc | (SEQ ID NO: 13) |
|  | gctcccgttaat | (SEQ ID NO: 14) |
| 8 | cagaggtcttaa | (SEQ ID NO: 15) |
|  | ttaagacctctg | (SEQ ID NO: 16) |
| 9 | caggtgtccatt | (SEQ ID NO: 17) |
|  | aatggacacctg | (SEQ ID NO: 18) |
| 11 | cctacgatatac | (SEQ ID NO: 21) |
|  | gtatatcgtagg | (SEQ ID NO: 22) |

-continued

| Pair | Sequence | |
|---|---|---|
| 12 | cgaatgtagagt | (SEQ ID NO: 23) |
|  | actctacattcg | (SEQ ID NO: 24) |
| 13 | cggtttgagata | (SEQ ID NO: 25) |
|  | tatctcaaaccg | (SEQ ID NO: 26) |
| 16 | gacataaagcga | (SEQ ID NO: 31) |
|  | tcgctttatgtc | (SEQ ID NO: 32) |
| 17 | gccatagtctct | (SEQ ID NO: 33) |
|  | agagactatggc | (SEQ ID NO: 34) |
| 18 | gctaattcacca | (SEQ ID NO: 35) |
|  | tggtgaattagc | (SEQ ID NO: 36) |
| 20 | gttgattctgtc | (SEQ ID NO: 39) |
|  | gacagaatcaac | (SEQ ID NO: 40) |
| 23 | ttccacttaggg | (SEQ ID NO: 45) |
|  | ccctaagtggaa | (SEQ ID NO: 46) |
| 25 | tttcccttgcta | (SEQ ID NO: 49) |
|  | tagcaagggaaa | (SEQ ID NO: 50). |

23. The method of claim 1, wherein the first binding reagent binds to the first analyte of interest and the second binding reagent binds the second analyte of interest.

24. The method of claim 23, wherein the first analyte of interest and the second analyte of interest are different analytes.

25. The method of claim 1, wherein the first targeting agent and the second targeting agent and the first targeting agent complement and the second targeting agent complement, respectively, are used to map the binding regions of the first binding reagent and the second binding reagent of a set of binding reagents to the first binding domain and the second binding domain of a set of binding domains and each binding reagent in the set of binding reagents binds to a different analyte of interest of the plurality of analytes in the sample.

26. The method of claim 1, wherein the plurality of analytes only has two analytes.

\* \* \* \* \*

SEQUENCE LISTING

<160> NUMBER OF SEQ ID NOS: 50

<210> SEQ ID NO 1
<211> LENGTH: 12
<212> TYPE: DNA
<213> ORGANISM: Artificial Sequence
<220> FEATURE:
<223> OTHER INFORMATION: oligonucleotide

<400> SEQUENCE: 1
acatcggtag tt                                                             12

<210> SEQ ID NO 2
<211> LENGTH: 12
<212> TYPE: DNA
<213> ORGANISM: Artificial Sequence
<220> FEATURE:
<223> OTHER INFORMATION: oligonucleotide

<400> SEQUENCE: 2
aactaccgat gt                                                             12

<210> SEQ ID NO 3
<211> LENGTH: 12
<212> TYPE: DNA
<213> ORGANISM: Artificial Sequence
<220> FEATURE:
<223> OTHER INFORMATION: oligonucleotide

<400> SEQUENCE: 3
acgtcccagt tg                                                             12

<210> SEQ ID NO 4
<211> LENGTH: 12
<212> TYPE: DNA
<213> ORGANISM: Artificial Sequence
<220> FEATURE:
<223> OTHER INFORMATION: oligonucleotide

<400> SEQUENCE: 4
caactgggac gt                                                             12

<210> SEQ ID NO 5
<211> LENGTH: 12
<212> TYPE: DNA
<213> ORGANISM: Artificial Sequence
<220> FEATURE:
<223> OTHER INFORMATION: oligonucleotide

<400> SEQUENCE: 5
agaagaagat cc                                                             12

<210> SEQ ID NO 6
<211> LENGTH: 12
<212> TYPE: DNA
<213> ORGANISM: Artificial Sequence
<220> FEATURE:
<223> OTHER INFORMATION: oligonucleotide

<400> SEQUENCE: 6
ggatcttctt ct                                                             12

<210> SEQ ID NO 7
<211> LENGTH: 12
<212> TYPE: DNA
<213> ORGANISM: Artificial Sequence -continued

```
<220> FEATURE:
<223> OTHER INFORMATION: oligonucleotide

<400> SEQUENCE: 7
aggttcagtg ca                                                    12

<210> SEQ ID NO 8
<211> LENGTH: 12
<212> TYPE: DNA
<213> ORGANISM: Artificial Sequence
<220> FEATURE:
<223> OTHER INFORMATION: oligonucleotide

<400> SEQUENCE: 8
tgcactgaac ct                                                    12

<210> SEQ ID NO 9
<211> LENGTH: 12
<212> TYPE: DNA
<213> ORGANISM: Artificial Sequence
<220> FEATURE:
<223> OTHER INFORMATION: oligonucleotide

<400> SEQUENCE: 9
atcaggatac gc                                                    12

<210> SEQ ID NO 10
<211> LENGTH: 12
<212> TYPE: DNA
<213> ORGANISM: Artificial Sequence
<220> FEATURE:
<223> OTHER INFORMATION: oligonucleotide

<400> SEQUENCE: 10
gcgtatcctg at                                                    12

<210> SEQ ID NO 11
<211> LENGTH: 12
<212> TYPE: DNA
<213> ORGANISM: Artificial Sequence
<220> FEATURE:
<223> OTHER INFORMATION: oligonucleotide

<400> SEQUENCE: 11
atcattacca cc                                                    12

<210> SEQ ID NO 12
<211> LENGTH: 12
<212> TYPE: DNA
<213> ORGANISM: Artificial Sequence
<220> FEATURE:
<223> OTHER INFORMATION: oligonucleotide

<400> SEQUENCE: 12
ggtggtaatg at                                                    12

<210> SEQ ID NO 13
<211> LENGTH: 12
<212> TYPE: DNA
<213> ORGANISM: Artificial Sequence
<220> FEATURE:
<223> OTHER INFORMATION: oligonucleotide

<400> SEQUENCE: 13
attaacggga gc                                                    12
```

-continued

```
<210> SEQ ID NO 14
<211> LENGTH: 12
<212> TYPE: DNA
<213> ORGANISM: Artificial Sequence
<220> FEATURE:
<223> OTHER INFORMATION: oligonucleotide

<400> SEQUENCE: 14
gctcccgtta at                                                      12

<210> SEQ ID NO 15
<211> LENGTH: 12
<212> TYPE: DNA
<213> ORGANISM: Artificial Sequence
<220> FEATURE:
<223> OTHER INFORMATION: oligonucleotide

<400> SEQUENCE: 15
cagaggtctt aa                                                      12

<210> SEQ ID NO 16
<211> LENGTH: 12
<212> TYPE: DNA
<213> ORGANISM: Artificial Sequence
<220> FEATURE:
<223> OTHER INFORMATION: oligonucleotide

<400> SEQUENCE: 16
ttaagacctc tg                                                      12

<210> SEQ ID NO 17
<211> LENGTH: 12
<212> TYPE: DNA
<213> ORGANISM: Artificial Sequence
<220> FEATURE:
<223> OTHER INFORMATION: oligonucleotide

<400> SEQUENCE: 17
caggtgtcca tt                                                      12

<210> SEQ ID NO 18
<211> LENGTH: 12
<212> TYPE: DNA
<213> ORGANISM: Artificial Sequence
<220> FEATURE:
<223> OTHER INFORMATION: oligonucleotide

<400> SEQUENCE: 18
aatggacacc tg                                                      12

<210> SEQ ID NO 19
<211> LENGTH: 12
<212> TYPE: DNA
<213> ORGANISM: Artificial Sequence
<220> FEATURE:
<223> OTHER INFORMATION: oligonucleotide

<400> SEQUENCE: 19
catccaatcc ag                                                      12

<210> SEQ ID NO 20
<211> LENGTH: 12
<212> TYPE: DNA
<213> ORGANISM: Artificial Sequence
<220> FEATURE:
<223> OTHER INFORMATION: oligonucleotide
```

-continued

<400> SEQUENCE: 20
ctggattgga tg                                                    12

<210> SEQ ID NO 21
<211> LENGTH: 12
<212> TYPE: DNA
<213> ORGANISM: Artificial Sequence
<220> FEATURE:
<223> OTHER INFORMATION: oligonucleotide

<400> SEQUENCE: 21
cctacgatat ac                                                    12

<210> SEQ ID NO 22
<211> LENGTH: 12
<212> TYPE: DNA
<213> ORGANISM: Artificial Sequence
<220> FEATURE:
<223> OTHER INFORMATION: oligonucleotide

<400> SEQUENCE: 22
gtatatcgta gg                                                    12

<210> SEQ ID NO 23
<211> LENGTH: 12
<212> TYPE: DNA
<213> ORGANISM: Artificial Sequence
<220> FEATURE:
<223> OTHER INFORMATION: oligonucleotide

<400> SEQUENCE: 23
cgaatgtaga gt                                                    12

<210> SEQ ID NO 24
<211> LENGTH: 12
<212> TYPE: DNA
<213> ORGANISM: Artificial Sequence
<220> FEATURE:
<223> OTHER INFORMATION: oligonucleotide

<400> SEQUENCE: 24
actctacatt cg                                                    12

<210> SEQ ID NO 25
<211> LENGTH: 12
<212> TYPE: DNA
<213> ORGANISM: Artificial Sequence
<220> FEATURE:
<223> OTHER INFORMATION: oligonucleotide

<400> SEQUENCE: 25
cggtttgaga ta                                                    12

<210> SEQ ID NO 26
<211> LENGTH: 12
<212> TYPE: DNA
<213> ORGANISM: Artificial Sequence
<220> FEATURE:
<223> OTHER INFORMATION: oligonucleotide

<400> SEQUENCE: 26
tatctcaaac cg                                                    12

<210> SEQ ID NO 27

```
<211> LENGTH: 12
<212> TYPE: DNA
<213> ORGANISM: Artificial Sequence
<220> FEATURE:
<223> OTHER INFORMATION: oligonucleotide

<400> SEQUENCE: 27
cttacaacgc ca                                                    12

<210> SEQ ID NO 28
<211> LENGTH: 12
<212> TYPE: DNA
<213> ORGANISM: Artificial Sequence
<220> FEATURE:
<223> OTHER INFORMATION: oligonucleotide

<400> SEQUENCE: 28
tggcgttgta ag                                                    12

<210> SEQ ID NO 29
<211> LENGTH: 12
<212> TYPE: DNA
<213> ORGANISM: Artificial Sequence
<220> FEATURE:
<223> OTHER INFORMATION: oligonucleotide

<400> SEQUENCE: 29
ctttctcggc ac                                                    12

<210> SEQ ID NO 30
<211> LENGTH: 12
<212> TYPE: DNA
<213> ORGANISM: Artificial Sequence
<220> FEATURE:
<223> OTHER INFORMATION: oligonucleotide

<400> SEQUENCE: 30
gtgccgagaa ag                                                    12

<210> SEQ ID NO 31
<211> LENGTH: 12
<212> TYPE: DNA
<213> ORGANISM: Artificial Sequence
<220> FEATURE:
<223> OTHER INFORMATION: oligonucleotide

<400> SEQUENCE: 31
gacataaagc ga                                                    12

<210> SEQ ID NO 32
<211> LENGTH: 12
<212> TYPE: DNA
<213> ORGANISM: Artificial Sequence
<220> FEATURE:
<223> OTHER INFORMATION: oligonucleotide

<400> SEQUENCE: 32
tcgctttatg tc                                                    12

<210> SEQ ID NO 33
<211> LENGTH: 12
<212> TYPE: DNA
<213> ORGANISM: Artificial Sequence
<220> FEATURE:
<223> OTHER INFORMATION: oligonucleotide

<400> SEQUENCE: 33
```

-continued

```
gccatagtct ct                                                12

<210> SEQ ID NO 34
<211> LENGTH: 12
<212> TYPE: DNA
<213> ORGANISM: Artificial Sequence
<220> FEATURE:
<223> OTHER INFORMATION: oligonucleotide

<400> SEQUENCE: 34
agagactatg gc                                                12

<210> SEQ ID NO 35
<211> LENGTH: 12
<212> TYPE: DNA
<213> ORGANISM: Artificial Sequence
<220> FEATURE:
<223> OTHER INFORMATION: oligonucleotide

<400> SEQUENCE: 35
gctaattcac ca                                                12

<210> SEQ ID NO 36
<211> LENGTH: 12
<212> TYPE: DNA
<213> ORGANISM: Artificial Sequence
<220> FEATURE:
<223> OTHER INFORMATION: oligonucleotide

<400> SEQUENCE: 36
tggtgaatta gc                                                12

<210> SEQ ID NO 37
<211> LENGTH: 12
<212> TYPE: DNA
<213> ORGANISM: Artificial Sequence
<220> FEATURE:
<223> OTHER INFORMATION: oligonucleotide

<400> SEQUENCE: 37
ggtcgtgttt ca                                                12

<210> SEQ ID NO 38
<211> LENGTH: 12
<212> TYPE: DNA
<213> ORGANISM: Artificial Sequence
<220> FEATURE:
<223> OTHER INFORMATION: oligonucleotide

<400> SEQUENCE: 38
tgaaacacga cc                                                12

<210> SEQ ID NO 39
<211> LENGTH: 12
<212> TYPE: DNA
<213> ORGANISM: Artificial Sequence
<220> FEATURE:
<223> OTHER INFORMATION: oligonucleotide

<400> SEQUENCE: 39
gttgattctg tc                                                12

<210> SEQ ID NO 40
<211> LENGTH: 12
<212> TYPE: DNA
```

-continued

```
<213> ORGANISM: Artificial Sequence
<220> FEATURE:
<223> OTHER INFORMATION: oligonucleotide

<400> SEQUENCE: 40
gacagaatca ac                                                   12

<210> SEQ ID NO 41
<211> LENGTH: 12
<212> TYPE: DNA
<213> ORGANISM: Artificial Sequence
<220> FEATURE:
<223> OTHER INFORMATION: oligonucleotide

<400> SEQUENCE: 41
tacccggaat aa                                                   12

<210> SEQ ID NO 42
<211> LENGTH: 12
<212> TYPE: DNA
<213> ORGANISM: Artificial Sequence
<220> FEATURE:
<223> OTHER INFORMATION: oligonucleotide

<400> SEQUENCE: 42
ttattccggg ta                                                   12

<210> SEQ ID NO 43
<211> LENGTH: 12
<212> TYPE: DNA
<213> ORGANISM: Artificial Sequence
<220> FEATURE:
<223> OTHER INFORMATION: oligonucleotide

<400> SEQUENCE: 43
tgcttgactt gg                                                   12

<210> SEQ ID NO 44
<211> LENGTH: 12
<212> TYPE: DNA
<213> ORGANISM: Artificial Sequence
<220> FEATURE:
<223> OTHER INFORMATION: oligonucleotide

<400> SEQUENCE: 44
ccaagtcaag ca                                                   12

<210> SEQ ID NO 45
<211> LENGTH: 12
<212> TYPE: DNA
<213> ORGANISM: Artificial Sequence
<220> FEATURE:
<223> OTHER INFORMATION: oligonucleotide

<400> SEQUENCE: 45
ttccacttag gg                                                   12

<210> SEQ ID NO 46
<211> LENGTH: 12
<212> TYPE: DNA
<213> ORGANISM: Artificial Sequence
<220> FEATURE:
<223> OTHER INFORMATION: oligonucleotide

<400> SEQUENCE: 46
ccctaagtgg aa                                                   12
```

-continued

```
<210> SEQ ID NO 47
<211> LENGTH: 12
<212> TYPE: DNA
<213> ORGANISM: Artificial Sequence
<220> FEATURE:
<223> OTHER INFORMATION: oligonucleotide

<400> SEQUENCE: 47
ttgtctagcg gc                                                    12

<210> SEQ ID NO 48
<211> LENGTH: 12
<212> TYPE: DNA
<213> ORGANISM: Artificial Sequence
<220> FEATURE:
<223> OTHER INFORMATION: oligonucleotide

<400> SEQUENCE: 48
gccgctagac aa                                                    12

<210> SEQ ID NO 49
<211> LENGTH: 12
<212> TYPE: DNA
<213> ORGANISM: Artificial Sequence
<220> FEATURE:
<223> OTHER INFORMATION: oligonucleotide

<400> SEQUENCE: 49
tttcccttgc ta                                                    12

<210> SEQ ID NO 50
<211> LENGTH: 12
<212> TYPE: DNA
<213> ORGANISM: Artificial Sequence
<220> FEATURE:
<223> OTHER INFORMATION: oligonucleotide

<400> SEQUENCE: 50
tagcaaggga aa                                                    12
```